US011591604B2

(12) United States Patent
Lu et al.

(10) Patent No.: US 11,591,604 B2
(45) Date of Patent: Feb. 28, 2023

(54) GENE EXPRESSION IN BACTEROIDES

(71) Applicant: Massachusetts Institute of Technology, Cambridge, MA (US)

(72) Inventors: Timothy Kuan-Ta Lu, Cambridge, MA (US); Mark K. Mimee, Cambridge, MA (US); Christopher Voigt, Belmont, MA (US); Alex C. Tucker, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 307 days.

(21) Appl. No.: 15/580,859

(22) PCT Filed: Jun. 10, 2016

(86) PCT No.: PCT/US2016/036811
§ 371 (c)(1),
(2) Date: Dec. 8, 2017

(87) PCT Pub. No.: WO2016/201174
PCT Pub. Date: Dec. 15, 2016

(65) Prior Publication Data
US 2018/0163216 A1 Jun. 14, 2018

Related U.S. Application Data

(60) Provisional application No. 62/173,481, filed on Jun. 10, 2015.

(51) Int. Cl.
*A61K 35/741* (2015.01)
*C12N 15/74* (2006.01)
*A61K 48/00* (2006.01)
*C12N 9/12* (2006.01)
*C12N 9/22* (2006.01)
*C12N 9/96* (2006.01)
*C12N 15/11* (2006.01)
*C12N 15/67* (2006.01)
*C12N 15/90* (2006.01)

(52) U.S. Cl.
CPC ............ *C12N 15/74* (2013.01); *A61K 35/741* (2013.01); *A61K 48/0066* (2013.01); *C12N 9/12* (2013.01); *C12N 9/22* (2013.01); *C12N 9/96* (2013.01); *C12N 15/11* (2013.01); *C12N 15/67* (2013.01); *C12N 15/902* (2013.01); *C12N 2310/14* (2013.01); *C12N 2310/20* (2017.05); *C12N 2800/80* (2013.01); *C12N 2840/203* (2013.01)

(58) Field of Classification Search
None
See application file for complete search history.

(56) References Cited

U.S. PATENT DOCUMENTS

2015/0004705 A1* 1/2015 Lu ............................ C12N 7/00
435/471
2015/0089681 A1* 3/2015 Van Der Oost ........ C12N 15/10
800/25

FOREIGN PATENT DOCUMENTS

WO WO 2010/042894 A1 4/2010

OTHER PUBLICATIONS

Mastropaolo et al. Microbiology 155:2683-2693, 2009.*
Horn et al. Frontiers in Microbiology 7: pp. 1-9, 2016.*
International Search Report and Written Opinion dated Mar. 13, 2017 for Application No. PCT/US2016/036811.
International Preliminary Report on Patentability dated Dec. 21, 2017 for Application No. PCT/US2016/036811.
Partial European Search Report dated Dec. 10, 2018 for Application No. 16808336.8.
Extended European Search Report dated Mar. 21, 2019 for Application No. 16808336.8.
Mahowald et al., Characterizing a model human gut microbiota composed of members of its two dominant bacterial phyla. Proc Natl Acad Sci U S A. Apr. 7, 2009;106(14):5859-64. doi: 10.1073/pnas.0901529106. Epub Mar. 24, 2009.
Mimee et al., Programming a Human Commensal Bacterium, Bacteroides thetaiotaomicron, to Sense and Respond to Stimuli in the Murine Gut Microbiota. Cell Syst. Jul. 29, 2015;1(1):62-71.
Nakayama-Imaohji et al., Identification of the site-specific DNA invertase responsible for the phase variation of SusC/SusD family outer membrane proteins in Bacteroides fragilis. J Bacteriol. Oct. 2009;191(19):6003-11. doi: 10.1128/JB.00687-09. Epub Jul. 31, 2009.
Parker et al., Development of an IPTG inducible expression vector adapted for Bacteroides fragilis. Plasmid. Sep. 2012;68(2):86-92. doi: 10.1016/j.plasmid.2012.03.002. Epub Apr. 1, 2012.
Salyers et al., Starting a new genetic system: lessons from Bacteroides. Methods. Jan. 2000;20(1):35-46.
Wang et al., Characterization of a Bacteroides mobilizable transposon, NBU2, which carries a functional lincomycin resistance gene. J Bacteriol. Jun. 2000;182(12):3559-71.
Wegmann et al., Defining the Bacteroides ribosomal binding site. Appl Environ Microbiol. Mar. 2013;79(6):1980-9. doi: 10.1128/AEM.03086-12. Epub Jan. 18, 2013.
Wexler, Bacteroides: the good, the bad, and the nitty-gritty. Clin Microbiol Rev. Oct. 2007;20(4):593-621.
Xu et al., A genomic view of the human-Bacteroides thetaiotaomicron symbiosis. Science. Mar. 28, 2003;299(5615):2074-6.
Zocco et al., Bacteroides thetaiotaomicron in the gut: molecular aspects of their interaction. Dig Liver Dis. Aug. 2007;39(8):707-12. Epub Jun. 29, 2007.

(Continued)

Primary Examiner — S. Devi
(74) Attorney, Agent, or Firm — Wolf, Greenfield & Sacks, P.C.

(57) ABSTRACT

Provided herein, in some aspects, are tools (e.g., methods, compositions and nucleic acids) for building genetic circuits in *Bacteroides* and *Parabacteroides* bacteria, as well as the bacteria containing the genetic circuits.

16 Claims, 16 Drawing Sheets
Specification includes a Sequence Listing.

(56) References Cited

OTHER PUBLICATIONS

Bayley et al., Analysis of cepA and other Bacteroides fragilis genes reveals a unique promoter structure. FEMS Microbiol Lett. Dec. 1, 2000;193(1):149-54.
Becker et al., Human intestinal microbiota: characterization of a simplified and stable gnotobiotic rat model. Gut Microbes. 2011;2(1):25-33. doi: 10.4161/gmic.2.1.14651.
Bikard et al., Programmable repression and activation of bacterial gene expression using an engineered CRISPR-Cas system. Nucleic Acids Res. Aug. 2013;41(15):7429-37. doi: 10.1093/nar/gkt520. Epub Jun. 12, 2013.
Bloom et al., Commensal Bacteroides species induce colitis in host-genotype-specific fashion in a mouse model of inflammatory bowel disease. Cell Host Microbe. May 19, 2011;9(5):390-403. doi: 10.1016/j.chom.2011.04.009.
Bonnet et al., Rewritable digital data storage in live cells via engineered control of recombination directionality. PNAS. Jun. 5, 2012;109(23):8884-9.
Bonnet et al., Amplifying genetic logic gates. Science. May 3, 2013;340(6132):599-603. doi: 10.1126/science.1232758. Epub Mar. 28, 2013.
Cox et al., Programming gene expression with combinatorial promoters. Mol Syst Biol. 2007;3:145, 11 pages. Epub Nov. 13, 2007.
Cullen et al., Antimicrobial peptide resistance mediates resilience of prominent gut commensals during inflammation. Science. 2015;45:39-45.
Gevers et al., The Human Microbiome Project Consortium. Structure, function and diversity of the healthy human microbiome. Nature. Jun. 2012;486(7402):207-14.
Gordley et al., Synthesis of programmable integrases. PNAS USA. Mar. 31, 2009;106(13):5053-8.
Goto et al., Complete Sequence of pBFUK1, a Carbapenemase-Harboring Mobilizable Plasmid From Bacteroides Fragilis, and Distribution of pBFUK1-like Plasmids Among Carbapenem-Resistant B. Fragilis Clinical Isolates. J Antibiot. Dec. 12, 2012;66(4):239-42. Epub Apr. 2013.
Groth et al., Phage Integrases: Biology and Applications. J Mol Biol. 2004;335(5):667-78. doi: 10.1016/j.jmb.2003.09.082.
Hall et al., Engineered Luciferase Reporter From a Deep Sea Shrimp Utilizing a Novel Imidazopyrazinone Substrate. ACS Chem Biol. Nov. 16, 2012;7(11):1848-57.
Koropatkin et al., How Glycan Metabolism Shapes the Human Gut Microbiota. Nat Rev Microbiol. Apr. 11, 2012;10(5):323-35. doi: 10.1038/nrmicro2746.
Kosuri et al., Composability of Regulatory Sequences Controlling Transcription and Translation in *Escherichia Coli*. PNAS USA. Aug. 20, 2013;110(34):14024-9. doi: 10.1073/pnas.1301301110.
Kotula et al., Programmable Bacteria Detect and Record an Environmental Signal in the Mammalian Gut. PNAS USA. Apr. 1, 2014;111(13):4838-43.
Lee et al., Bacterial Colonization Factors Control Specificity and Stability of the Gut Microbiota. Nature. Sep. 19, 2013;501(7467):426-9. doi:10.1038/nature12447.
Loessner et al., Complete Nucleotide Sequence, Molecular Analysis and Genome Structure of Bacteriophage A118 of Listeria Monocytogenes: Implications for Phage Evolution. Mol Micro. Jan. 2000;35(2):324-40. doi: 10.1046/j.1365-2958.2000.01720.x.
Lorbach et al., Site-specific recombination in human cells catalyzed by phage λ integrase mutants. J Mol Biol. Mar. 10, 2000;296(5):1175-81.
Martens et al., Recognition and Degradation of Plant Cell Wall Polysaccharides by Two Human Gut Symbionts. PLoS Biol. Dec. 20, 2011;9(12):e1001221, 16 pages.
Martens et al., Mucosal Glycan Foraging Enhances Fitness and Transmission of a Saccharolytic Human Gut Bacterial Symbiont. Cell Host Microbe. Nov. 13, 2008;4(5):447-57.
Mastropaolo et al., Comparison of Bacteroides thetaiotaomicron and *Escherichia coli* 16S rRNA gene expression signals. Microbiol. 2009;155:2683-93.
Matsuura et al., The sre gene (ORF469) encodes a site-specific recombinase responsible for integration of the R4 phage genome. J Bacteriol. Jun. 1996;178(11):3374-6.
Mutalik et al., Precise and Reliable Gene Expression via Standard Transcription and Translation Initiation Elements. Nat Methods. Apr. 2013;10(4):354-60. doi: 10.1038/nmeth.2404.
Ow et al., Conditionally replicating plasmid vectors that can integrate into the Klebsiella pneumoniae chromosome via bacteriophage P4 site-specific recombination. J Bacteriol. Aug. 1983;155(2):704-13.
Parker et al., Genetic and biochemical analysis of a novel Ambler class A beta-lactamase responsible for cefoxitin resistance in Bacteroides species. Antimicrob Agents Chemother. 1993;37:1028-36. doi: 10.1128/AAC.37.5.1028.
Patel et al., Rhamnose catabolism in Bacteroides thetaiotaomicron is controlled by the positive transcriptional regulator RhaR. Res Microbiol. Dec. 2008;159(9-10):678-84.
Qi et al., Repurposing CRISPR as an RNA-guided Platform for Sequence-Specific Control of Gene Expression. Cell. Feb. 28, 2013;152(5):1173-83.
Rogers et al., Insertional activation of cepA leads to high-level beta-lactamase expression in Bacteroides fragilis clinical isolates. J Bacteriol. 1994;176:4376-84.
Sakamoto et al., Reclassification of Bacteroides distasonis, Bacteroides goldsteinii and Bacteroides merdae as *Parabacteroides distasonis* gen. nov., comb, nov., *Parabacteroides goldsteinii* comb. nov. and *Parabacteroides merdae* comb. nov. Int J Syst Evol Microbiol. Jul. 2006; 56(7):1599-605.
Salis et al., Automated Design of Synthetic Ribosome Binding Sites to Control Protein Expression. Nat Biotechnol. Oct. 2009;27(10):946-50.
Salyers, Bacteroides of the Human Lower Intestinal Tract. Annu Rev Microbiol. 1984;38:293-313. doi: 10.1146/annurev.mi.38.100184.001453.
Sonnenburg et al., Specificity of Polysaccharide Use in Intestinal Bacteroides Species Determines Diet-Induced Microbiota Alterations. Cell. Jun. 25, 2010;141(7):1241-52.
Vingadassalom et al., An Unusual Primary Sigma Factor in the Bacteroidetes Phylum. Mol Microbiol. May 2005;56(4):888-902.
Wang et al., Characterization of a Bacteroides Mobilizable Transposon, NBU2, Which Carries a Functional Lincomycin Resistance Gene. J Bacteriol. Jun. 2000;182(12):3559-71. doi: 10.1128/jb.182.12.3559-3571.2000.
Wegmann et al., Defining the bacteroides ribosomal binding site. Appl Environ Microbiol. 2013;79:1980-9.
Yang et al., Permanent Genetic Memory With >1-byte Capacity. Nat Methods. Dec. 2014;11(12):1261-6. doi: 10.1038/nmeth.3147.
EP 16808336.8, European Exam Report, dated Oct. 23, 2020.
European Exam Report dated Oct. 23, 2020 for Application No. 16808336.8.
Feldhaus et al., Use of an *Escherichia coli* Beta-Glucuronidase Gene as a Reporter Gene for Investigation of Bacteroides Promoters. J Bacteriol. Jul. 1991;173(14):4540-3.

* cited by examiner

Figs. 2C
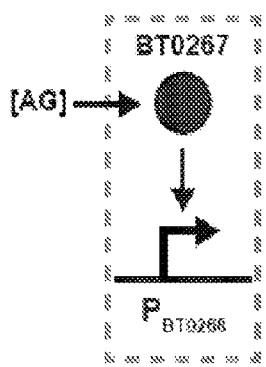 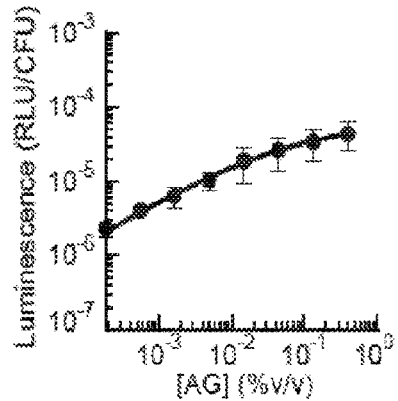
Fig. 2D
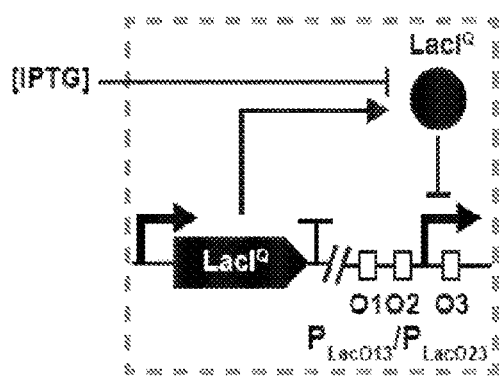 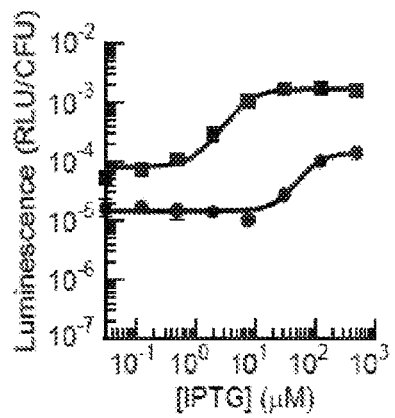
Fig. 2E
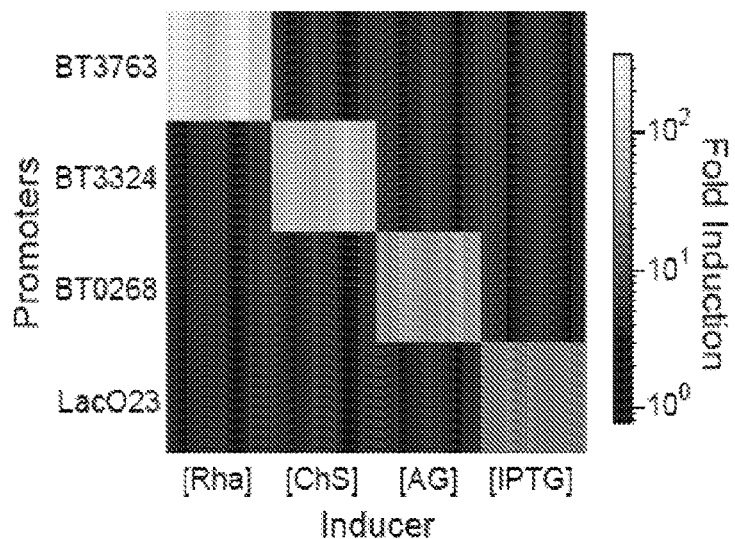

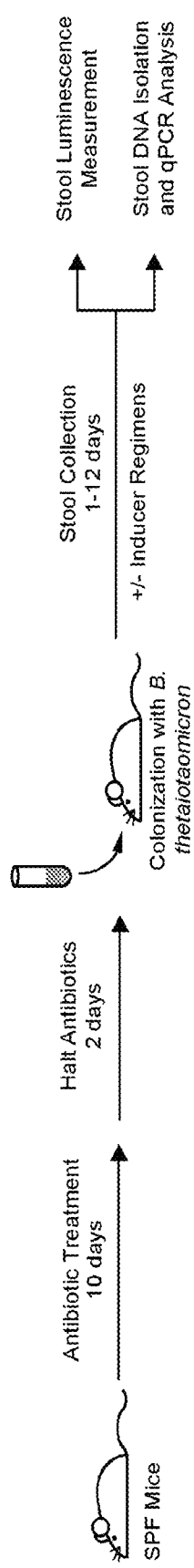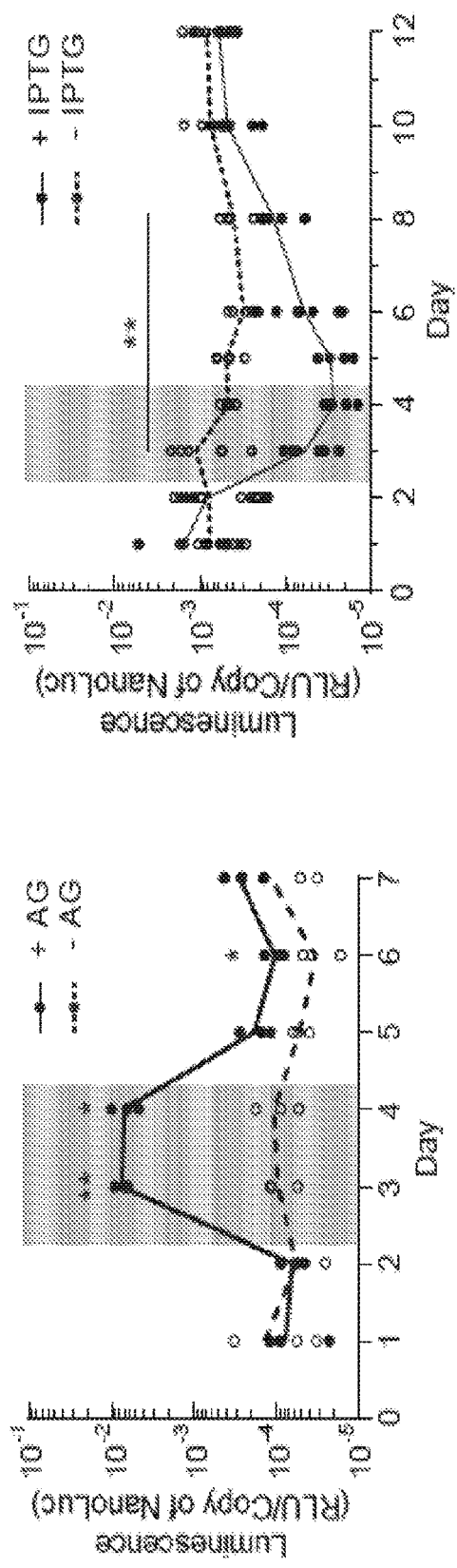
Fig. 5A
Fig. 5B
Fig. 5C

Fig. 6A

```
P_BT1311  GTTTTATTAGTTGAAAAAGTTGCCTAAATATGTATGTTAACAAATT
P_AM1     GCTTTGCAACAGCATAGCTCAGCACAGAAGTTGCCTAAATATGTTAACAAATT
P_AM2     GTTTTATTAGTTGAAAATAGTGAAAAAGTTGCCTAAATATGTTAACAAATT
P_AM3     GTTTTATTAGTTGAAAATAGTGAAAACTTGCAACAGCATAGCTCAGCACAGATT
P_AM4     GTTTTATTAGTTGAAAATAGTGAAAAAGTTGCCTAAATATGTTAACAAATT
```

-7                    +1
```
ATTTGTCGTAACTTT-----------GCACTCC---------AA
ATTTGTCGTAACTTT-----------GCACTCC---------AA
CTTTGCAACAGCATAGCTCAGCACAGGCACTCC---------AA
ATTTGTCGTAACTTT-----------GCACTCC---------AA
ATTTGTCGTAACTTT-----------GCACTCCCTTTGCAACAGCATAGCTCAGCACAGAAA
```

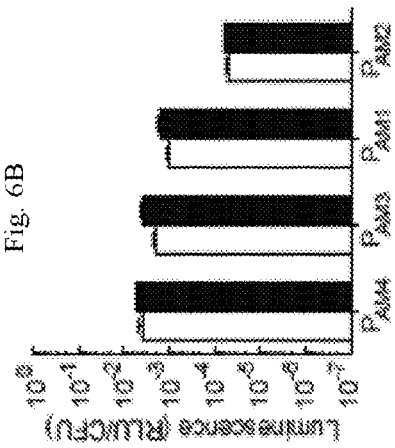

Fig. 6B

SEQUENCE LISTING

<160> NUMBER OF SEQ ID NOS: 220

<210> SEQ ID NO 1
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 1
tcccgcattt taaaataaaa taaattattc gtttagttaa acgaat    46

<210> SEQ ID NO 2
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 2
tcccgcattt taaaataaaa taaatgatat aattaattaa acgaat    46

<210> SEQ ID NO 3
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 3
tcccgcattt taaaataaaa taaataatat aattaattaa acgaat    46

<210> SEQ ID NO 4
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 4
tcccgcattt taaaataaaa taaataattt aattaattaa acgaat    46

<210> SEQ ID NO 5
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 5
tcccgcattt taaaataaaa taaattatat aattaattaa acgaat    46

<210> SEQ ID NO 6
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 6
tcccgcattt taaaataaaa taaataatat acttaattaa acgaat    46

<210> SEQ ID NO 7
<211> LENGTH: 46
<212> TYPE: DNA
<213> ORGANISM: Artificial Sequence

```
<220> FEATURE:
<223> OTHER INFORMATION: Synthetic Polynucleotide

<400> SEQUENCE: 7
tcccgcattt taaaataaaa taaattatta ttttaattaa acgaat          46

<210> SEQ ID NO 8
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 8
tcccgcattt taaaataaaa taaataatct acttaattaa acgaat          46

<210> SEQ ID NO 9
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 9
tcccgcattt taaaataaaa taaattattt aattaattaa acgaat          46

<210> SEQ ID NO 10
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 10
tcccgcattt taaaataaaa taaattatct aattaattaa acgaat          46

<210> SEQ ID NO 11
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 11
tcccgcattt taaaataaaa taaattattg atttagttaa acgaat          46

<210> SEQ ID NO 12
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 12
tcccgcattt taaaataaaa taaattatat atttaattaa acgaat          46

<210> SEQ ID NO 13
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 13
tcccgcattt taaaataaaa taaattatta ctttagttaa acgaat          46
```

```
<210> SEQ ID NO 14
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 14
tcccgcattt taaaataaaa taaattatta ctttaattaa acgaat            46

<210> SEQ ID NO 15
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 15
tcccgcattt taaaataaaa taaattattt ttttacttaa acgaat            46

<210> SEQ ID NO 16
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 16
tcccgcattt taaaataaaa taaattattt atttagttaa acgaat            46

<210> SEQ ID NO 17
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 17
tcccgcattt taaaataaaa taaattattc atttaattaa acgaat            46

<210> SEQ ID NO 18
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 18
tcccgcattt taaaataaaa taaataatgt aattaattaa acgaat            46

<210> SEQ ID NO 19
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 19
tcccgcattt taaaataaaa taaattatta atttagttaa acgaat            46

<210> SEQ ID NO 20
<211> LENGTH: 46
<212> TYPE: DNA
<213> ORGANISM: Artificial Sequence
<220> FEATURE:
<223> OTHER INFORMATION: Synthetic Polynucleotide
```

```
<400> SEQUENCE: 20
tcccgcattt taaaataaaa taaattatta atttacttaa acgaat          46

<210> SEQ ID NO 21
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 21
tcccgcattt taaaataaaa taaattattt atcgaattaa acgaat          46

<210> SEQ ID NO 22
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 22
tcccgcattt taaaataaaa taaataatat atttaattaa acgaat          46

<210> SEQ ID NO 23
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 23
tcccgcattt taaaataaaa taaattattg ctttaattaa acgaat          46

<210> SEQ ID NO 24
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 24
tcccgcattt taaaataaaa taaattatta gtttagttaa acgaat          46

<210> SEQ ID NO 25
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 25
tcccgcattt taaaataaaa taatgatttt aattaattaa acgaat          46

<210> SEQ ID NO 26
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 26
tcccgcattt taaaataaaa taaattatct atttaattaa acgaat          46
```

```
<210> SEQ ID NO 27
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 27
tcccgcattt taaaataaaa taaatgattt acttaattaa acgaat            46

<210> SEQ ID NO 28
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 28
tcccgcattt taaaataaaa taaattatat acttaattaa acgaat            46

<210> SEQ ID NO 29
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 29
tcccgcattt taaaataaaa taaattatta atttaattaa acgaat            46

<210> SEQ ID NO 30
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 30
tcccgcattt taaaataaaa taaataattt agttaattaa acgaat            46

<210> SEQ ID NO 31
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 31
tcccgcattt taaaataaaa taaattatta ttttaattaa acgaat            46

<210> SEQ ID NO 32
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 32
tcccgcattt taaaataaaa taaattattt ctttacttaa acgaat            46

<210> SEQ ID NO 33
<211> LENGTH: 46
<212> TYPE: DNA
<213> ORGANISM: Artificial Sequence
<220> FEATURE:
<223> OTHER INFORMATION: Synthetic Polynucleotide
```

<400> SEQUENCE: 33
tcccgcattt taaaataaaa taaattattt ctttaattaa acgaat                46

<210> SEQ ID NO 34
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 34
tcccgcattt taaaataaaa taaattatta gtttaattaa acgaat                46

<210> SEQ ID NO 35
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 35
tcccgcattt taaaataaaa taaataatgt agttaattaa acgaat                46

<210> SEQ ID NO 36
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 36
tcccgcattt taaaataaaa taaattattt ttttacttaa acgaat                46

<210> SEQ ID NO 37
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 37
tcccgcattt taaaataaaa taaattatta gtttagttaa acgaat                46

<210> SEQ ID NO 38
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 38
tcccgcattt taaaataaaa taaattatta atttaattaa acgaat                46

<210> SEQ ID NO 39
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 39
tcccgcattt taaaataaaa taaattattt atttaattaa acgaat                46

```
<210> SEQ ID NO 40
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 40
tcccgcattt taaaataaaa taaattattt ctttacttaa acgaat         46

<210> SEQ ID NO 41
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 41
tcccgcattt taaaataaaa taaattattt ctttaattaa acgaat         46

<210> SEQ ID NO 42
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 42
tcccgcattt taaaataaaa taaattatgt atttaattaa acgaat         46

<210> SEQ ID NO 43
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 43
tcccgcattt taaaataaaa taaattatta gtttaattaa acgaat         46

<210> SEQ ID NO 44
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 44
tcccgcattt taaaataaaa taaattatta gtttatttaa acgaat         46

<210> SEQ ID NO 45
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 45
tcccgcattt taaaataaaa taaattatta gtttatttaa acgaat         46

<210> SEQ ID NO 46
<211> LENGTH: 46
<212> TYPE: DNA
<213> ORGANISM: Artificial Sequence
<220> FEATURE:
<223> OTHER INFORMATION: Synthetic Polynucleotide
```

<400> SEQUENCE: 46
tcccgcattt taaaataaaa taaattattg ttttacttaa acgaat        46

<210> SEQ ID NO 47
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 47
tcccgcattt taaaataaaa taaattattg ttttacttaa acgaat        46

<210> SEQ ID NO 48
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 48
tcccgcattt taaaataaaa taaattattg ctttagttaa acgaat        46

<210> SEQ ID NO 49
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 49
tcccgcattt taaaataaaa taaattattg ctttagttaa acgaat        46

<210> SEQ ID NO 50
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 50
tcccgcattt taaaataaaa taaattattg gtttaattaa acgaat        46

<210> SEQ ID NO 51
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 51
tcccgcattt taaaataaaa taaattattg ttttagttaa acgaat        46

<210> SEQ ID NO 52
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 52
tcccgcattt taaaataaaa taaatgatct aattaattaa acgaat        46

<210> SEQ ID NO 53
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 53
tcccgcattt taaaataaaa taaatgatat atttaattaa acgaat    46

<210> SEQ ID NO 54
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 54
tcccgcattt taaaataaaa taaattattg gtttaattaa acgaat    46

<210> SEQ ID NO 55
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 55
tcccgcattt taaaataaaa taaatcatgt aattaattaa acgaat    46

<210> SEQ ID NO 56
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 56
tcccgcattt taaaataaaa taaattattg ttttaattaa acgaat    46

<210> SEQ ID NO 57
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 57
tcccgcattt taaaataaaa taaattattg ttttaattaa acgaat    46

<210> SEQ ID NO 58
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 58
tcccgcattt taaaataaaa taaattattg atttacttaa acgaat    46

<210> SEQ ID NO 59
<211> LENGTH: 46
<212> TYPE: DNA
<213> ORGANISM: Artificial Sequence
<220> FEATURE:
<223> OTHER INFORMATION: Synthetic Polynucleotide -continued

<400> SEQUENCE: 59
tcccgcattt taaaataaaa taaattattt ctttatttaa acgaat     46

<210> SEQ ID NO 60
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 60
tcccgcattt taaaataaaa taaattattg atttacttaa acgaat     46

<210> SEQ ID NO 61
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 61
tcccgcattt taaaataaaa taaataatct atttaattaa acgaat     46

<210> SEQ ID NO 62
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 62
tcccgcattt taaaataaaa taaatcattt atttaattaa acgaat     46

<210> SEQ ID NO 63
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 63
tcccgcattt taaaataaaa taaatgattt agttaattaa acgaat     46

<210> SEQ ID NO 64
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 64
tcccgcattt taaaataaaa taaattatta ttttacttaa acgaat     46

<210> SEQ ID NO 65
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 65
tcccgcattt taaaataaaa taaattattt atttacttaa acgaat     46

```
<210> SEQ ID NO 66
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 66
tcccgcattt taaaataaaa taaattattt ttttagttaa acgaat          46

<210> SEQ ID NO 67
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 67
tcccgcattt taaaataaaa taaattattt ctttatttaa acgaat          46

<210> SEQ ID NO 68
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 68
tcccgcattt taaaataaaa taaattattt agttaattaa acgaat          46

<210> SEQ ID NO 69
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 69
tcccgcattt taaaataaaa taaattattc atttatttaa acgaat          46

<210> SEQ ID NO 70
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 70
tcccgcattt taaaataaaa taaattattt ttttatttaa acgaat          46

<210> SEQ ID NO 71
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 71
tcccgcattt taaaataaaa taaattattt atttatttaa acgaat          46

<210> SEQ ID NO 72
<211> LENGTH: 46
<212> TYPE: DNA
<213> ORGANISM: Artificial Sequence
<220> FEATURE:
<223> OTHER INFORMATION: Synthetic Polynucleotide
```

<400> SEQUENCE: 72
tcccgcattt taaaataaaa taaattatta ttttacttaa acgaat        46

<210> SEQ ID NO 73
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 73
tcccgcattt taaaataaaa taaattattt atttacttaa acgaat        46

<210> SEQ ID NO 74
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 74
tcccgcattt taaaataaaa taaatgatat agttaattaa acgaat        46

<210> SEQ ID NO 75
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 75
tcccgcattt taaaataaaa taaattattt atttacttaa acgaat        46

<210> SEQ ID NO 76
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 76
tcccgcattt taaaataaaa taaattattt ttttagttaa acgaat        46

<210> SEQ ID NO 77
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 77
tcccgcattt taaaataaaa taaattatgt agttaattaa acgaat        46

<210> SEQ ID NO 78
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 78
tcccgcattt taaaataaaa taaattattg ctttatttaa acgaat        46

<210> SEQ ID NO 79
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 79
tcccgcattt taaaataaaa taaattatta gtttacttaa acgaat         46

<210> SEQ ID NO 80
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 80
tcccgcattt taaaataaaa taaattatat agttaattaa acgaat         46

<210> SEQ ID NO 81
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 81
tcccgcattt taaaataaaa taaattattc atttatttaa acgaat         46

<210> SEQ ID NO 82
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 82
tcccgcattt taaaataaaa taaatgatgt atttaattaa acgaat         46

<210> SEQ ID NO 83
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 83
tcccgcattt taaaataaaa taaattattc ttttacttaa acgaat         46

<210> SEQ ID NO 84
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 84
tcccgcattt taaaataaaa taaattattc ctttaattaa acgaat         46

<210> SEQ ID NO 85
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 85
tcccgcattt taaaataaaa taaatgatct agttaattaa acgaat          46

<210> SEQ ID NO 86
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 86
tcccgcattt taaaataaaa taaattattt ttttatttaa acgaat          46

<210> SEQ ID NO 87
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 87
tcccgcattt taaaataaaa taaattatta ctttatttaa acgaat          46

<210> SEQ ID NO 88
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 88
tcccgcattt taaaataaaa taaattattt atttatttaa acgaat          46

<210> SEQ ID NO 89
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 89
tcccgcattt taaaataaaa taaattattg gtttagttaa acgaat          46

<210> SEQ ID NO 90
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 90
tcccgcattt taaaataaaa taaattattt atttacttaa acgaat          46

<210> SEQ ID NO 91
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 91
tcccgcattt taaaataaaa taaattattg ctttatttaa acgaat          46

<210> SEQ ID NO 92
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 92
tcccgcattt taaaataaaa taaatgatgt agttaattaa acgaat        46

<210> SEQ ID NO 93
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 93
tcccgcattt taaaataaaa taaattatta gtttacttaa acgaat        46

<210> SEQ ID NO 94
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 94
tcccgcattt taaaataaaa taaattattc ttttatttaa acgaat        46

<210> SEQ ID NO 95
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 95
tcccgcattt taaaataaaa taaattattc ctttatttaa acgaat        46

<210> SEQ ID NO 96
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 96
tcccgcattt taaaataaaa taaattattc ttttacttaa acgaat        46

<210> SEQ ID NO 97
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 97
tcccgcattt taaaataaaa taaatcatgt atttaattaa acgaat        46

<210> SEQ ID NO 98
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 98
tcccgcattt taaaataaaa taaatcatct atttaattaa acgaat      46

<210> SEQ ID NO 99
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 99
tcccgcattt taaaataaaa taaattattc ctttaattaa acgaat      46

<210> SEQ ID NO 100
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 100
tcccgcattt taaaataaaa taaattatta ctttatttaa acgaat      46

<210> SEQ ID NO 101
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 101
tcccgcattt taaaataaaa taaattattc ctttacttaa acgaat      46

<210> SEQ ID NO 102
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 102
tcccgcattt taaaataaaa taaattattg gtttagttaa acgaat      46

<210> SEQ ID NO 103
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 103
tcccgcattt taaaataaaa taaattattg gtttatttaa acgaat      46

<210> SEQ ID NO 104
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 104
tcccgcattt taaaataaaa taaattattc ttttagttaa acgaat      46

```
<210> SEQ ID NO 105
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 105
tcccgcattt taaaataaaa taaatcatgt acttaattaa acgaat            46

<210> SEQ ID NO 106
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 106
tcccgcattt taaaataaaa taaattattt ctttagttaa acgaat            46

<210> SEQ ID NO 107
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 107
tcccgcattt taaaataaaa taaattattt gtttacttaa acgaat            46

<210> SEQ ID NO 108
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 108
tcccgcattt taaaataaaa taaattattc ttttatttaa acgaat            46

<210> SEQ ID NO 109
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 109
tcccgcattt taaaataaaa taaattattc ctttatttaa acgaat            46

<210> SEQ ID NO 110
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 110
tcccgcattt taaaataaaa taaattattc atttagttaa acgaat            46

<210> SEQ ID NO 111
<211> LENGTH: 46
<212> TYPE: DNA
<213> ORGANISM: Artificial Sequence
<220> FEATURE:
<223> OTHER INFORMATION: Synthetic Polynucleotide
```

<400> SEQUENCE: 111
tcccgcattt taaaataaaa taaattattt gtttagttaa acgaat        46

<210> SEQ ID NO 112
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 112
tcccgcattt taaaataaaa taaatcatat aattaattaa acgaat        46

<210> SEQ ID NO 113
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 113
tcccgcattt taaaataaaa taaattattt gtttaattaa acgaat        46

<210> SEQ ID NO 114
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 114
tcccgcattt taaaataaaa taaattattc ctttagttaa acgaat        46

<210> SEQ ID NO 115
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 115
tcccgcattt taaaataaaa taaattattc ctttacttaa acgaat        46

<210> SEQ ID NO 116
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 116
tcccgcattt taaaataaaa taaattattg ttttatttaa acgaat        46

<210> SEQ ID NO 117
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 117
tcccgcattt taaaataaaa taaattattg gtttatttaa acgaat        46

```
<210> SEQ ID NO 118
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 118
tcccgcattt taaaataaaa taaattattt gtttatttaa acgaat              46

<210> SEQ ID NO 119
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 119
tcccgcattt taaaataaaa taaattattc ttttagttaa acgaat              46

<210> SEQ ID NO 120
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 120
tcccgcattt taaaataaaa taaattattt ctttagttaa acgaat              46

<210> SEQ ID NO 121
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 121
tcccgcattt taaaataaaa taaatcatat atttaattaa acgaat              46

<210> SEQ ID NO 122
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 122
tcccgcattt taaaataaaa taaattattt gtttacttaa acgaat              46

<210> SEQ ID NO 123
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 123
tcccgcattt taaaataaaa taaattatta ttttatttaa acgaat              46

<210> SEQ ID NO 124
<211> LENGTH: 46
<212> TYPE: DNA
<213> ORGANISM: Artificial Sequence
<220> FEATURE:
<223> OTHER INFORMATION: Synthetic Polynucleotide
```

```
<400> SEQUENCE: 124
tcccgcattt taaaataaaa taaattattc atttagttaa acgaat             46

<210> SEQ ID NO 125
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 125
tcccgcattt taaaataaaa taaattattt gtttagttaa acgaat             46

<210> SEQ ID NO 126
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 126
tcccgcattt taaaataaaa taaattattt gtttaattaa acgaat             46

<210> SEQ ID NO 127
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 127
tcccgcattt taaaataaaa taaatcattt agttaattaa acgaat             46

<210> SEQ ID NO 128
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 128
tcccgcattt taaaataaaa taaattattc ctttagttaa acgaat             46

<210> SEQ ID NO 129
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 129
tcccgcattt taaaataaaa taaattattg ttttatttaa acgaat             46

<210> SEQ ID NO 130
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 130
tcccgcattt taaaataaaa taaattattg gtttacttaa acgaat             46
```

```
<210> SEQ ID NO 131
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 131
tcccgcattt taaaataaaa taaattattc gtttaattaa acgaat            46

<210> SEQ ID NO 132
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 132
tcccgcattt taaaataaaa taaattattt gtttatttaa acgaat            46

<210> SEQ ID NO 133
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 133
tcccgcattt taaaataaaa taaatcatct agttaattaa acgaat            46

<210> SEQ ID NO 134
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 134
tcccgcattt taaaataaaa taaatcatgt agttaattaa acgaat            46

<210> SEQ ID NO 135
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 135
tcccgcattt taaaataaaa taaattattc gtttatttaa acgaat            46

<210> SEQ ID NO 136
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 136
tcccgcattt taaaataaaa taaattatta ttttatttaa acgaat            46

<210> SEQ ID NO 137
<211> LENGTH: 46
<212> TYPE: DNA
<213> ORGANISM: Artificial Sequence
<220> FEATURE:
<223> OTHER INFORMATION: Synthetic Polynucleotide
```

<400> SEQUENCE: 137
tcccgcattt taaaataaaa taaattattc gtttacttaa acgaat          46

<210> SEQ ID NO 138
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 138
tcccgcattt taaaataaaa taaattattg gtttacttaa acgaat          46

<210> SEQ ID NO 139
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 139
tcccgcattt taaaataaaa taaatcatat agttaattaa acgaat          46

<210> SEQ ID NO 140
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 140
tcccgcattt taaaataaaa taaattattc gtttaattaa acgaat          46

<210> SEQ ID NO 141
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 141
tcccgcattt taaaataaaa taaattattc gtttatttaa acgaat          46

<210> SEQ ID NO 142
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 142
tcccgcattt taaaataaaa taaattattc gtttacttaa acgaat          46

<210> SEQ ID NO 143
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 143
tcccgcattt taaaataaaa taaattattc gtttagttaa acgaat          46

<210> SEQ ID NO 144
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 144

```
tatttcggag aaaacatgca taaatcatgc ttttttttgca taaaaagtaa aatttatact      60
gatgtaaggt ttggctatgc agatttgtgt caaaatgcac atcctttcta tcaaaatgcg     120
taaggaaaag gaggaaggaa ccgcctatct ttgcaatgta ggtaaatgga taccttaaat     180
atatagacaa aatacc                                                    196
```

<210> SEQ ID NO 145
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 145

```
tatttataag agatagcaca taatttgaac tattttgtac gatttgaacc cctctttcca      60
acaaaagagg ggtttctttg cattcgggag aagaacaagt gatctctctc tgtaaatacc     120
ggctaatgat aaaccgattt accatcggac ctaaaacgat atattctatg ataaagcaat     180
cttttactct gtcagtgaca                                                200
```

<210> SEQ ID NO 146
<211> LENGTH: 255
<212> TYPE: DNA
<213> ORGANISM: Artificial Sequence
<220> FEATURE:
<223> OTHER INFORMATION: Synthetic Polynucleotide

<400> SEQUENCE: 146

```
taaaatacac aagtacgcgt cttaatggaa gatgcgtact tttccatata tcaatgatct      60
atcccatttg aatgattcct gaacttatat tgaacgattt ttagacctgt tatagttaat     120
agcgattatg gtccaatttt ggaagttttt gaatgattag agaacttctt tctactggat     180
aactcgcact tttgtgacgc atttgatgca caactaatac ttatttggtc taaataactt     240
tataaatcta atagt                                                     255
```

<210> SEQ ID NO 147
<211> LENGTH: 141
<212> TYPE: DNA
<213> ORGANISM: Artificial Sequence
<220> FEATURE:
<223> OTHER INFORMATION: Synthetic Polynucleotide

<400> SEQUENCE: 147

```
ttacaaagaa aattcgacaa actgttattt ttctatctat ttaaattgtg agcggataac      60
aatttgaatt gtgagcggat aacaattacc tttgtcggca aataaagata ttctcgtcaa     120
acaaatataa ataatataaa c                                              141
```

<210> SEQ ID NO 148
<211> LENGTH: 162
<212> TYPE: DNA
<213> ORGANISM: Artificial Sequence
<220> FEATURE:
<223> OTHER INFORMATION: Synthetic Polynucleotide

<400> SEQUENCE: 148

```
ttacaaagaa aattcgacaa actgttattt ttctatctat ttaaattgtg agcggataac    60
aatttgggtg ggaaacttta gttatgtacc tttgtcggca attgtgagcg ataacaatt   120
aaataaagat attctcgtca acaaatata aataatataa ac                      162
```

<210> SEQ ID NO 149
<211> LENGTH: 143
<212> TYPE: DNA
<213> ORGANISM: Artificial Sequence
<220> FEATURE:
<223> OTHER INFORMATION: Synthetic Polynucleotide

<400> SEQUENCE: 149

```
ttacaaagaa aattcgacaa actgttattt ttctatctat ttatttgaat tgtgagcgga    60
taacaattac ctttgtcggc aattgtgagc ggataacaat taaataaaga tattctcgtc   120
aaacaaatat aaataatata aac                                          143
```

<210> SEQ ID NO 150
<211> LENGTH: 1092
<212> TYPE: DNA
<213> ORGANISM: Artificial Sequence
<220> FEATURE:
<223> OTHER INFORMATION: Synthetic Polynucleotide

<400> SEQUENCE: 150

```
gtggtgaatg tgaaaccagt aacgttatac gatgtcgcag agtatgccgg tgtctcttat    60
cagaccgttt cccgcgtggt gaaccaggcc agccacgttt ctgcgaaaac gcgggaaaaa   120
gtggaagcgg cgatggcgga gctgaattac attcccaacc gcgtggcaca acaactggcg   180
ggcaaacagt cgttgctgat tggcgttgcc acctccagtc tggccctgca cgcgccgtcg   240
caaattgtcg cggcgattaa atctcgcgcc gatcaactgg gtgccagcgt ggtggtgtcg   300
atggtagaac gaagcggcgt cgaagcctgt aaagcggcgg tgcacaatct tctcgcgcaa   360
cgcgtcagtg ggctgatcat taactatccg ctggatgacc aggatgccat tgctgtggaa   420
gctgcctgca ctaatgttcc ggcgttattt cttgatgtct ctgaccagac acccatcaac   480
agtattattt tctcccatga ggacggtacg cgactgggcg tggagcatct ggtcgcattg   540
ggtcaccagc aaatcgcgct gttagcgggc ccattaagtt ctgtctcggc gcgtctgcgt   600
ctggctggct ggcataaata tctcactcgc aatcaaattc agccgatagc ggaacgggaa   660
ggcgactgga gtgccatgtc cggttttcaa caaaccatgc aaatgctgaa tgagggcatc   720
gttcccactg cgatgctggt tgccaacgat cagatggcgc tgggcgcaat gcgcgccatt   780
accgagtccg gctgcgcgt tggtgcggat atctcggtag tgggatacga cgataccgag   840
gacagctcat gttatatccc gccgttaacc accatcaaac aggattttcg cctgctgggg   900
caaaccagcg tggaccgctt gctgcaactc tctcagggcc aggcggtgaa gggcaatcag   960
ctgttgcccg tctcactggt gaaaagaaaa accaccctgg cgcccaatac gcaaaccgcc  1020
tctccccgcg cgttggccga ttcattaatg cagctggcac acaggtttc ccgactggaa  1080
agcgggcagt ga                                                     1092
```

<210> SEQ ID NO 151
<211> LENGTH: 122
<212> TYPE: DNA
<213> ORGANISM: Artificial Sequence
<220> FEATURE:
<223> OTHER INFORMATION: Synthetic Polynucleotide

```
<400> SEQUENCE: 151
ttacaaagaa aattcgacaa actgttattt ttctatctat ttatttgggt gggaaacttt      60
agttatgtac ctttgtcggc aaataaagat attctcgtca aacaaatata aataatataa     120
ac                                                                    122

<210> SEQ ID NO 152
<211> LENGTH: 309
<212> TYPE: DNA
<213> ORGANISM: Artificial Sequence
<220> FEATURE:
<223> OTHER INFORMATION: Synthetic Polynucleotide

<400> SEQUENCE: 152
tgatctggaa gaagcaatga aagctgctgt taagtctccg aatcaggtat tgttcctgac      60
aggtgtattc ccatccggta aacgcggata ctttgcagtt gatctgactc aggaataaat     120
tataaattaa ggtaagaaga ttgtaggata agctaatgaa atagaaaaag gatgccgtca     180
cacaacttgt cggcattctt tttttgttta ttagttgaaa atatagtgaa aaagttgcct     240
aaatatgtat gttaacaaat tatttgtcgt aactttgcac tccaaatctg tttttaacat     300
atggcacta                                                             309

<210> SEQ ID NO 153
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 153
gataaagttt ggaagataaa gctaaaagtt cttatctttg cagtccgaaa taaagacata      60
taaaagaaaa gacacc                                                     76

<210> SEQ ID NO 154
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 154
ggagtgagct tctcggattt tatttgtatt tttgccatgc ctgatgaggt tttgtttgat      60 tattttttg caacactaag ttaagtgaat cctctgacat ggcaaaatcc tgagcaactt     120
tttgttgctc aggtacttaa aaaaaatatt ttataatagt gttgcggaat taaggtaaaa     180
gaataaa                                                               187

<210> SEQ ID NO 155
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 155
caaatttgcg cgccacaatt attattcata cctttgtgga ccgtattaca aagaacccaa      60
tcatat                                                                66
```

<210> SEQ ID NO 156
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 156

| gataaagttt ggaagataaa gctaaaagtt cttatctttg cagt | 44 |
|---|---|

<210> SEQ ID NO 157
<211> LENGTH: 4107
<212> TYPE: DNA
<213> ORGANISM: Artificial Sequence
<220> FEATURE:
<223> OTHER INFORMATION: Synthetic Polynucleotide

<400> SEQUENCE: 157

| atggataaga aatactcaat aggcttagct atcggcacaa atagcgtcgg atgggcggtg | 60 |
|---|---|
| atcactgatg aatataaggt tccgtctaaa aagttcaagg ttctgggaaa tacagaccgc | 120 |
| cacagtatca aaaaaatct tatagggget cttttatttg acagtggaga dacagcggaa | 180 |
| gcgactcgtc tcaaacggac agctcgtaga aggtatacac gtcggaagaa tcgtatttgt | 240 |
| tatctacagg agatttttc aaatgagatg gcgaaagtag atgatagttt ctttcatcga | 300 |
| cttgaagagt cttttttggt ggaagaagac aagaagcatg aacgtcatcc tattttggga | 360 |
| aatatagtag atgaagttgc ttatcatgag aaatatccaa ctatctatca tctgcgaaaa | 420 |
| aaattggtag attctactga taaagcggat ttgcgcttaa tctatttggc cttagcgcat | 480 |
| atgattaagt tcgtggtca ttttttgatt gagggagatt taaatcctga taatagtgat | 540 |
| gtggacaaac tatttatcca gttggtacaa acctacaatc aattatttga agaaaaccct | 600 |
| attaacgcaa gtggagtaga tgctaaagcg attcttctg cacgattgag taaatcaaga | 660 |
| cgattagaaa atctcattgc tcagctcccc ggtgagaaga aaatggctt atttgggaat | 720 |
| ctcattgctt tgtcattggg tttgacccct aattttaaat caaattttga tttggcagaa | 780 |
| gatgctaaat tacagctttc aaaagatact tacgatgatg atttagataa tttattggcg | 840 |
| caaattggag atcaatatgc tgatttgttt ttggcagcta agaatttatc agatgctatt | 900 |
| ttactttcag atatcctaag agtaaatact gaaataacta aggctcccct atcagcttca | 960 |
| atgattaaac gctacgatga acatcatcaa gacttgactc ttttaaaagc tttagttcga | 1020 |
| caacaacttc cagaaaagta taaagaaatc tttttgate aatcaaaaaa cggatatgca | 1080 |
| ggttatattg atggggagc tagccaagaa gaattttata atttatcaa accaatttta | 1140 |
| gaaaaaatgg atggtactga ggaattattg gtgaaactaa atcgtgaaga tttgctgcgc | 1200 |
| aagcaacgga cctttgacaa cggctctatt ccccatcaaa ttcacttggg tgagctgcat | 1260 |
| gctattttga gaagacaaga agactttat ccatttttaa aagacaatcg tgaagaagatt | 1320 |
| gaaaaaatct tgactttcg aattccttat tatgttggtc cattggcgcg tggcaatagt | 1380 |
| cgttttgcat ggatgactcg gaagtctgaa gaaacaatta ccccatggaa ttttgaagaa | 1440 |
| gttgtcgata aggtgcttc agctcaatca tttattgaac gcatgacaaa ctttgataaa | 1500 |
| aatcttccaa atgaaaaagt actaccaaaa catagtttgc tttatgagta ttttacggtt | 1560 |
| tataacgaat tgacaaaggt caaatatgtt actgaaggaa tgcgaaaacc agcatttctt | 1620 |
| tcaggtgaac agaagaaagc cattgttgat ttactcttca aaacaaatcg aaaagtaacc | 1680 |
| gttaagcaat taaaagaaga ttatttcaaa aaaatagaat gttttgatag tgttgaaatt | 1740 |

```
tcaggagttg aagatagatt taatgcttca ttaggtacct accatgattt gctaaaaatt    1800
attaaagata aagattttt ggataatgaa gaaaatgaag atatcttaga ggatattgtt    1860
ttaacattga ccttatttga agatagggag atgattgagg aaagacttaa aacatatgct    1920
cacctctttg atgataaggt gatgaaacag cttaaacgtc gccgttatac tggttgggga    1980
cgtttgtctc gaaaattgat taatggtatt agggataagc aatctggcaa aacaatatta    2040
gattttttga aatcagatgg ttttgccaat cgcaatttta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaggtat tttacagact     2220
gtaaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatgcc    2520
attgttccac aaagttttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat     2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060
atgattgcta agtctgagca agaaataggc aaagcaaccg caaatatttt ctttttactct    3120
aatatcatga acttcttcaa aacagaaatt acacttgcaa atggagagat tcgcaaacgc    3180
cctctaatcg aaactaatgg ggaaactgga gaaattgtct gggataaagg gcagatttt     3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtgaa aaagggaaat cgaagaagtt aaaatccgtt     3480
aaagagttac tagggatcac aattatggaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaatttc taagcgtgtt     3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa     4020
gaagtttag atgccactct tatccatcaa tccatcactg gtctttatga aacacgcatt     4080
gatttgagtc agctaggagg tgactga                                        4107
```

<210> SEQ ID NO 158
<211> LENGTH: 102
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: n is a, c, g, or t

<400> SEQUENCE: 158
nnnnnnnnnn nnnnnnnnnn gttttagagc tagaaatagc aagttaaaat aaggctagtc     60
cgttatcaac ttgaaaaagt ggcaccgagt cggtgctttt tt                        102

<210> SEQ ID NO 159
<211> LENGTH: 516
<212> TYPE: DNA
<213> ORGANISM: Artificial Sequence
<220> FEATURE:
<223> OTHER INFORMATION: Synthetic Polynucleotide

<400> SEQUENCE: 159
atggttttta ctctggaaga ttttgttggc gattggcgtc agaccgcggg ttataatttg     60
gatcaagtcc tggaacaggg tggcgtaagc tctctgttcc agaacctggg tgtgagcgtg    120
acgccgattc agcgcatcgt tctgtccggc gagaacggtc tgaaaattga tattcatgtg    180
atcatcccgt acgaaggcct gagcggtgac caaatgggtc aaatcgagaa aatctttaaa    240
gtcgtctacc cagttgacga tcaccacttc aaggttatct tgcattacgg tacgctggtg    300
attgatggtg tgaccccgaa tatgattgac tatttcggcc gtccgtatga aggcattgcc    360 gttttttgacg gtaaaaagat caccgtcacc ggtaccctgt ggaatggcaa taagattatt    420
gacgagcgtc tgattaaccc ggacggcagc ctgctgttcc gcgtgaccat caacggtgtc    480
acgggttggc gtctgtgcga gcgcatcctg cataa                               516

<210> SEQ ID NO 160
<211> LENGTH: 309
<212> TYPE: DNA
<213> ORGANISM: Artificial Sequence
<220> FEATURE:
<223> OTHER INFORMATION: Synthetic Polynucleotide

<400> SEQUENCE: 160
tgatctggaa gaagcaatga aagctgctgt taagtctccg aatcaggtat tgttcctgac     60
aggtgtattc ccatccggta acgcggata ctttgcagtt gatctgactc aggaataaat     120
tataaattaa ggtaagaaga ttgtaggata agctaatgaa atagaaaaag gatgccgtca    180
cacaacttgt cggcattctt ttttgctttg caacagcata gctcagcaca gaagttgcct    240
aaatatgtat gttaacaaat tatttgtcgt aactttgcac tccaaatctg tttttaacat    300
atggcacta                                                            309

<210> SEQ ID NO 161
<211> LENGTH: 320
<212> TYPE: DNA
<213> ORGANISM: Artificial Sequence
<220> FEATURE:
<223> OTHER INFORMATION: Synthetic Polynucleotide

<400> SEQUENCE: 161

```
tgatctggaa gaagcaatga aagctgctgt taagtctccg aatcaggtat tgttcctgac    60
aggtgtattc ccatccggta aacgcggata ctttgcagtt gatctgactc aggaataaat   120
tataaattaa ggtaagaaga ttgtaggata agctaatgaa atagaaaaag gatgccgtca   180
cacaacttgt cggcattctt ttttgtttta ttagttgaaa atatagtgaa aaagttgcct   240
aaatatgtat gttaacaaat tctttgcaac agcatagctc agcacaggca ctccaaatct   300
gtttttaaca tatggcacta                                               320
```

<210> SEQ ID NO 162
<211> LENGTH: 309
<212> TYPE: DNA
<213> ORGANISM: Artificial Sequence
<220> FEATURE:
<223> OTHER INFORMATION: Synthetic Polynucleotide

<400> SEQUENCE: 162

```
tgatctggaa gaagcaatga aagctgctgt taagtctccg aatcaggtat tgttcctgac    60
aggtgtattc ccatccggta aacgcggata ctttgcagtt gatctgactc aggaataaat   120
tataaattaa ggtaagaaga ttgtaggata agctaatgaa atagaaaaag gatgccgtca   180
cacaacttgt cggcattctt ttttgtttta ttagttgaaa atatagtgaa aactttgcaa   240
cagcatagct cagcacagat tatttgtcgt aactttgcac tccaaatctg tttttaacat   300
atggcacta                                                           309
```

<210> SEQ ID NO 163
<211> LENGTH: 326
<212> TYPE: DNA
<213> ORGANISM: Artificial Sequence
<220> FEATURE:
<223> OTHER INFORMATION: Synthetic Polynucleotide

<400> SEQUENCE: 163

```
tgatctggaa gaagcaatga aagctgctgt taagtctccg aatcaggtat tgttcctgac    60
aggtgtattc ccatccggta aacgcggata ctttgcagtt gatctgactc aggaataaat   120
tataaattaa ggtaagaaga ttgtaggata agctaatgaa atagaaaaag gatgccgtca   180
cacaacttgt cggcattctt ttttgtttta ttagttgaaa atatagtgaa aaagttgcct   240
aaatatgtat gttaacaaat tatttgtcgt aactttgcac tcccttttgca acagcatagc   300
tcagcacaga atctgttttt taacat                                        326
```

<210> SEQ ID NO 164
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 164

```
atgaaagtgg ccatttatgt tcgtgttagc accgatgaac aggccaaaga aggttttagc    60
attccggcac agcgtgaacg tctgcgtgca ttttgtgcaa gccagggttg ggaaattgtg   120
caagaatata ttgaagaagg ttggagcgca aaagatctgg atcgtccgca gatgcagcgt   180
ctgctgaaag atatcaaaaa aggcaacatt gatattgtgc tggtgtatcg tctggatcgc   240
ctgacccgta gcgttctgga tctgtatctg ctgctgcaga cctttgaaaa atacaatgtg   300
gcatttcgta gcgccaccga gtttatgat accagcaccg caatgggtcg tctgtttatt   360
```

| | |
|---|---|
| accctggttg cagcactggc acagtgggaa cgtgaaaatc tggcagaacg tgttaaattt | 420 |
| ggtatcgagc agatgatcga tgaaggtaaa aaaccgggtg gtcatagccc gtatggttac | 480 |
| aaatttgata agacttcaa ttgcaccatt attgaggaag aagcagacgt tgttcgtatg | 540 |
| atctatcgca tgtattgtga tggttatggc tatcgtagca ttgcagatcg tctgaatgaa | 600 |
| ctgatggtta aaccgcgtat tgccaaagaa tggaatcata atagcgtgcg tgatatcctg | 660 |
| accaacgata tctatattgg cacctatcgt tggggtgata agttgttcc gaataatcat | 720 |
| ccgcctatta ttagcgaaac cctgttcaaa aaagcccaga agaaaaaga aaacgtggc | 780 |
| gttgatcgta aacgcgttgg taaatttctg tttaccggtc tgctgcagtg tggtaattgt | 840 |
| ggtggccata aaatgcaggg ccatttttgat aaacgtgagc agaaaaccta ttaccgttgt | 900 |
| accaaatgtc accgcattac caacgaaaaa aacattctgg aaccgctgct ggatgaaatt | 960 |
| cagctgctga ttaccagcaa agaatacttt atgagcaaat tcagcgaccg ctatgatcag | 1020 |
| caagaggttg ttgatgttag cgcactgaca aaagaactgg aaaaaaatca acgccagaaa | 1080 |
| gagaaatggt acgatctgta tatggatgat cgtaacccga ttccgaaaga gaactgttt | 1140 |
| gccaaaatta cgaactgaa caaaaaagaa gaagaaatct atagcaagct gagcgaagtg | 1200 |
| gaagaagata agaaccggt tgaagagaaa tataaccgcc tgagcaaaat gatcgatttt | 1260 |
| aaacagcagt ttgagcaggc caacgacttt accaaaaaag agctgctgtt cagcatcttc | 1320 |
| gaaaagattg tgatttatcg cgagaaaggc aagctgaaaa aaatcaccct ggattacacc | 1380 |
| ctgaaataa | 1389 |

<210> SEQ ID NO 165
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 165

| | |
|---|---|
| atgaaagttg ccgtttattg tcgtgttagc accctggaac agaaagaaca tggtcatagc | 60 |
| attgaagaac aagagcgtaa actgaaaagc ttctgcgata ttaatgattg gaccgtgtat | 120 |
| gataccctata tcgatgcagg ttatagcggt gcaaacgtg atcgtccgga actgcagcgt | 180 |
| ctgatgaatg atattaacaa atttgatctg gtgctggtgt ataaactgga tcgtctgacc | 240 |
| cgtaatgttc gtgatctgct ggacctgctg gaaatctttg aaaaaaatga tgtgagcttt | 300 |
| cgtagcgcca ccgaagttta tgataccacc accgcaatgg gtcgtctgtt tgttaccctg | 360 |
| gttggtgcaa tggcagaatg ggaacgtgaa accattcgtg aacgtaccca tgatgggtaaa | 420 |
| ctggcagcac tgcgtaaagg tattatgctg accacccctc cgtttttatta tgaccgtgtg | 480 |
| gataataagt ttgtgccgaa caaatacaaa gacgttattc tgtgggcata tgacgaagca | 540 |
| atgaaaggtc agagcgcaaa agcaattgca cgcaaactga ataatagcga tattccgcct | 600 |
| ccgaataata cccagtggca gggtcgtacc attacccatg ccctgcgtaa tccgtttacc | 660 |
| cgtggtcatt ttgattgggg tggtgtgcat attgaaaata accatgaacc gatcatcacc | 720 |
| gatgagatgt atgagaaagt taaagatcgc ctgaatgaac gcgtgaacac caaaaaagtt | 780 |
| cgtcatacca gcattttttcg tggcaaactg gtttgtccgg tttgtaatgc acgcctgacc | 840 |
| ctgaatagcc ataaaaagaa agcaatagc ggctatatct ttgtgaaaca gtactactgc | 900 |
| aacaactgta aagttacccc gaatctgaaa ccggtgtaca tcaaagaaaa agaagtgatt | 960 |
| aaagtttttt acaattatct gaaacgcttc gatctggaaa aatatgaggt tacccagaaa | 1020 |

| | |
|---|---|
| cagaacgaac cggaaatcac catcgatatc aataaagtta tggaacagcg caaacgctac | 1080 |
| cataaactgt atgcaagcgg tctgatgcaa gaagatgaac tgtttgacct gattaaagaa | 1140 |
| accgatcaga ccattgccga atatgaaaaa cagaatgaaa accgcgaagt gaagcagtat | 1200 |
| gatatcgaag atatcaaaca gtataaagat ctgctgttag aaatgtggga tatcagctcc | 1260 |
| gatgaagata aagaggactt tatcaaaatg gcgattaaaa acatctattt tgaatatatc | 1320 |
| attggcaccg gtaacaccag ccgtaaacgt aatagcctga aaattacgag cattgaattc | 1380 |
| tattaa | 1386 |

<210> SEQ ID NO 166
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 166

| | |
|---|---|
| atgaaagtgg ccatttatac ccgtgttagc accctggaac agaaagaaaa aggtcatagc | 60 |
| atcgaagaac aagaacgtaa actgcgtgca tatagcgata tcaacgattg gaaaatccac | 120 |
| aaagtttata ccgatgcagg ttatagcggt gccaaaaaag atcgtccggc actgcaagaa | 180 |
| atgctgaatg aaattgataa cttcgatctg gtgctggtgt ataaactgga tcgtctgacc | 240 |
| cgtagcgtta aagatctgct ggaaattctg gaactgtttg aaaacaaaaa cgtgctgttt | 300 |
| cgtagcgcca ccgaagttta tgataccacc agtgcaatgg tcgtctgtt tgttaccctg | 360 |
| gttggtgcaa tggcagaatg ggaacgtacc accattcaag aacgcaccgc catgggtcgc | 420 |
| cgtgcaagcg cacgtaaagg tctggcaaaa accgttccgc ctttctatta tgatcgcgtg | 480 |
| aatgataaat ttgtgccgaa cgagtacaaa aaggttctgc gttttgcagt tgaagaagca | 540 |
| aaaaaaggca ccagcctgcg tgaaattacc attaaactga caacagcaa atacaaagca | 600 |
| ccgctgggta aaaattggca tcgtagcgtg attggtaatg cactgaccag tccggttgca | 660 |
| cgtggtcatc tggttttttgg tgatatttttt gtggaaaaca cccacgaagc cattattagc | 720 |
| gaagaggaat atgaagaaat caagctgcgc attagcgaaa aaaccaatag caccattgtg | 780 |
| aaacacaacg ccatttttcg tagcaaactg ctgtgtccga attgcaatca gaaactgacc | 840 |
| ctgaataccg ttaaacatac cccgaaaaac aaagaggtgt ggtacagcaa actgtatttt | 900 |
| tgcagcaatt gcaaaacac caaaaataag aacgcctgca catcgatga aggtgaagtt | 960 |
| ctgaaacagt tctacaacta tctgaagcag tttgatctga ccagctacaa aattgaaaac | 1020 |
| cagccgaaag aaattgagga tgtgggcatt gatattgaaa aactgcgtaa agaacgtgcc | 1080 |
| cgttgtcaga ccctgtttat tgaaggtatg atggataaag atgaagcctt tccgattatt | 1140 |
| agccgcatcg ataaagaaat ccacgagtat gaaaaacgca agacaacga taaaggcaaa | 1200 |
| acctttaact atgaaaagat taaaaacttc aaatatagcc tgctgaacgg ctgggaactg | 1260 |
| atggaagatg aactgaaaac cgagtttatc aagatggcga tcaaaaacat ccactttgag | 1320 |
| tatgtgaaag gcatcaaagg taaacgtcag aacagcctga aaattaccgg catcgaattc | 1380 |
| tattaa | 1386 |

<210> SEQ ID NO 167
<211> LENGTH: 1383
<212> TYPE: DNA
<213> ORGANISM: Artificial Sequence
<220> FEATURE:
<223> OTHER INFORMATION: Synthetic Polynucleotide

<400> SEQUENCE: 167

```
atgaaagtgg ccatttatac ccgtgttagc agcgcagaac aggcaaatga aggttatagc    60
attcacgagc agaagaagaa actgatcagc tattgcgaaa tccacgattg gaacgagtat   120
aaagttttta ccgatgcagg tattagcggt ggtagcatga acgtccggc actgcaaaaa    180
ctgatgaaac atctgagttc atttgatctg gtgctggtgt ataaactgga tcgtctgacc   240
cgtaatgttc gtgatctgct ggatatgctg gaagaatttg aacagtataa cgtgagcttt   300
aaaagcgcca ccgaagtttt tgataccacc agtgcaattg caaactgtt tattaccatg    360
gttggtgcaa tggcagaatg ggaacgtgaa accattcgtg aacgtagcct gtttggtagc   420
cgtgcagcag ttcgtgaagg taactatatt cgtgaagcac cgttttgcta tgataacatt   480
gaaggtaaac tgcacccgaa cgaatatgcc aaagttattg atctgattgt gagcatgttc   540
aaaaaaggca ttagcgccaa tgaaattgca cgtcgtctga atagcagcaa agttcatgtt   600
ccgaacaaaa aaagctggaa tcgtaatagc ctgattcgtc tgatgcgtag tccggttctg   660
cgtggtcata ccaaatatgg tgatatgctg attgaaaaca cccatgaacc ggtgctgagc   720
gaacatgatt ataatgcaat taacaacgcc atcagcagca aaaccataa agcaaagtt    780
aaacaccatg ccattttcg tggtgcactg gtttgtccgc agtgtaatcg tcgtctgcat    840
ctgtatgcag gcaccgttaa agatcgtaaa ggctataaat acgatgtgcg tcgctataaa   900
tgtgaaacct gcagcaaaaa caagatgtg aagaatgtga gcttcaacga aagcgaagtg    960
gaaaacaaat tcgtcaatct gctgaaaagc tacgagctga acaaatttca tatccgtaaa  1020
gtggaaccgg tgaaaaaaat cgagtatgac atcgataaga ttaacaaaca gaaaattaac  1080
tatacccgca gttggagcct gggctatatt gaagatgatg aatatttcga gctgatggaa  1140
gaaatcaacg ccaccaaaaa aatgatcgaa gaacagacca ccgagaataa acagagcgtt  1200
agcaaagagc agattcagag cattaacaac tttatcctga aaggctggga agaactgacc  1260
atcaaagata aagaggaact gattctgagc accgtggata aaatcgaatt taacttcatc  1320
ccgaaagata aaaacataa aaccaatacc ctggatatta acaatattca ctttaaattc  1380
taa                                                                1383
```

<210> SEQ ID NO 168
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 168

```
catataaaag aaaagacacc                                                 20
```

<210> SEQ ID NO 169
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 169

```
gaaataaaga catataaaag aaaagacacc                                       30
```

<210> SEQ ID NO 170
<211> LENGTH: 30
<212> TYPE: DNA
<213> ORGANISM: Artificial Sequence

```
<220> FEATURE:
<223> OTHER INFORMATION: Synthetic Polynucleotide

<400> SEQUENCE: 170
aaaaggatct attataagga ggcactcacc                                      30

<210> SEQ ID NO 171
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 171
aataggcctt tcggtccaca ctctctatag gcaaa                                35

<210> SEQ ID NO 172
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 172
cgcattttaa aataaaataa attatttatt taattaaacg aat                       43

<210> SEQ ID NO 173
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 173
tcccgcattt taaaataaaa taaattattc gtttagttaa acgaatatg                 49

<210> SEQ ID NO 174
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 174
tcccgcattt taaaataaaa taaattattt atttaattaa acgaatatg                 49

<210> SEQ ID NO 175
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 175
tcccgcattt taaaataaaa taaattatta gtttacttaa acgaatatg                 49

<210> SEQ ID NO 176
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 176
tcccgcattt taaaataaaa taaatcatct agttaattaa acgaatatg                 49
```

```
<210> SEQ ID NO 177
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 177
tcccgcattt taaataaaa taaattatta ttttatttaa acgaatatg          49

<210> SEQ ID NO 178
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 178
tcccgcattt taaataaaa taaattattg gtttacttaa acgaatatg          49

<210> SEQ ID NO 179
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 179
tcccgcattt taaataaaa taaattattc gtttaattaa acgaatatg          49

<210> SEQ ID NO 180
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 180
tcccgcattt taaataaaa taaattattc gtttagttaa acgaatatg          49

<210> SEQ ID NO 181
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 181
ttgatccaaa ttataacccg                                         20

<210> SEQ ID NO 182
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 182
agcttacgcc accctgttcc                                         20

<210> SEQ ID NO 183
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 183
tcacgctcac acccaggttc                                                       20

<210> SEQ ID NO 184
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 184
gacagaacga tgcgctgaat                                                       20

<210> SEQ ID NO 185
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 185
aaacaaaacc tcatcaggca                                                       20

<210> SEQ ID NO 186
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 186
gaagctcact ccttagcacg                                                       20

<210> SEQ ID NO 187
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 187
ctggaatgaa ttggcctatg                                                       20

<210> SEQ ID NO 188
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 188
gaaaatgggg tgtatcctgc                                                       20

<210> SEQ ID NO 189
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 189
attgaagaac aaaagcagtt                                                       20

```
<210> SEQ ID NO 190
<211> LENGTH: 87
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (46)..(48)
<223> OTHER INFORMATION: n is a, c, g, or t

<400> SEQUENCE: 190
gcatgaagac tcctcccgca ttttaaaata aaataaatta tttatnnnat taaacgaata      60
tggtttttac tctggaagat tttgttg                                         87

<210> SEQ ID NO 191
<211> LENGTH: 87
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 191
gcatgaagac tcctcccgca ttttaaaata aaataaatna tntanttaat taaacgaata      60
tggtttttac tctggaagat tttgttg                                         87

<210> SEQ ID NO 192
<211> LENGTH: 87
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t

<400> SEQUENCE: 192
gcatgaagac tcctcccgca ttttaaaata aaataaatta ttnntttant taaacgaata      60
tggtttttac tctggaagat tttgttg                                         87

<210> SEQ ID NO 193
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 193
gcatgaagac tcggagtgca aagttacgac aaataatttg                           40
```

<210> SEQ ID NO 194
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 194
ataaacgttc gtggtaacta tggg                                        24

<210> SEQ ID NO 195
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 195
gaccttcgga attcttccta gtg                                         23

<210> SEQ ID NO 196
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 196
ggaacactcc gtcggtcg                                               18

<210> SEQ ID NO 197
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 197
ccgtaatgtt cgtgatctgc                                             20

<210> SEQ ID NO 198
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 198
tttcacgttc ccattctgc                                              19

<210> SEQ ID NO 199
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 199
cccaggagag ttatcgactt gc                                          22

<210> SEQ ID NO 200
<211> LENGTH: 22
<212> TYPE: DNA
<213> ORGANISM: Artificial Sequence
<220> FEATURE:
<223> OTHER INFORMATION: Synthetic Polynucleotide

```
<400> SEQUENCE: 200
tgtccaaaat cgacctacac cg                                          22

<210> SEQ ID NO 201
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 201
tcacacaggt ttataacacc caatc                                       25

<210> SEQ ID NO 202
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 202
ccggtgcatt ggttaagact g                                           21

<210> SEQ ID NO 203
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 203
tgcaagactg tacatacttc catag                                       25

<210> SEQ ID NO 204
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 204
tctagaggat ctcaggcagc                                             20

<210> SEQ ID NO 205
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 205
gtgatcatcc cgtacgaagg                                             20

<210> SEQ ID NO 206
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 206
atcaccagcg taccgtaatg                                             20
```

<210> SEQ ID NO 207
<211> LENGTH: 330
<212> TYPE: DNA
<213> ORGANISM: Artificial Sequence
<220> FEATURE:
<223> OTHER INFORMATION: Synthetic Polynucleotide

<400> SEQUENCE: 207

```
ctacgttcaa ccaaaagaaa taatgactta ctgctatatt ttttgcacgt gtggggaaaa      60
tgtggggaaa attcaagcaa aagaaaaagc taagtattga actatcaaat acttagcttt     120
ctttcttgta cccagacccc gcatttgaaa taattaaagt ggggaaaatg tgggtaaaaa     180
gaaaaatgcg gaaaaacgcc acaattacac tgtatttcaa tatgttataa tcctattaaa     240
ttttaatcca agtttaatcg aattgcaaaa tatttagcag atgtggggaa aatgctgggg     300
aaaatattta tatttgcagc agagtaaaat                                      330
```

<210> SEQ ID NO 208
<211> LENGTH: 1338
<212> TYPE: DNA
<213> ORGANISM: Artificial Sequence
<220> FEATURE:
<223> OTHER INFORMATION: Synthetic Polynucleotide

<400> SEQUENCE: 208

```
atgaaagtaa cctttatcat taaaaaagca gccaaacgat atgatacaga atccatggct      60
acaatctatg tccgttttag aaacggaagg cagttagact ccgttgctcc tactcagtta     120
gccatcaatc ccaatctatg ggatgataaa gacgaatgtg taaaaacgaa agctgtctgc     180
aatgaagaaa tgcgtaccca tataaatgaa gagatacgcc agttgaaaac ctatatcgag     240
aaggtatatc aacaagaaaa ggaagcaata gacaaagaat ggctaaaaac aacacttgat     300
aaattttacc atcctgaaaa atattttttg ccggaggaag tggttatcaa gcctaccatt     360
ggagaactat tcgatgaatt tctaaacaag caccctttgt cggaagtacg aaagaaaaat     420
ttccggggttg tcaaaagagc cttactgcgt tatgaactat atgtaagggc tacaaagaga     480
ggacaaaagg gctttatcct tgatgtggat ttggtaacac ctgacacgct tcgggatatg     540
tgggatttct tcagaacga ataccagtat tatgaacttt acccgagcat ttatgaagcc     600
attcccgaaa agaggacacc acagcccaga agcaaaaaca cgctgataga ctgttttttca     660
agaatacgca cattcttcct gtggtgcttc gataacaaac gcaccacaaa cagaccttc     720
gacaagttc cgatagagga gtgtacatat ggtacacctt attatataac actcgaagaa     780
agggacagga ttttaatgc agaccttct gccaccccac aactggcaat acagagggat     840
atattcatat ttcagacact gataggatgc agggtgagcg acctgtaccg aatgaccaaa     900
ctaaatgtgg tcaatgaagc catagaatat attcccaaga aaccaaaga ggggaatccg     960
gttacggtac gtgttccact taacgacaaa gcgaagaaa tccttgaacg ctacaaagaa    1020
tatgagggaa aactgttgcc gttcatatcc gagcaaaagt acaatgatgc cataaaaaag    1080
atattcaaat tagctggagt tgaccgcatc gtaacaatct tagacccgtt gacgcacaac    1140
gaaatcaaac gacctatta tgaagtggca agcagccatc tggcaagacg tacgtttatc    1200
ggcaatatct ataaaaaagt gaaagacccg aaccttgttt ccgcactgtc gggacacaag    1260
gagggaagca aagctttcag acgatacagg gatattgacg aagaaatgaa gaaagacctt    1320
gtaaaactac tggactga                                                 1338
```

<210> SEQ ID NO 209
<211> LENGTH: 7180
<212> TYPE: DNA
<213> ORGANISM: Artificial Sequence
<220> FEATURE:
<223> OTHER INFORMATION: Synthetic Polynucleotide

<400> SEQUENCE: 209

| | | | | | |
|---|---|---|---|---|---|
| atggttttta | ctctggaaga | ttttgttggc | gattggcgtc | agaccgcggg | ttataatttg | 60 |
| gatcaagtcc | tggaacaggg | tggcgtaagc | tctctgttcc | agaacctggg | tgtgagcgtg | 120 |
| acgccgattc | agcgcatcgt | tctgtccggc | gagaacggtc | tgaaaattga | tattcatgtg | 180 |
| atcatcccgt | acgaaggcct | gagcggtgac | caaatgggtc | aaatcgagaa | aatctttaaa | 240 |
| gtcgtctacc | cagttgacga | tcaccacttc | aaggttatct | tgcattacgg | tacgctggtg | 300 |
| attgatggtg | tgaccccgaa | tatgattgac | tatttcggcc | gtccgtatga | aggcattgcc | 360 |
| gttttgacg | gtaaaaagat | caccgtcacc | ggtaccctgt | ggaatggcaa | taagattatt | 420 |
| gacgagcgtc | tgattaaccc | ggacggcagc | ctgctgttcc | gcgtgaccat | caacggtgtc | 480 |
| acgggttggc | gtctgtgcga | gcgcatcctg | gcataatgaa | ctgcacttgc | tttgataatt | 540 |
| aatgataaac | aatctaaaag | cactctaatc | gttatcggag | tgcttttaga | ttactaatca | 600 |
| aattgcttct | actaattgcc | tatcttccag | tgatggaaca | gcatttgtgc | attggctgca | 660 |
| acaatcagcc | ttgatctgga | agaagcaatg | aaagctgctg | ttaagtctcc | gaatcaggta | 720 |
| tgttcctga | caggtgtatt | cccatccggt | aaacgcggat | actttgcagt | tgatctgact | 780 |
| caggaataaa | ttataaatta | aggtaagaag | attgtaggat | aagctaatga | aatagaaaaa | 840 |
| ggatgccgtc | acacaacttg | tcggcattct | tttttgtttt | attagttgaa | aatatagtga | 900 |
| aaaagttgcc | taaatatgta | tgttaacaaa | ttatttgtcg | taactttgca | ctccaaatct | 960 |
| gttttttaaca | tatggcacta | gtggtgaatg | tgaaaccagt | aacgttatac | gatgtcgcag | 1020 |
| agtatgccgg | tgtctcttat | cagaccgttt | cccgcgtggt | gaaccaggcc | agccacgttt | 1080 |
| ctgcgaaaac | gcgggaaaaa | gtggaagcgg | cgatggcgga | gctgaattac | attcccaacc | 1140 |
| gcgtggcaca | caactggcg | gcaaacagt | cgttgctgat | tggcgttgcc | acctccagtc | 1200 |
| tggccctgca | cgcgccgtcg | caaattgtcg | cggcgattaa | atctcgcgcc | gatcaactgg | 1260 |
| gtgccagcgt | ggtggtgtcg | atggtagaac | gaagcggcgt | cgaagcctgt | aaagcggcgg | 1320 |
| tgcacaatct | tctcgcgcaa | cgcgtcagtg | ggctgatcat | taactatccg | ctggatgacc | 1380 |
| aggatgccat | tgctgtggaa | gctgcctgca | ctaatgttcc | ggcgttattt | cttgatgtct | 1440 |
| ctgaccagac | acccatcaac | agtattattt | tctcccatga | ggacggtacg | cgactgggcg | 1500 |
| tggagcatct | ggtcgcattg | ggtcaccagc | aaatcgcgct | gttagcgggc | ccattaagtt | 1560 |
| ctgtctcggc | gcgtctgcgt | ctggctggct | ggcataaata | tctcactcgc | aatcaaattc | 1620 |
| agccgatagc | ggaacgggaa | ggcgactgga | gtgccatgtc | cggttttcaa | caaaccatgc | 1680 |
| aaatgctgaa | tgagggcatc | gttcccactg | cgatgctggt | tgccaacgat | cagatggcgc | 1740 |
| tgggcgcaat | gcgcgccatt | accgagtccg | ggctgcgcgt | tggtgcggat | atctcggtag | 1800 |
| tgggatacga | cgataccgag | gacagctcat | gttatatccc | gccgttaacc | accatcaaac | 1860 |
| aggattttcg | cctgctgggg | caaaccagcg | tggaccgctt | gctgcaactc | tctcagggcc | 1920 |
| aggcggtgaa | gggcaatcag | ctgttgcccg | tctcactggt | gaaaagaaaa | accaccctgg | 1980 |
| cgcccaatac | gcaaaccgcc | tctccccgcg | cgttggccga | ttcattaatg | cagctggcac | 2040 |
| gacaggtttc | ccgactggaa | agcgggcagt | gagctttcct | cggtaccaaa | ttccagaaaa | 2100 |

```
gaggcctccc gaaaggggggg cctttttttcg ttttggtcct acttgtgcct gttctatttc    2160
cgaaccgacc gcttgtatga atccatcaaa attcgttttc tctatgttgg attccttgtt    2220
gctcatattg tgatgataat ttctacaaat atagtcattg gtaactatct atgaaactgt    2280
ttgatacttt tatcagtcca gtagttttac aaggtctttc ttcatttctt cgtcaatatc    2340
cctgtatcgt ctgaaagctt tgcttccctc cttgtgtccc gacagtgcgg aaacaaggtt    2400
cgggtctttc acttttttat agatattgcc gataaacgta cgtcttgcca gatggctgct    2460
tgccacttca taaataggtc gtttgatttc gttgtgcgtc aacgggtcta agattgttac    2520
gatgcggtca actccagcta atttgaatat cttttttatg gcatcattgt acttttgctc    2580
ggatatgaac ggcaacagtt ttccctcata ttctttgtag cgttcaagga tttctttcgc    2640
tttgtcgtta agtggaacac gtaccgtaac cggattcccc ctttggtttt cttgggaat    2700 atattctatg gcttcattga ccacatttag tttggtcatt cggtacaggt cgctcaccct    2760
gcatcctatc agtgtctgaa atatgaatat atccctctgt attgccagtt gtggggtggc    2820
agaaaggtct gcattaaaaa tcctgtccct ttcttcgagt gttatataat aaggtgtacc    2880
atatgtacac tcctctatcg gaaacttgtc gaaaggtctg tttgtggtgc gtttgttatc    2940
gaagcaccac aggaagaatg tgcgtattct tgaaaaacag tctatcagcg tgttttgct    3000 tctgggctgt ggtgtcctct tttcgggaat ggcttcataa atgctcgggt aaagttcata    3060
atactggtat tcgttctgaa agaaatccca catatcccga agcgtgtcag gtgttaccaa    3120
atccacatca aggataaagc ccttttgtcc tctctttgta gcccttacat atagttcata    3180
acgcagtaag gctcttttga caacccggaa attttctttt cgtacttccg acaaagggtg    3240
cttgtttaga aattcatcga atagttctcc aatggtaggc ttgataacca cttcctccgg    3300 caaaaatat ttttcaggat ggtaaaattt atcaagtgtt gtttttagcc attctttgtc    3360
tattgcttcc ttttcttgtt gatataccct tcgatatag gttttcaact ggcgtatctc    3420
ttcatttata tgggtacgca tttcttcatt gcagacagct ttcgttttta cacattcgtc    3480
tttatcatcc catagattgg gattgatggc taactgagta ggagcaacgg agtctaactg    3540
ccttccgttt ctaaaacgga catagattgt agccatggat tctgtatcat atcgtttggc    3600 tgcttttta atgataaagg ttactttcat agactttcag gttgaatttt actctgctgc    3660
aaatataaat attttcccca gcattttccc cacatctgct aaatattttg caattcgatt    3720
aaacttggat taaaatttaa taggattata acatattgaa atacagtgta attgtggcgt    3780
ttttccgcat ttttctttt acccacattt tccccacttt aattattca aatgccgggt    3840 ctgggtacaa gaaagaaagc taagtatttg atagttcaat acttagcttt ttcttttgct    3900 tgaatttcc ccacattttc cccacacgtg caaaaaatat agcagtaagt cattatttct    3960
tttggttgaa cgtagagagt agcgatatta aagaatccg atgagaaaag actaatattt    4020
atctatccat tcagtttgat ttttcaggac tttacatcgt cctgaaagta tttgttggta    4080
ccggtaccga ggacgcgtaa acatttacag ttgcatgtgg cctattgttt ttagccgtta    4140
aatattttat aactattaaa tagcgataca aattgttcga aactaatatt gtttatatca    4200
tatattctcg catgttttaa agctttatta aattgatttt ttgtaaacag ttttttcgtac    4260 tctttgttaa cccatttcat tacaaaagtt tcatattttt ttctctcttt aaatgccatt    4320
tttgctggct ttcttttaa tacaattaat gtgctatcca ctttaggttt tggatggaaa    4380
taatacctag gaattttgc taatatagaa atatctacct ctgccattaa cagcaatgct    4440
agtgatctgt ttgtatctaa taacatttta gcaaaaccat attccactat taaataactt    4500
```

```
attgtggctg aactttcaaa aacaattttt cgaattatat ttgtgcttat gttgtaaggt   4560
atgctgccaa atattttata tggattgtgg ctaggaaatg taaatttcag tatatcatca   4620
tttactattt gatagttagg ataatttaag agcttattac gagttacctc acataattta   4680
gaatcaattt ctatcgccgt tacaaaatta catctcttta ccaatccagc agtaaaatga   4740
cctttccctg cacctatttc aaagatgtta tcttttcat ctaaacttat gcaattcatt   4800
atttttctcta tgtgatattt tgaagtaata aaattttgac tatcttttat atttactttg   4860
ttcattataa cctctcctta atttattgca tctcttttcg aatatttatg ttttttgaga   4920
aaagaacgta ctcatggttc atcccgatat gcgtatcggt ctgtatatca gcaactttct   4980
atgtgtttca actacaatag tcatctattc tcatctttct gagtccaccc cctgcaaagc   5040
ccctctttac gacataaaaa ttcggtcgga aaaggtatgc aaaagatgtt tctctcttta   5100
agagaaactc ttcgggatgc aaaaatatga aaataactcc aattcaccaa attatatagc   5160
gactttttta caaaatgcta aaatttgttg atttccgtca agcaattgtt gagcaaaaat   5220
gtcttttacg ataaaatgat acctcaatat caactgttta gcaaaacgat atttctctta   5280
aagagagaaa cacctttttg ttcaccaatc cccgactttt aatcccgcgg ccatgattga   5340
aaaaggaaga gtatgagtat tcaacatttc cgtgtcgccc ttattccctt ttttgcggca   5400
ttttgccttc ctgttttgc tcacccagaa cgctggtga agtaaaaga tgctgaagat   5460
cagttgggtg cacgagtggg ttacatcgaa ctggatctca acagcggtaa gatccttgag   5520
agttttcgcc ccgaagaacg ttttccaatg atgagcactt ttaaagttct gctatgtggc   5580
gcggtattat cccgtattga cgccgggcaa gagcaactcg tcgccgcat acactattct   5640
cagaatgact tggttgagta ctcaccagtc acagaaaagc atcttacgga tggcatgaca   5700
gtaagagaat tatgcagtgc tgccataacc atgagtgata acactgcggc caacttactt   5760
ctgacaacga tcggaggacc gaaggagcta accgcttttt tgcacaacat ggggatcat   5820
gtaactcgcc ttgatcgttg gaaccggag ctgaatgaag ccataccaaa cgacgagcgt   5880
gacaccacga tgcctgtagc aatggcaaca acgttgcgca aactattaac tggcgaacta   5940
cttactctag cttcccggca acaattaata gactggatgg aggcggataa agttgcagga   6000
ccacttctgc gctcggccct tccggctggc tggtttattg ctgataaatc tggagccggt   6060
gagcgtgggt ctcgcggtat cattgcagca ctggggccag atggtaagcc ctcccgtatc   6120
gtagttatct acacgacggg gagtcaggca actatggatg aacgaaatag acagatcgct   6180
gagataggtg cctcactgat taagcattgg taactgtcag accaagttta ctcataacgc   6240
gtcaattcga gggggatcaa ttccgtgata ggtgggctgc ccttcctggt tggcttggtt   6300
tcatcagcca tccgcttgcc ctcatctgtt acgccggcgg tagccggcca gcctcgcaga   6360
gcaggattcc cgttgagcac cgccaggtgc gaataaggga cagtgaagaa ggaacacccg   6420
ctcgcgggtg ggcctacttc acctatcctg cccggctgac gccgttggat acaccaagga   6480
aagtctacac gaacccttg gcaaaatcct gtatatcgtg cgaaaaagga tggatatacc   6540
gaaaaaatcg ctataatgac cccgaagcag ggttatgcag cggaaaacgg aattgatccg   6600
gccacgatgc gtccggcgta gaggatctga agatcagcag ttcaacctgt tgatagtacg   6660
tactaagctc tcatgtttca cgtactaagc tctcatgttt aacgtactaa gctctcatgt   6720
ttaacgaact aaaccctcat ggctaacgta ctaagctctc atggctaacg tactaagctc   6780
tcatgtttca cgtactaagc tctcatgttt gaacaataaa attaatataa atcagcaact   6840
taaatagcct ctaaggtttt aagttttata agaaaaaaaa gaatatataa ggcttttaaa   6900
```

```
gcttttaagg tttaacggtt gtggacaaca agccagggat gtaacgcact gagaagccct    6960
tagagcctct caaagcaatt ttgagtgaca caggaacact taacggctga catgggaatt    7020
cccctccacc gcggtggtta caagaaaat tcgacaaact gttatttttc tatctattta    7080
tttgaattgt gagcggataa caattacctt tgtcggcaat tgtgagcgga taacaattaa    7140
ataaagatat tctcgtcaaa caaatataaa taatataaac                          7180

<210> SEQ ID NO 210
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 210
aatataatta a                                                         11

<210> SEQ ID NO 211
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 211
cattcggtcc t                                                         11

<210> SEQ ID NO 212
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 212
gttttattag ttgaaaatat agtgaaaaag ttgcctaaat atgtatgtta acaaattatt    60
tgtcgtaact ttgcactcca a                                              81

<210> SEQ ID NO 213
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 213
gctttgcaac agcatagctc agcacagaag ttgcctaaat atgtatgtta acaaattatt    60
tgtcgtaact ttgcactcca a                                              81

<210> SEQ ID NO 214
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 214
gttttattag ttgaaaatat agtgaaaaag ttgcctaaat atgtatgtta acaaattctt    60
tgcaacagca tagctcagca caggcactcc aa                                  92
```

```
<210> SEQ ID NO 215
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 215
gttttattag ttgaaaatat agtgaaaact ttgcaacagc atagctcagc acagattatt      60
tgtcgtaact ttgcactcca a                                               81

<210> SEQ ID NO 216
<211> LENGTH: 107
<212> TYPE: DNA
<213> ORGANISM: Artificial Sequence
<220> FEATURE:
<223> OTHER INFORMATION: Synthetic Polynucleotide

<400> SEQUENCE: 216
gttttattag ttgaaaatat agtgaaaaag ttgcctaaat atgtatgtta acaaattatt      60
tgtcgtaact ttgcactccc tttgcaacag catagctcag cacagaa                  107

<210> SEQ ID NO 217
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 217
atttatttgg gtgggaaact ttagttatgt acctttgtcg gcaaa                     45

<210> SEQ ID NO 218
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 218
atttaaattg tgagcggata acaatttgaa ttgtgagcgg ataacaatta cctttgtcgg      60
caaa                                                                  64

<210> SEQ ID NO 219
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 219
atttaaattg tgagcggata acaatttggg tgggaaactt tagttatgta cctttgtcgg      60
caattgtgag cggataacaa ttaaa                                           85

<210> SEQ ID NO 220
<211> LENGTH: 66
<212> TYPE: DNA
<213> ORGANISM: Artificial Sequence
<220> FEATURE:
<223> OTHER INFORMATION: Synthetic Polynucleotide
```

```
<400> SEQUENCE: 220
atttatttga attgtgagcg gataacaatt acctttgtcg gcaattgtga gcggataaca     60
attaaa                                                                66
```

GENE EXPRESSION IN BACTEROIDES

RELATED APPLICATIONS

This application is a national stage filing under 35 U.S.C. § 371 of international application number PCT/US2016/036811, filed Jun. 10, 2016, which was published under PCT Article 21(2) in English and claims the benefit under 35 U.S.C. § 119(e) of U.S. provisional application Ser. No. 62/173,481, filed Jun. 10, 2015, each of which is incorporated by reference herein in its entirety.

FEDERALLY SPONSORED RESEARCH

This invention was made with government support under Grant No. FA8721-05-C-0002 awarded by the U.S. Air Force. The government has certain rights in the invention.

FIELD OF THE INVENTION

Aspects of the present disclosure relate to the general field of biotechnology and, more particularly, to the fields of genetic engineering and microbiology.

BACKGROUND OF THE INVENTION

*Bacteroides* species are prominent Gram-negative anaerobic symbionts of the mammalian gut microbiome, comprising 25% of culturable anaerobes in the human gastrointestinal tract. Of the *Bacteroides* genus, *Bacteroides thetaiotaomicron* is both prevalent (present in 46% of humans) and abundant (up to $10^{10}$ per gram stool). Stable and robust colonization of the densely populated gut environment is facilitated by the metabolic diversity of *Bacteroides*. Specifically, *B. thetaiotaomicron* and its relatives are equipped with an extensive repertoire of saccharolytic enzymes and serve as primary fermenters of host-, diet- or microbially-derived polysaccharides.

SUMMARY OF THE INVENTION

*Bacteroides* thetaiotaomicron, a commensal bacterium, forms stable interactions with the gastrointestinal tract and is a candidate for modulating the gut ecosystem. However, there are few genetic parts and circuits available to control expression in this *Bacteroides* species as well as other *Bacteroides* and *Parabacteroides* species. Provided herein is a library of constitutive promoters and ribosome-binding sites that may be used, in some embodiments, to achieve a 10,000-fold range in gene expression. For inducible control, a series of promoters, able to elicit up to 100-fold regulation in gene expression, were constructed. Further provided herein are vector systems that maybe used to manipulate gene expression in a variety of *Bacteroides* and *Parabacteroides* species. These tools were used as a platform to build recombinase-based memory gates that permanently record DNA-encoded information in the genome. CRISPR interference (CRISPRi) was used to enable the regulated knockdown of recombinant and endogenous gene expression. Finally, the function of the inducible systems, CRISPRi, and memory switch were validated in *B. thetaiotaomicron* colonizing the mouse gut. Collectively, these tools provide a resource to engineer *Bacteroides* and *Parabacteroides* to respond to environmental stimuli, record this information, and control genetic pathways as a means of surveillance of or therapeutic delivery to the human microbiome.

Some aspects of the present disclosure are directed to *Bacteroides* (or *Parabacteroides*) bacteria comprising (a) an engineered nucleic acid comprising a region containing a promoter and a nucleotide sequence encoding a ribosomal binding site (RBS) operably linked to a nucleotide sequence encoding a recombinase, and (b) an engineered nucleic acid comprising a promoter and a nucleotide sequence encoding a RBS operably linked to a nucleotide sequence encoding a molecule of interest, wherein the nucleotide sequence encoding the molecule of interest is flanked by a pair of cognate recombinase recognition sequences.

In some embodiments, wherein the nucleotide sequence encoding a RBS comprises a sequence selected from the group consisting SEQ ID NO: 1-SEQ ID NO: 143 and SEQ ID NO: 168-SEQ ID NO: 172.

In some embodiments, the promoter is constitutive. Thus, the region containing a promoter and a nucleotide sequence encoding a RBS may comprise a sequence selected from the group consisting SEQ ID NO: 151-SEQ ID NO: 155 and SEQ ID NO: 160-SEQ ID NO: 163. Other constitutive promoters are encompassed by the present disclosure.

In some embodiments, the promoter is inducible. Thus, the region containing a promoter and a nucleotide sequence encoding a RBS may comprise a sequence selected from the group consisting SEQ ID NO: 144-SEQ ID NO: 149. Other inducible promoters are encompassed by the present disclosure.

In some embodiments, the recombinase is a serine recombinase or a tyrosine recombinase. For example, the recombinase may be a serine recombinase. In some embodiments, the serine recombinase is selected from the group consisting of Int1 (SEQ ID NO: 164), Int8 (SEQ ID NOT: 165), Int9 (SEQ ID NO: 166) and Int12 (SEQ ID NO: 167). Other serine recombinases and tyrosine recombinases are encompassed by the present disclosure.

Also provided herein are *Bacteroides* (or *Parabacteroides*) bacteria comprising an engineered nucleic acid comprising a promoter and a nucleotide sequence encoding a ribosomal binding site (RBS) operably linked to a nucleotide sequence encoding a molecule of interest, wherein the RBS comprises a sequence selected from the group consisting SEQ ID NO: 1-SEQ ID NO: 143 and SEQ ID NO: 168-SEQ ID NO: 172.

Further provided herein are *Bacteroides* (or *Parabacteroides*) bacteria comprising an engineered nucleic acid comprising a region containing a constitutive promoter and a nucleotide sequence encoding a ribosomal binding site (RBS) operably linked to a nucleotide sequence encoding a molecule of interest, wherein the region containing a constitutive promoter and a RBS comprises a sequence selected from the group consisting SEQ ID NO: 151-SEQ ID NO: 155 and SEQ ID NO: 160-SEQ ID NO: 163.

Also provided herein are *Bacteroides* bacteria comprising an engineered nucleic acid comprising a region containing an inducible promoter and a nucleotide sequence encoding a ribosomal binding site (RBS) operably linked to a nucleotide sequence encoding a molecule of interest, wherein the region containing an inducible promoter and a RBS comprises a sequence selected from the group consisting SEQ ID NO: 144-SEQ ID NO: 149.

Further provided herein are *Bacteroides* (or *Parabacteroides*) bacteria comprising an engineered nucleic acid comprising a region containing an inducible promoter and a nucleotide sequence encoding a ribosomal binding site (RBS) operably linked to a nucleotide sequence encoding a molecule of interest, wherein the nucleotide sequence encoding a RBS is immediately downstream from (3' from)

a 10-nucleotide to 20-nucleotide region, wherein at least 80% of the nucleotides in the 10-nucleotide to 20-nucleotide region are adenine or thymine, or a combination of adenine and thymine.

In some embodiments, the molecule of interest is a therapeutic molecule, a prophylactic molecule, or a diagnostic molecule.

Some aspects of the present disclosure provide methods of expressing a molecule of interest in a *Bacteroides* (or *Parabacteroides*) bacterium, the method comprising culturing a *Bacteroides* (or *Parabacteroides*) bacterium (or a population of *Bacteroides* bacteria), as described herein, under conditions that result in expression of the molecule of interest.

Some aspects of the present disclosure provide methods of treating a condition in a subject, the method comprising administering to the subject a *Bacteroides* (or *Parabacteroides*) bacterium, as described herein, wherein the molecule of interest is a therapeutic molecule. Some aspects of the present disclosure provide methods of preventing a condition in a subject, the method comprising administering to the subject a *Bacteroides* (or *Parabacteroides*) bacterium, as described herein, wherein the molecule of interest is a prophylactic molecule.

Also provided herein are *Bacteroides* (or *Parabacteroides*) bacteria comprising (a) an engineered nucleic acid comprising a region containing a promoter and a nucleotide sequence encoding a ribosomal binding site (RBS) operably linked to a nucleotide sequence encoding a catalytically-inactive Cas9 nuclease, and (b) an engineered nucleic acid comprising a promoter and a nucleotide sequence encoding a RBS operably linked to a nucleotide sequence encoding a guide RNA, wherein the guide RNA targets a nucleotide sequence encoding a molecule of interest.

In some embodiments, the catalytically-inactive Cas9 nuclease is encoded by the nucleotide sequence of SEQ ID NO: 157.

Some aspects of the present disclosure provide engineered nucleic acids comprising a nucleotide sequence selected from the group consisting of SEQ ID NO: 1-SEQ ID NO: 180.

In some embodiments, the present disclosure provides a vector comprising the genetic elements depicted in FIG. 10, including a nucleotide sequence encoding an IntN1 integrase (e.g., obtained from *B. uniformis*), capable of facilitating integration of the vector in a variety of *Bacteroides* and *Parabacteroides* species. Thus, in some embodiments, the present disclosure provides an engineered nucleic acid comprising the nucleotide sequence of SEQ ID NO: 206, or a nucleotide sequence having at least 80%, at least 85%, at least 90%, at least 95%, at least 98% or at least 99% identity with the nucleotide sequence of SEQ ID NO: 206.

Also provided herein are cells comprising engineered nucleic acid(s), as described herein (e.g., engineered nucleic acids comprising a nucleotide sequence selected from the group consisting of SEQ ID NO: 1-SEQ ID NO: 180).

BRIEF DESCRIPTION OF THE DRAWINGS

The accompanying drawings are not intended to be drawn to scale. For purposes of clarity, not every component may be labeled in every drawing.

(FIG. 1A) The ranges of gene expression are shown for the different gene regulation systems provided herein. (FIG. 1B) IntN2 catalyzes stable integration of pNBU2-based expression constructs into one of two attBT2 sites in the *B. thetaiotaomicron* genome. The two attBT2 sites (attBT2-1 at nucleotide (nt) 6,217,227 and attBT2-2 at nt 6,138,320) are in the 3' ends of tRNA$^{Ser}$ genes (BT_t71 and BT_t70, respectively). (FIG. 1C) Constitutive promoters and ribosome binding sites for the construction of gene expression libraries. The putative −33 and −7 regions of the $P_{BT1311}$ promoter, the Shine-Delgarno sequence, and the start codon are indicated by black boxes. Numbers below the black boxes represent nucleotide locations relative the $P_{BT1311}$ transcription start site. The 26 nt sequences introduced in the $P_{AM}$ promoters are shown (see also FIGS. 6A-6B). Numbers at the edges of the boxes indicate the $P_{BT1311}$ nucleotides replaced or the insertion site within the promoter. The location of residues randomized in the rpiL* RBS library are indicated with gray arrows (for library A: nt −14, −13, −12; for library B: nt −21, −18, −15; and for library C: nt −17, −16, −11; nt numbering is relative to the translation start site). (FIG. 1D) Activity was measured for a set of constitutive promoters and their cognate RBSs. Furthermore, a set of constitutive promoters ($P_{BT1311}$, $P_{AM1}$, $P_{AM2}$, $P_{AM3}$, $P_{AM4}$) was combined with RBSs of varying strengths. Gene expression was measured using a luciferase reporter (NanoLuc). (FIG. 1E) Three large RBS libraries were constructed and combined with promoter $P_{BT1311}$ to span $10^3$-fold in gene expression. For reference, the parent rpiL* RBS is indicated with a black arrow. The sequences of the RBSs are provided in Table 1. For D and E, error bars represent the standard deviation of three independent biological replicates made on separate days. (FIG. 1F) The strength of each RBS was compared to the predicted free energy of folding for the mRNA ($\Delta G_{fold}$). (FIG. 1G) Strong (SEQ ID NO: 210) and weak (SEQ ID NO: 211) consensus sequences for the rpiL* −21 to −11 RBS region targeted by mutagenesis (residue locations are stated relative to the translation start site) are provided. Frequency logos were generated for the 11 strongest and 11 weakest RBSs by comparing the frequency of each nucleotide at each position in that group with the frequency of that nucleotide in that position in the full library. Position −20 and −19 were not randomized and are thus are not shown in the frequency logos.

FIGS. 2A-2E. Design and characterization of genetic sensors. (FIGS. 2A-2D) Response curves for NanoLuc under the regulated control of the rhamnose—(Rha) (FIG. 2A), chondroitin sulfate—(ChS) (FIG. 2B), arabinogalactan—(AG) (FIG. 2C), or IPTG—(FIG. 2D) inducible promoters. LacO1 operator sites were inserted in various regions (O1, O2, O3) of the $P_{cfxA}$ promoter (see also FIGS. 7A-7B). Inducer concentrations were applied as follows: three-fold serial dilutions starting at 10 mM Rha (FIG. 2A); three-fold serial dilutions starting at 0.4% for ChS (FIG. 2B) and AG (FIG. 2C); and four-fold serial dilutions starting at 500 µM for IPTG (FIG. 2D). The leftmost data point in each plot represents the background luminescence in the absence of inducer. Response curves were fit to a Hill function (solid lines). (FIG. 2E) Orthogonality matrix of sugar-inducible genetic systems incubated with 10 mM rhamnose (Rha), 0.2% chondroitin sulfate (ChS), 0.2% arabinogalactan (AG), or 100 mM IPTG compared to no inducer. Error bars represent the standard deviation of three biological replicates made on different days.

(FIG. 3A) Integrases mediate recombination of DNA between integrase binding sites (attB/attP), resulting in the inversion of intervening spacers. (FIG. 3B) Schematic of the location of the promoter-RBS-integrase system and the memory array cassettes in the *B. thetaiotaomicron* chromosome. (FIG. 3C)

Integrase-mediated DNA inversion at each integrase target sequence in the memory array cassette was detected by polymerase chain reaction (PCR). Primer pairs (arrows) anneals to the interface of the integrase recognition sites and to the spacer region between recognition sites. PCR amplification occurs only after an inversion event (solid lines below the primer arrows indicate expected amplicons). (FIG. 3D) Representative PCR products are shown after recombination. − indicates no integrase, + indicates the integrase is present. $P_{AM4}$-rpiL* was used to control expression of each integrase. (FIG. 3E) Schematic of the rhamnose-inducible recombinase circuit. Transcriptional activator RhaR, produced from the endogenous locus, is activated in the presence of rhamnose causing expression of Int12 from $P_{rha}$. Int12 mediates recombination between the Int12 attB and attP recognition sequences. (FIG. 3F) Response curve of Int12 memory circuit. Int12 was placed under the control of a subset of $P_{3763}$-rpiL*C51. Inducer concentrations were nine-fold serial dilutions starting at 10 mM rhamnose. The leftmost data point represents the recombination in the absence of inducer. Cells were grown 8 hours at 37° C. before harvesting cells and isolating DNA. qPCR was used to measure the fold-change in flipping relative to the 10 mM rhamnose sample using the Int12 gene for reference. Data were fit with a Hill function to guide the eye. (FIG. 3G) Int12-mediated recombination versus time. Cells were induced with 10 mM rhamnose at t=0. qPCR was used to measure the fold-change in flipping relative to the t=8 sample using the Int12 gene for reference. For FIGS. 3F-G, error bars represent the standard deviation of three biological replicates made on different days.

(FIG. 4A) Schematic of dCas9-based repression of NanoLuc. $LacI^Q$ is expressed from $P_{BT1311}$ and represses transcription from the $P_{LacO23}$ promoter. Addition of IPTG inactivates $LacI^Q$ to allow expression of dCas9 from $P_{LacO23}$. dCas9 complexes with guide RNA (sgRNA) constitutively expressed from the $P_1$ promoter to prevent the transcription of NanoLuc from the $P_{cfiA}$ promoter. Guide RNAs were designed to target the coding sequence of NanoLuc (NL1-4) or the $P_{cfiA}$ promoter (PR1-2). (FIG. 4B) Response curves of dCas9-mediated targeting the coding sequence of NanoLuc (NL1-4), the promoter (PR1-2) or a nonsense sequence (NS). Fourfold serial dilutions of IPTG starting at 500 µM or no inducer were added to cultures. Response curves were fit to a Hill Function (solid lines). (FIG. 4C) Fold repression elicited by various gRNAs in the presence (500 µM) of inducer. Bars are colored to correspond to part B. (FIG. 4D) Genomic location of endogenous genes targeted using CRISPRi. (FIG. 4E) Minimum inhibitory concentrations (MICs) of polymyxin B for cells with CRISPRi targeted against BT1854 ($dCas9_{BT1854}$) compared with wild-type (WT) cells or non-specific control cells ($dCas9_{NS}$). Reported values are the mode of three independent biological replicates made on three separate days. (FIG. 4F) CRISPRi was targeted against BT1754 ($dCas9_{BT1754}$). Growth curves of wild-type (WT) (black), $dCas9_{BT1754}$ (pink) or $dCas9_{NS}$ (gray) cells in minimal media supplemented with 0.5% glucose (MM-Glc) or 0.5% fructose (MM-Fru) in the presence (full line) or absence (dotted line) of 100 mM IPTG. Error bars represent the standard deviation of three biological replicates made on different days.

FIGS. 5A-5D. In vivo function of genetic parts within B. thetaiotaomicron colonizing the mouse gut. (FIG. 5A) Experimental timeline. Specific pathogen free (SPF) Swiss Webster mice were treated for 10 days with ciprofloxacin and metronidazole and gavaged with B. thetaiotaomicron 2 days after cessation of treatment. (FIGS. 5B-5C) Luciferase activity in fecal pellets of mice inoculated with strains possessing the arabinogalactan (AG) inducible $P_{0268}$ (FIG. 5B) or IPTG-inducible CRISPRi $dCas9_{NL3}$ (FIG. 5C) systems. Mice were provided drinking water supplemented with 5% arabinogalactan (FIG. 5B: solid line), or 25 mM IPTG (FIG. 5C: solid line) after stool collection on Day 2 (grey box), or were maintained on normal drinking water throughout the entire experiment (dashed lines). Inducer water was removed on Day 4 after stool collection. Grey boxes indicate the period of time that mice were exposed to inducer-supplemented drinking water. Luminescence values were normalized to cell density as determined by qPCR using NanoLuc-specific primers. (FIG. 5D) SPF mice were colonized with B. thetaiotaomicron containing the rhamnose-inducible integrase construct $P_{3763}$-rpiL*C51-Int12. All mice were exposed to 0.3% rhamnose (w/w) in the plant-based chow. In addition, half of the mice had their drinking water supplemented with 500 mM rhamnose after stool collection on Day 1 ("Chow+Rha", solid line) while the other half of the mice were maintained on normal drinking water throughout the entire experiment ("Chow", dashed line). Mice receiving rhamnose-supplemented water on Days 1 and 2 (grey box) were returned to normal water on Day 3 after stool collection. Absolute quantities of flipped and unflipped memory array in fecal DNA were determined by qPCR using standard curves (Experimental Procedures). Recombination frequency is expressed as the ratio of cells containing a flipped memory array (Flipped) divided by the sum total of cells containing a flipped or unflipped array (Total). For day 3 "Chow" samples, n=3. For all other days, n=6 for both treatment groups. For FIGS. 5B-D, individual points represent independent biological replicates and the line represents the mean of the group. *P<0.05; **P<0.01.

FIGS. 6A-6B. PAM promoter sequences and induction with fucose. (FIG. 6A) Promoters PAM1, PAM2, PAM3, and PAM4 were constructed by introducing a 26 bp sequence (gray) at 4 locations in the constitutive BT1311 promoter (PBT1311). Predicted −33, −7, and +1 sites of the PBT1311 promoter are shown in bold. FIG. 6A depicts SEQ ID NOs: 212 to 216 from top to bottom, respectively. (FIG. 6B) Activity of promoters PAM1, PAM2, PAM3, and PAM4 were measured in the presence (filled bars) or absence (open bars) of fucose (10 mM). Error bars represent the standard deviation of three biological replicates made on three different days (n=3).

(FIG. 7A) Synthetic IPTG-inducible promoters were constructed by placing LacO1 operator sites (red) upstream of the −33 element (O1), between the −33 and −7 elements (O2) and/or directly downstream of the transcription start site (O3) of the strong $P_{cfxA}$ promoter. Predicted −33, −7 and +1 sites are shown in bold. These promoters are regulated by the E. coli LacIQ repressor expressed from PBT1311. FIG. 7A depicts SEQ ID NOs: 217 to 220 from top to bottom, respectively. (FIG. 7B) Response curves for the synthetic IPTG-inducible systems. Cells were incubated with no inducer or four-fold serial dilutions of IPTG starting at 500 µM. Data sets for $P_{LacO13}$ and $P_{LacO23}$ were fit to a Hill function (solid line). Error bars represent the standard deviation of three biological replicates made on three different days (n=3).

(FIG. 8A) Representative PCR products are shown for wild-type (unflipped) memory array at each integrase recognition sequence. "−" indicates no integrase, "+" indicates the integrase is present. $P_{AM4}$-rpiL* was used to control expression of each integrase. (FIG. 8B) Cell growth of the $P_{3763}$-rpiL*C51-Int12 strain is shown as optical density (OD) at 600 nm as a function of rhamnose concentration. Inducer concentrations were three-fold serial dilutions starting at 10 mM rhamnose. The leftmost data point represents the recombination in the absence of inducer. Cells were grown 8 hours at 37° C. before measuring the OD600 value for each culture. Error bars represent the standard deviation of three biological replicates made on three different days (n=3).

(FIGS. 9A-9B) Cell densities of the arabinogalactan-inducible $P_{0268}$ (FIG. 9A) or the dCas9$_{NL3}$ (FIG. 9B) strains in the fecal pellets of inoculated mice. 5% arabinogalactan (FIG. 9A: solid line) or 25 mM IPTG (FIG. 9B: solid line) was added to the drinking water of mice on Day 2 after stool collection (solid lines) and mice were returned to normal water on Day 4 after stool collection. The control groups (dashed lines) remained on normal water for the duration of the experiment. Grey boxes indicate the period of time over which mice were exposed to inducer in their drinking water. Bacterial loads were quantified by analyzing DNA extracted from fecal pellet using qPCR. The number of cells was determined using NanoLuc-specific primers and a standard curve generated with purified NanoLuc amplicons. Results were normalized to the weight of fecal material analyzed. (FIG. 9C) Bacterial load of the rhamnose-inducible integrase strain in the fecal pellets of inoculated mice. All mice were exposed to 0.3% rhamnose (w/w) in the plant-based chow. Rhamnose supplemented drinking water was provided to half of the mice ("Chow+Rha", solid line) on Day 1 after stool collection and normal water was returned on Day 3 after stool collection (grey box). The other half of the mice ("Chow", dashed line) remained on normal water for the duration of the experiment. Cell density was calculated as the sum of flipped and unflipped (wild-type) memory array as determined by qPCR on DNA isolated from fecal samples. Results were normalized to the weight of fecal material analyzed. For day 3 "Chow" samples, n=3. For all other days, n=6 for both treatment groups. For A-C, individual points represent independent biological replicates and the line represents the mean of the group.

DETAILED DESCRIPTION OF THE INVENTION

To date, multiple microorganisms have served as chassis for engineered microbial therapies of human disease. However, compared to organisms such as *E. coli* and *L. lactis*, which undergo depletion or clearance within days of administration, *Bacteroides* populations exhibit low variation in abundance and long-term colonization. Nonetheless, few genetic parts and inducible systems are available for *B. thetaiotaomicron*, for example, and its relatives due, in part, to unique promoter and RBS architectures in *Bacteroides*, which have precluded the direct incorporation of genetic systems developed in other organisms. For example, unlike most other prokaryotes, the unique major sigma factor in *Bacteroides* binds to a −33/−7 consensus sequence (TTTG/TAnnTTTG), the strength of translation initiation is poorly correlated with the level of ribosome binding site (RBS) complementarity to the 16S rRNA of the host organism, and compared to the *E. coli* RBS, *Bacteroides* RBS strength is more sensitive to secondary structures, depleted in GC content, and predicted to rely more heavily on interactions with ribosomal protein S1. Further, promoter and RBS characterization have employed several reporter outputs, preventing direct comparison of parts. A lack of genetic part libraries hinders the introduction of multi-gene pathways, such as those that could produce a metabolic product designed to treat disease.

Figure 1A:
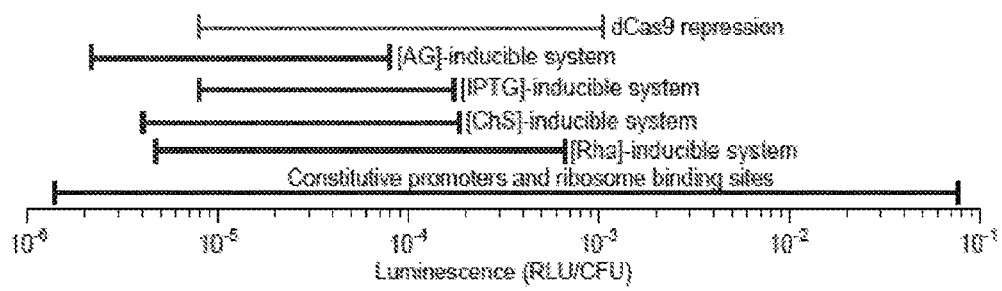
FIGS. 1A-1G. Genetic parts to control expression in *B. thetaiotaomicron*.

The present disclosure provides, in some aspects, a set of genetic tools for precise and robust engineering of *Bacteroides* (e.g., *B. thetaiotomicron*) or *Parabacteroides* for microbiome applications (as well as other applications). Provided herein is a library of biological parts, comprised of constitutive promoters, inducible promoters, and ribosomal binding sites (RBSs) that each span output dynamic ranges over several orders of magnitude (FIG. 1A). Constitutive promoters and RBSs were used to characterize the input expression levels required to generate recombinase-based DNA-encoded memory in *B. thetaiotaomicron*, for example. Externally switchable DNA-based memory devices were then constructed by integrating inducible promoters with recombinases. Additionally, inducible promoters were used to control CRISPRi-based regulation of synthetic and endogenous genes. Finally, multiple of regulatory tools provided herein were integrated together and their proper in vivo function validated within *B. thetaiotomicron* that colonized the gut of mice. With this toolbox of genetic parts, *Bacteroides* (e.g., *B. thetaiotaomicron*) or *Parabacteroides* can be used as a platform for predictable gene expression and circuit design for microbiome engineering.

*Bacteroides* and *Parabacteroides*

*Bacteroides* is a genus of Gram-negative, non-spore-forming, anaerobic, and rod-shaped bacteria. They have an outer membrane, a peptidoglycan layer, and a cytoplasmic membrane. The main by-products of their anaerobic respiration are acetic acid, isovaleric acid, propionic acid and succinic acid. They are involved in many important metabolic activities in the human colon including fermentation of carbohydrates, utilization of nitrogenous substances, and biotransformation of bile acids and other steroids. Most intestinal bacteria are saccharolytic, which means that they obtain carbon and energy by hydrolysis of carbohydrate molecules.

The genomes of the circular chromosomes of many *Bacteroides* species and strains have been studied; research is being done on sequencing *Bacteroides* species in order to understand their pathogenic properties. All *Bacteroides* have G-C composition of 40-48%. Much of the genome is controlled by sigma factors which respond to environmental factors. There have been a total of three genome projects done on two different species of *Bacteroides*. The three genomes sequenced were that of *Bacteroides* thetaiotaomicron VPI-5482, *Bacteroides fragilis* YCH46, and *Bacteroides fragilis* NCTC 9343. Information and a schematic representation of the *Bacteroides thetaiotaomicron* VPI-5482 chromosome can be found at National Center for Biotechnology Information (NCBI).

Engineered nucleic acids of the present disclosure may be introduced into a variety of different organisms, including *Bacteroides*. Examples of species of *Bacteroides* contemplated herein include, without limitation, *B. acidifaciens, B. caccae, B. distasonis, B. gracilis, B. fragilis, B. dorei, B. oris, B. ovatus, B. putredinis, B. pyogenes, B. stercoris, B.*

*suis, B. tectus, B. thetaiotaomicron, B. vulgatus, B. eggerthii, B. merdae, B. stercoris*, and *B. uniformis*.

Engineered nucleic acids of the present disclosure may also be introduced into *Parabacteroides* (Sakamoto M and Benno Y. *Int J Syst Evol Microbiol*. 2006 July; 56 (Pt 7):1599-605, incorporated by reference), which is closely related to *Bacteroides*. Examples of species of *Parbacteroides* contemplated herein include, without limitation, *P. chartae, P. chinchilla, P. distasonis, P. faecis, P. goldsteinii, P. gordonii, P. johnsonii*, and *P. merdae*.

Engineered Nucleic Acids

A "nucleic acid" is at least two nucleotides covalently linked together, and in some instances, may contain phosphodiester bonds (e.g., a phosphodiester "backbone"). An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with naturally-occurring nucleic acid molecules. Recombinant and synthetic nucleic acids also include those molecules that result from the replication of either of the foregoing.

In some embodiments, a nucleic acid of the present disclosure is considered to be a nucleic acid analog, which may contain, at least in part, other backbones comprising, for example, phosphoramide, phosphorothioate, phosphorodithioate, O-methylphophoroamidite linkages and/or peptide nucleic acids. A nucleic acid may be single-stranded (ss) or double-stranded (ds), as specified, or may contain portions of both single-stranded and double-stranded sequence. In some embodiments, a nucleic acid may contain portions of triple-stranded sequence. A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine.

Nucleic acids of the present disclosure may include one or more genetic elements. A "genetic element" refers to a particular nucleotide sequence that has a role in nucleic acid expression (e.g., promoter, enhancer, terminator) or encodes a discrete product of an engineered nucleic acid (e.g., a nucleotide sequence encoding a guide RNA, a protein and/or an RNA interference molecule).

Nucleic acids of the present disclosure may be produced using standard molecular biology methods (see, e.g., Green and Sambrook, Molecular Cloning, *A Laboratory Manual*, 2012, Cold Spring Harbor Press).

In some embodiments, nucleic acids are produced using GIBSON ASSEMBLY® Cloning (see, e.g., Gibson, D. G. et al. *Nature Methods*, 343-345, 2009; and Gibson, D. G. et al. *Nature Methods*, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

In some embodiments, a compressed biosynthetic pathway is delivered to a cell on a vector. A "vector" refers to a nucleic acid (e.g., DNA) used as a vehicle to artificially carry genetic material (e.g., an engineered nucleic acid) into a cell where, for example, it can be replicated and/or expressed. In some embodiments, a vector is an episomal vector (see, e.g., Van Craenenbroeck K. et al. *Eur. J. Biochem*. 267, 5665, 2000, incorporated by reference herein). A non-limiting example of a vector is a plasmid (e.g., FIG. 3). Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector.

Genetic Elements

Expression of engineered nucleic acids is driven by a promoter operably linked to a nucleic acid containing, for example, a nucleic acid encoding a molecule of interest. A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof.

Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal of the present disclosure is anhydrotetracycline (aTc), which is a derivative of tetracycline that exhibits no antibiotic activity and is designed for use with tetracycline-controlled gene expression systems, for example, in bacteria.

In some embodiments, an inducer signal of the present disclosure is isopropyl β-D-1-thiogalactopyranoside (IPTG), which is a molecular mimic of allolactose, a lactose metabolite that triggers transcription of the lac operon, and it is therefore used to induce protein expression where the gene is under the control of the lac operator. IPTG binds to the lac repressor and releases the tetrameric repressor from the lac operator in an allosteric manner, thereby allowing the transcription of genes in the lac operon, such as the gene coding for beta-galactosidase, a hydrolase enzyme that catalyzes the hydrolysis of β-galactosides into monosaccharides. The sulfur (S) atom creates a chemical bond which is non-hydrolyzable by the cell, preventing the cell from metabolizing or degrading the inducer. IPTG is an effective inducer of protein expression, for example, in the concentration range of 100 μM to 1.0 mM. Concentration used depends on the strength of induction required, as well as the genotype of cells or plasmid used. If lacIq, a mutant that over-produces the lac repressor, is present, then a higher concentration of IPTG may be necessary. In blue-white screen, IPTG is used together with X-gal. Blue-white screen allows colonies that have been transformed with the recombinant plasmid rather than a non-recombinant one to be identified in cloning experiments.

Other inducible promoter systems are known in the art and may be used in accordance with the present disclosure.

In some embodiments, inducible promoters of the present disclosure function in prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated E. coli promoters such as positively regulated σ70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rhl), Pu, FecA, pRE, cadC, hns, pLas, pLux), σS promoters (e.g., Pdps), σ32 promoters (e.g., heat shock) and σ54 promoters (e.g., glnAp2); negatively regulated E. coli promoters such as negatively regulated σ70 promoters (e.g., Promoter (PRM+), modified lamdba Prm promoter, TetR-TetR-4C P(Las) TetO, P(Las) CIO, P(Lac) IQ, RecA_Dlex-O_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/ Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), σS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated *B. subtilis* promoters such as repressible *B. subtilis* GA promoters (e.g., Gram-positive IPTG-inducible, Xyl, hyper-spank) and σB promoters. Other inducible microbial promoters may be used in accordance with the present disclosure.

A "ribosomal binding site (RBS)" is a sequence on mRNA that is bound by the ribosome when initiating protein translation. The ribosome searches for this site and binds to it through base-pairing of nucleotides. Once the ribosome has bound, it recruits initiation factors and begins the translation process. *Bacteroides* possess a unique RBS where homology to the 16S rRNA does not play a role in the strength of translation initiation.

The present disclosure contemplates a variety of RBSs including, without limitation, those listed in Table 2.

Recombinases

A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. For example, in some embodiments, *Bacteroides* cells of the present disclosure may be engineered to comprise at least two engineered nucleic acids, comprising a region containing a promoter and a nucleotide sequence encoding a ribosomal binding site (RBS) operably linked to a nucleotide sequence encoding a recombinase, and the other comprising a promoter and a nucleotide sequence encoding a RBS operably linked to a nucleotide sequence encoding a molecule of interest, wherein the nucleotide sequence encoding the molecule of interest is flanked by a pair of cognate recombinase recognition sequences. In such embodiments, expression of the molecule of interest is regulated by recombinase activity, or inactivity, of the other circuit.

Recombinases can be classified into two distinct families: serine recombinases (also referred to herein as serine integrases) and tyrosine recombinases (also referred to herein as tyrosine integrases), based on distinct biochemical properties. Serine recombinases and tyrosine recombinases are further divided into bidirectional recombinases and unidirectional recombinases. Examples of bidirectional serine recombinases for use herein include, without limitation, β-six, CinH, ParA and γδ; and examples of unidirectional serine recombinases include, without limitation, Int1, Int8, Int9, Int12, Bxb1, φkC31, TP901, TG1, φBT1, R4, φRV1, φFC1, MR11, A118, U153 and gp29. Examples of bidirectional tyrosine recombinases for use herein include, without limitation, Cre, FLP, and R; and unidirectional tyrosine recombinases include, without limitation, Lambda, HK101, HK022 and pSAM2. The serine and tyrosine recombinase names stem from the conserved nucleophilic amino acid residue that the recombinase uses to attack the DNA and which becomes covalently linked to the DNA during strand exchange.

The outcome of recombination depends, in part, on the location and orientation of two short repeated DNA sequences that are to be recombined, typically less than 30 bp long. Recombinases bind to these repeated sequences, which are specific to each recombinase, and are herein referred to as "recombinase recognition sequences." Thus, as used herein, a recombinase is "specific for" a recombinase recognition sequence when the recombinase can mediate inversion or excision between the repeated nucleotide sequences. As used herein, a recombinase may also be said to recognize its "cognate recombinase recognition sequences," which flank an intervening genetic element (e.g., promoter, terminator, or nucleotide sequence encoding the molecule of interest). A genetic element is said to be "flanked" by recombinase recognition sites when the element is located between and immediately adjacent to two repeated nucleotide sequences.

Recombinases can also be classified as irreversible or reversible. As used herein, an "irreversible recombinase" refers to a recombinase that can catalyze recombination between two complementary recombination sites, but cannot catalyze recombination between the hybrid sites that are formed by this recombination without the assistance of an additional factor. Thus, an "irreversible recognition site" refers to a recombinase recognition site that can serve as the first of two nucleotide recognition sequences for an irreversible recombinase and that is modified to a hybrid recognition site following recombination at that site. A "complementary irreversible recognition site" refers to a recombinase recognition site that can serve as the second of two nucleotide recognition sequences for an irreversible recombinase and that is modified to a hybrid recombination site following homologous recombination at that site.

Irreversible recombinases, and nucleic acids that encode the irreversible recombinases, are described in the art and can be obtained using routine methods. Examples of irreversible recombinases include, without limitation, phiC31 (φC31) recombinase, coliphage P4 recombinase (Ow & Ausubel, *J. Bacteriol.* 155, 704-713 (1983)), coliphage lambda integrase (Lorbach et al., *J. Mol. Biol.*, 296, 1175-81 (2000)), *Listeria* A118 phage recombinase (Loessner et al., *Mol. Micro.* 35, 324-340 (2000)), and actinophage R4 Sre recombinase (Matsuura et al., *J Bacteriol.* 178, 3374-3376 (1996)), HK101, HK022, pSAM2, Bxb1, TP901, TG1, φBT1, φRV1, φFC1, MR11, U153 and gp29.

Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

In some embodiments, the recombinase is serine recombinase. Thus, in some embodiments, the recombinase is considered to be irreversible. In some embodiments, the recombinase is a tyrosine recombinase. Thus, in some embodiments, the recombinase is considered to be reversible.

The recombinases provided herein are not meant to be exclusive examples of recombinases that can be used in embodiments of the present disclosure. The complexity of the engineered nucleic acids of the present disclosure can be expanded by mining databases for new orthogonal recombinases or designing synthetic recombinases with defined DNA specificities (Groth, A. C. & Calos, M. P. *J Mol Biol* 335, 667-678, (2004); Gordley, R. M., et al. *Proc Natl Acad Sci USA* 106, 5053-5058 (2009)). Other examples of recombinases that are useful in the engineered nucleic acids described herein are known to those of skill in the art, and any new recombinase that is discovered or generated is expected to be able to be used in the different embodiments of the present disclosure.

Therapeutic, Prophylactic and Diagnostic Molecules

The tools provided herein may be used to express, inhibit expression of, or reduce expression of a molecule of interest (e.g., a gene or protein of interest). A molecule, herein, may be, for example, any molecule that can be used to provide benefit to a subject (including without limitation prophylactic or therapeutic benefit) or that can be used for diagnosis and/or detection (for example, imaging) in vitro or in vivo.

In some embodiments, a "nucleotide sequence encoding a molecule of interest" is a nucleotide sequence encoding a protein of interest. Proteins of interest include, for example, antibodies, single chain antibodies, antibody fragments, enzymes, co-factors, receptors, ligands, transcription factors and other regulatory factors, antigens, cytokines and chemokines.

Aspects of the present disclosure provide methods of treating a condition in a subject (e.g., a human subject) comprising administering to a subject a *Bacteroides* bacterium, as described herein. In some embodiments, the *Bacteroides* bacterium comprises (a) an engineered nucleic acid comprising a region containing a promoter and a nucleotide sequence encoding a ribosomal binding site (RBS) operably linked to a nucleotide sequence encoding molecule of interest, such as a therapeutic or prophylactic molecule of interest.

CRISPR Interference

Aspects of the present disclosure provide cells (e.g., *Bacteroides* bacteria) that comprise (a) an engineered nucleic acid comprising a region containing a promoter and a nucleotide sequence encoding a ribosomal binding site (RBS) operably linked to a nucleotide sequence encoding a catalytically-inactive Cas9 nuclease, and (b) an engineered nucleic acid comprising a promoter and a nucleotide sequence encoding a RBS operably linked to a nucleotide sequence encoding a guide RNA, wherein the guide RNA targets a nucleotide sequence encoding a molecule of interest.

CRISPR interference (CRISPRi) is a genetic perturbation technique that permits sequence-specific repression or activation of gene expression. The technique uses catalytically-inactive Cas9 (also referred to as dead Cas9 or dCas9) lacking endonuclease activity to regulate genes in an RNA-guided manner. Targeting specificity is determined by complementary base-pairing of a single guide RNA (sgRNA) to genomic loci, for example. CRISPRi relies on the generation of catalytically inactive Cas9. This is accomplished, for example, by introducing point mutations in the two catalytic residues (D10A and H840A) of the gene encoding Cas9. In doing so, dCas9 is unable to cleave dsDNA but retains the ability to target DNA. Taken together sgRNA and dCas9 provide a minimum system for gene-specific regulation in any organism.

In some embodiments, CRISPRi, as provided herein, is used to inhibit or reduce (e.g., by greater than 10%, such as 20% to 98%, or 50% to 90%) transcription of a molecule of interest (e.g., an endogenous gene of interest) in, for example, a *Bacteroides* bacterium.

Applications

The present disclosure provides, inter alia, a versatile set of genetic technologies for the manipulation of, for example, the abundant gut symbiont *Bacteroides* (e.g., *B. thetaiotaomicron*), expanding on the number and expression range of genetic parts previously available for Bacteroidetes (range: $10^2$) and achieving ranges of expression similar to those of libraries characterized for other gut-associated bacteria, including *E. coli* (range: $10^4$-$10^5$) and lactic acid bacteria (range: $10^3$).

For microbiome engineering applications, the ability to precisely modulate gene expression in commensal organisms may enable functional studies of the microbiome, non-invasive monitoring of in vivo environments, and long-term targeted therapeutics. For example, the constitutive and inducible systems, integrases, and CRISPRi regulators, as provided herein, may be integrated for higher-order computation in *B. thetaiotaomicron*. These engineered commensals may be used to map the dose-dependent and temporal effects of specific surface polysaccharides or heterologous pathways on colonization and maintenance of the gut microbiota and on host health. Higher-order combinations of inducible promoters linked with integrases may achieve Boolean logic with embedded cellular memory, enabling surveillance of the gut environment. Furthermore, environmental sensing coupled with precision expression control of heterologous pathways in *B. thetaiotaomicron* may be exploited, in some embodiments, for on-demand, localized delivery of therapeutic molecules. The present disclosure also shows that the CRISPRi system can be used to dynamically manipulate bacterial processes in *Bacteroides* (e.g., *B. thetaiotaomicron*) by targeting endogenous genes. dCas9-mediated repression may be induced, for example, in a commensal library of *Bacteroides* (e.g., *B. thetaiotaomicron*) harboring distinct guide RNAs to identify genes required for *Bacteroides* (e.g., *B. thetaiotaomicron*) maintenance or interspecies interactions, for example. With these genetic resources, *Bacteroides* (e.g., *B. thetaiotaomicron*) is a useful platform for cellular sensing, computation and actuation at the host-microbe interface in the gut.

EXAMPLES

Example 1. Landing Pads for Genetic Part and Device Characterization

Figure 1B:
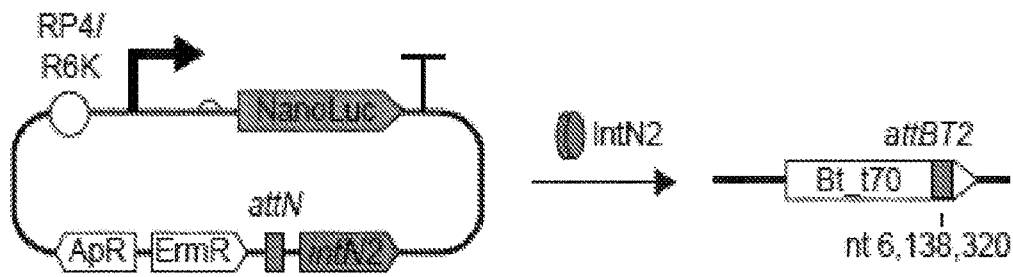

All genetic parts in this study were characterized using the integration vector pNBU2 to ensure genetic stability of the constructs (FIG. 1B). The pNBU2 plasmid encodes the intN2 tyrosine integrase, which mediates sequence-specific recombination between the attN site of pNBU2 and one of two attBT sites located in the 3' ends of the two tRNA$^{Ser}$ genes, BT_t70 and BT_t71, on the *B. thetaiotaomicron* chromosome (FIG. 1B). Insertion of the pNBU2 plasmid inactivates the tRNA$^{Ser}$ gene, and simultaneous insertion into both BT_t70 and BT_t71 is unlikely due to the essentiality of tRNA$^{Ser}$. pNBU2-based vectors have been used for single-copy complementation in *B. thetaiotaomicron* in in vitro studies (Koropatkin N M et al. *Nat. Rev. Microbiol.* 10:323-35, 2012) and in vivo mouse models (Martens E C et al. *Cell Host Microbe* 4:447-57, 2008).

*B. thetaiotaomicron* genetic parts were characterized with NanoLuc luciferase (Hall M P et al. *ACS Chem. Biol.* 7:1848-1857, 2012), which is a small (19 kDa) modified shrimp luciferase. Efforts to use members of the green fluorescent protein family and a FMN-based fluorescent reporter were not successful. NanoLuc oxidizes the exogenously-added substrate furimazine to produce glow-type bioluminescence ($E_{max}$=460 nm) with a signal half-life of 2 hr. By comparison, bacterial luciferase LuxAB (79 kDa)

exhibited rapid signal decay when used to characterize gene expression in *Bacteroides* (Mastropaolo M D et al. *Microbiology* 155:2683-93, 2009).

Example 2. Expression Control Through Promoter and RBS Design

Figure 1C:
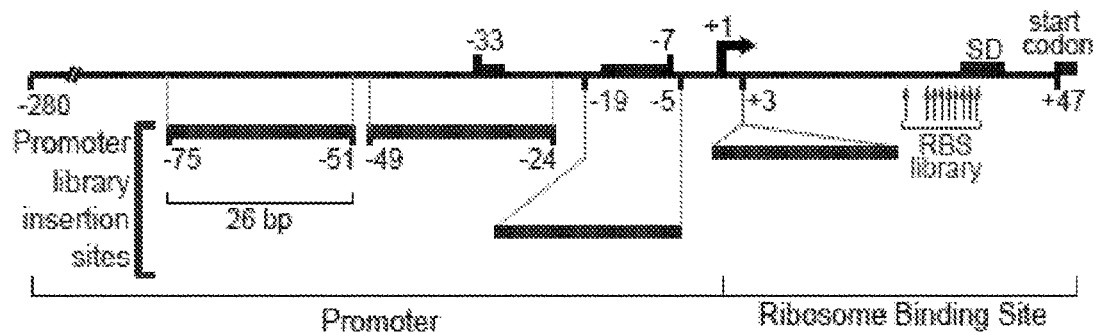
Figure 1D:
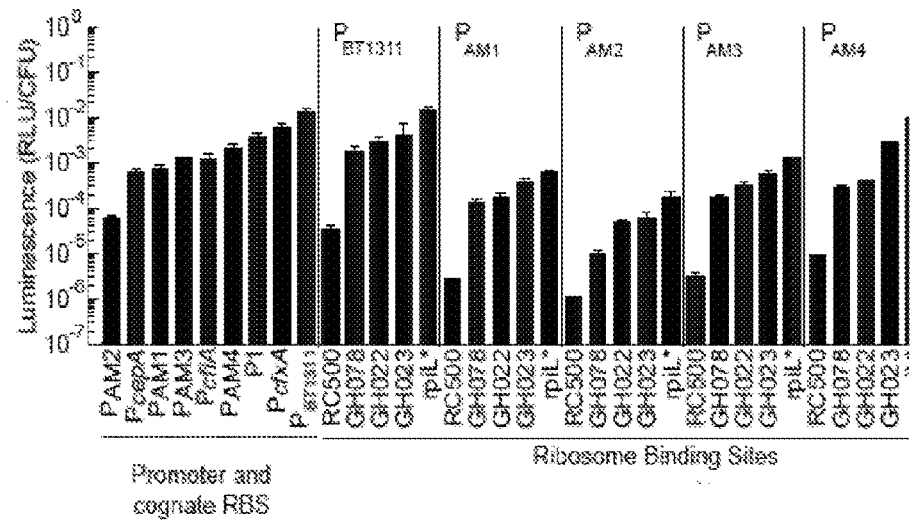

To expand the range of constitutive gene expression that can be implemented in *Bacteroides*, promoter-RBS combinations were constructed and characterized (FIG. 1C). Four promoter variants were constructed based on the constitutive promoter for the *B. thetaiotaomicron* housekeeping sigma factor BT1311 ($P_{BT1311}$) (Vingadassalom D, et al. *Mol. Microbiol.* 56:888-902, 2005). Specifically, a 26-bp sequence was substituted or inserted into $P_{BT1311}$ in regions composing and surrounding the −33 and −7 promoter sequences (FIGS. 6A-6B). Promoter activity is affected by mutations in these regions (Bayley D P, et al. *FEMS Microbiol. Lett.* 193:149-54, 2000) or the equivalent regions in the promoters of other bacteria. The resulting promoters, designated $P_{AM1}$, $P_{AM2}$, $P_{AM3}$, and $P_{AM4}$, retained the BT1311 RBS and were used to control expression of the NanoLuc reporter in the pNBU2 vector backbone (Wang J, et al. *J. Bacteriol.* 182:3559-3571, 2000). The $P_{AM}$ promoters spanned a 20-fold range of expression and had decreased expression levels relative to the $P_{BT1311}$ parent promoter. For comparison to prior work, the activities of promoter-RBS pairs, $P_{cfxA}$, $P_{cfiA}$, $P_1$ and $P_{cepA}$ (Wegmann U, et al. *Appl. Environ. Microbiol.* 79:1980-9, 2013; Parker A C, et al. *Antimicrob. Agents Chemother.* 37:1028-1036, 1993; Rogers M B, et al. *J. Bacteriol.* 176:4376-4384, 1994; and Goto T, et al. *J. Antibiot.* (Tokyo). 66:239-242, 2013) were also measured (FIG. 1D).

The $P_{AM}$ promoters were then combined with RBSs of varying strength to increase the range of expression levels. The RBS is poorly understood in *Bacteroides* species, and the presence of a consensus Shine-Delgarno (SD) sequence based on the *Bacteroides* 16S rRNA does not greatly enhance translation initiation. RBSs GH022, GH023, and GH078 (Wegmann U, et al. *Appl. Environ. Microbiol.* 79:1980-9, 2013) were first used. As reported, this set of RBSs covered a limited range of expression spanning less than one order of magnitude (FIG. 1D). Given that ribosomal proteins are predicted to be the most highly expressed proteins in most bacterial species, a ribosomal protein RBS (rpiL* in FIG. 1D) was selected to increase the range of available RBSs. In addition, a weak *B. thetaiotaomicron* RBS (RC500) was constructed (FIG. 1D). The RBS library consisting of RC500, GH022, GH023, GH078, and rpiL* spanned a >$10^2$-fold range when paired with each $P_{AM}$-derived promoter. When combined, these $P_{AM}$ promoters and RBSs could achieve expression levels over a $10^4$-fold range.

Figure 1E:
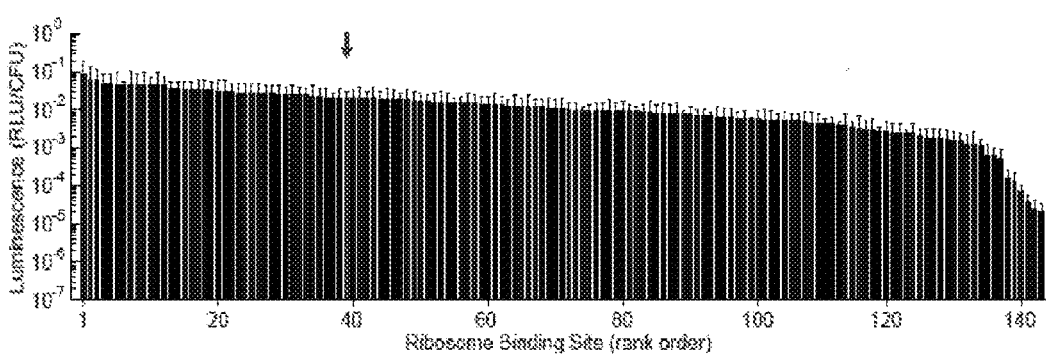

To identify a set of RBSs for fine-tuning gene expression in *B. thetaiotaomicron*, three randomized RBS libraries targeting the most conserved positions of the *Bacteroides* ribosomal protein RBSs were generated. Libraries were based on the rpiL* RBS and were characterized under the control of $P_{BT1311}$. The low GC content (14%) of the rpiL* RBS reduced the likelihood of introducing secondary structures during randomization. For each library, 3 nucleotides in and around the rpiL* RBS Shine Delgarno sequence were targeted. These positions are within or near the RBS region predicted to interact with the ribosomal 51 protein (nt −21 to −11 relative to the start codon of NanoLuc, FIG. 1C) (Bloom S M, et al. *Cell Host Microbe* 9:390-403, 1991). Coverage of 67-80% of the 64 potential members as achieved in each library, resulting in 142 RBS sequences (FIG. 1E, Table 1). These RBSs were screened and sequenced and a set of 8 was identified that span $10^3$-fold expression range in approximately even increments (Table 2).

Figure 1F:
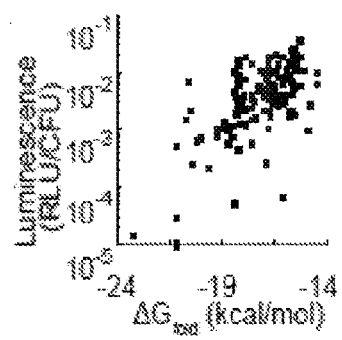
Figure 1G:
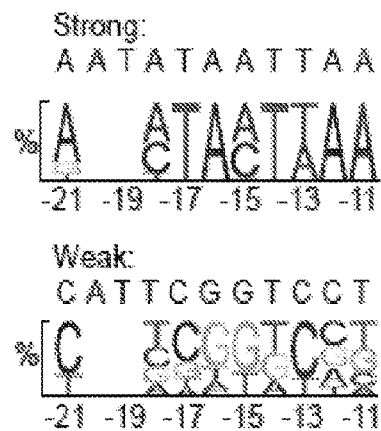

RBS strength in *Bacteroides* species is reported to be sensitive to secondary structure and GC content, likely due to the inability to form mRNA-16S rRNA interactions. Only a weak positive correlation was observed between the minimum free energy of RBS folding and expression of the NanoLuc reporter ($r^2$=0.19) in the rpiL* library (FIG. 1F). To visualize the impact of GC content on RBS strength within this library, frequency logos were generated to compare the frequency of each nucleotide at each diversified position in the target sequence relative to the frequency of that nucleotide in the full library. As seen in FIG. 1G, the strongest RBSs were GC-depleted relative to the overall library, and the weakest RBSs sequences had a higher likelihood of containing a G or C at most positions tested. These data support findings that A/U rich regions upstream of the SD sequence enhance RBS strength. The RBS libraries provided herein highlight the distinct GC content depletion of *Bacteroides* RBSs compared to other bacterial species, which results in part failure when constructs are transferred into *Bacteroides* from other species.

Example 3. Genetic Sensors and Inducible Systems

Figure 2A:
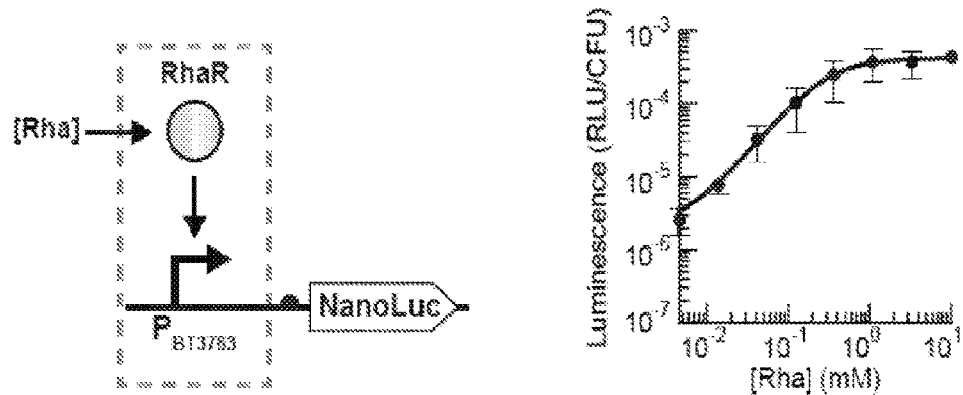

To create inducible systems for use in *B. thetaiotaomicron*, parts from a large repertoire of systems that govern carbohydrate utilization were used, which included cytoplasmic transcription factors, extracytoplasmic function sigma/anti-sigma pairs, and hybrid two-component systems (HTCS), among others (64). In *B. thetaiotaomicron*, rhamnose metabolism is mediated by the AraC/XylS-family transcriptional activator, RhaR, which activates transcription at the $P_{BT3763}$ promoter (Patel E H, et al. *Res. Microbiol.* 159:678-84, 2008). To assay the functionality of $P_{BT3763}$ as an inducible system, 250 bp of the promoter-RBS region was cloned upstream of the start codon of BT3763 into the pNBU2 expression vector to drive expression of NanoLuc. Gene expression was conditional on the concentration of rhamnose and demonstrated a response curve with an output dynamic range of 104-fold (FIG. 2A). Fitting the response curve to a Hill function revealed a threshold K of 0.3 mM and a Hill coefficient n=1.4.

Figure 2B:
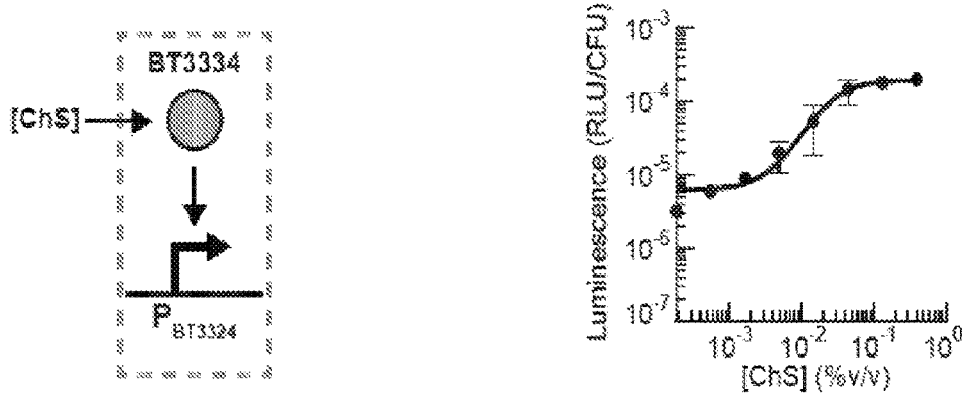

Two-component systems are signal-transduction mechanisms widespread in bacteria for sensing external stimuli. *Bacteroides* sp. possess a unique variant of these systems, called hybrid two-component systems (HTCSs), that incorporate both the sensor histidine kinase and response regulator of classical two-component systems into a single polypeptide chain. Putative HTCSs, BT3334 and BT0267, were identified in transcriptomic studies to control expression of the chondroitin sulfate (ChS)-inducible $P_{BT3324}$ promoter and arabinogalactan (AG)-inducible $P_{BT0268}$ promoter, respectively (64, 83). The promoter regions upstream of the BT3324 and BT0268 genes were used as the basis for two polysaccharide sensors. Chondroitin sulfate induction of $P_{BT3324}$ and arabinogalactan induction $P_{BT0268}$ led to a 60-fold and 29-fold regulation of output gene expression, respectively (FIGS. 2B and 2C).

Figure 7A:
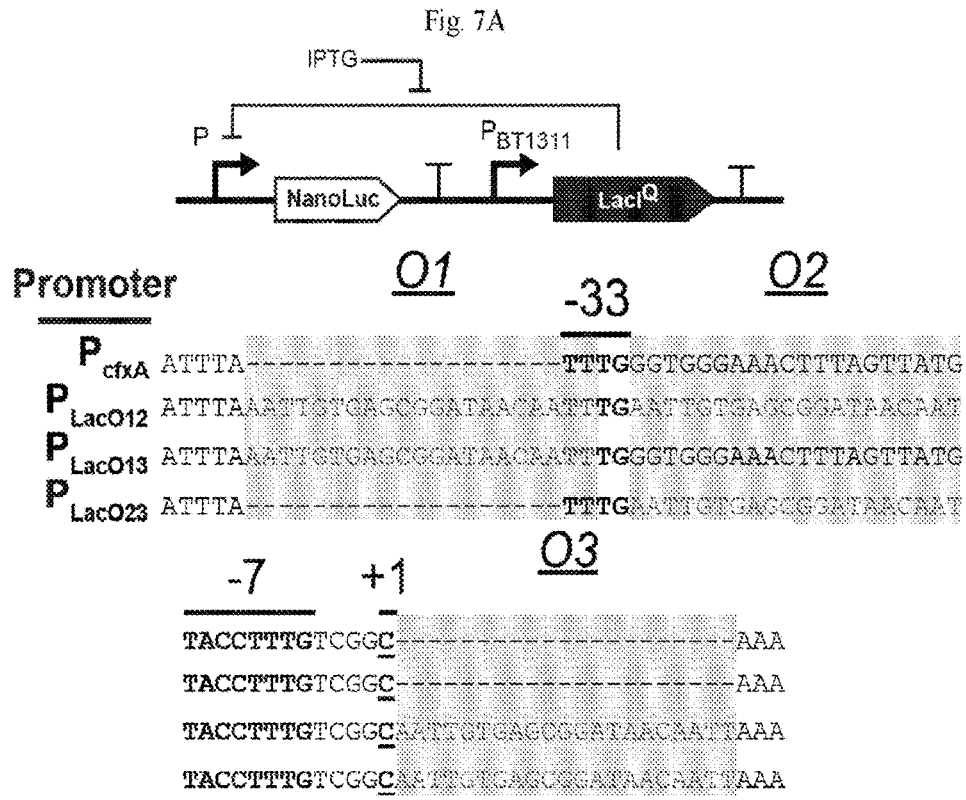
FIGS. 7A-7B. Synthetic IPTG-inducible promoters.
Figure 7B:
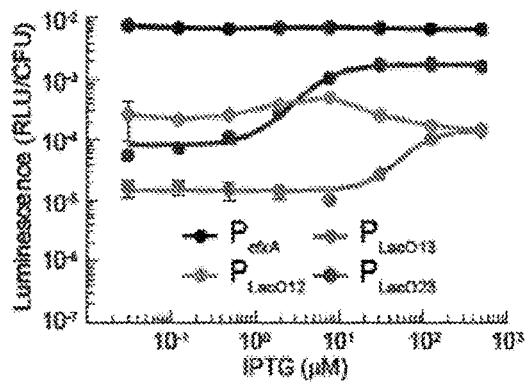

Next, an IPTG-inducible system was developed. Pairs of LacO1 operator sites were inserted in the strong $P_{cfxA}$ promoter in three locations: upstream of the −33 element (O1), between the −33 and −7 elements (O2) or just downstream of the transcription start site (O3) (FIGS. 7A-7B). The LacI$^Q$ repressor was expressed from the strong BT1311 promoter to achieve tight control of NanoLuc expression. Compared to the unmodified $P_{cfiA}$ promoter, the addition of synthetic operator sites diminished the maximum expression of NanoLuc (FIGS. 7A-7B). This strategy produced two IPTG-inducible promoters that with thresholds at K=86 µM ($P_{LacO13}$) and K=6 µM ($P_{LacO23}$). The induction of these systems elicits an 8- and 22-fold change in gene expression, respectively (FIG. 2D).

As the orthogonality of genetic parts is crucial for their simultaneous use, the degree of cross-talk between each inducible system was tested by incubating each engineered strain with the full set of carbohydrate inducers. The inducers themselves bear little structural similarity: rhamnose, a methyl-pentose sugar; ChS, a sulfated glycocosaminoglycan composed of chains of acetylgalactosamine and glucuronic acid residues; AG, a polysaccharide composed of arabinose and galactose units; and IPTG, a molecular mimic of allolactose. Functionally, each inducible system was highly orthogonal to each other, with no cross-reactivity observed with any of the combinations (FIG. 2E).

Example 4. Synthetic Genetic Memory

Figure 3A:
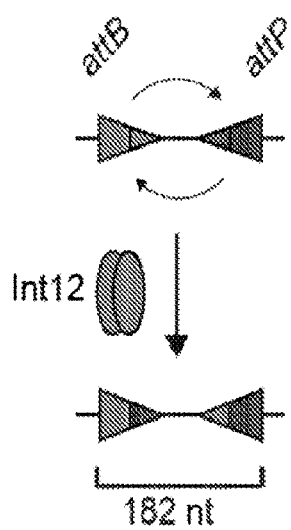
FIGS. 3A-3G. Synthetic genetic memory.

To enable genetic memory in B. thetaiotaomicron, serine integrases were implemented, which permanently invert DNA between two recognition sequences (FIG. 3A). Recently, 11 orthogonal integrases and their recognition sequences were characterized in E. coli (Yang L, et al. Nat. Methods 11, 2014). In this study, a DNA "memory array" composed of a linear concatenation of integrase recognition sequences was used to record the expression of one or multiple integrases in response to a stimulus. Each integrase and its cognate recognition sequence in the memory array functioned as a switch that could be permanently flipped in response to integrase expression.

Figure 3B:
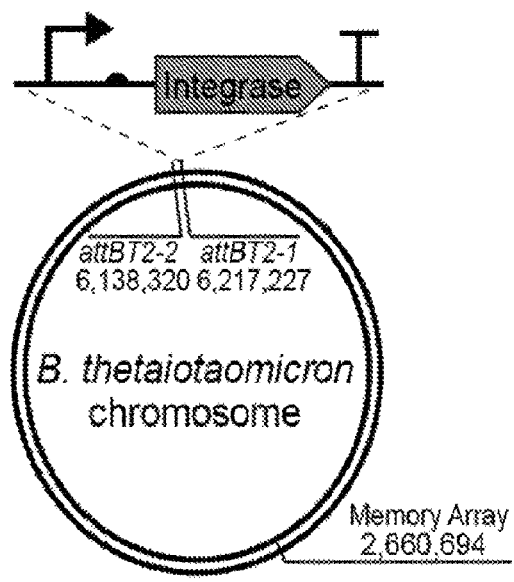
Figure 3C:
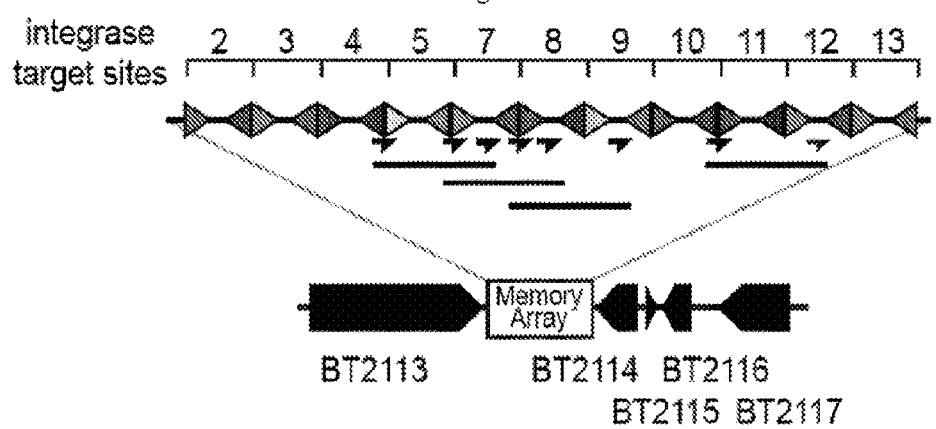
Figure 3D:
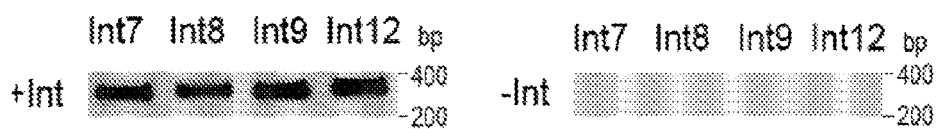
Figure 8A:
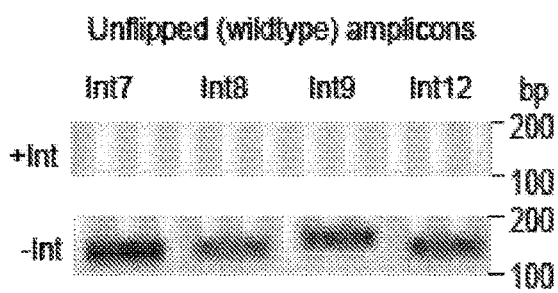
FIGS. 8A-8B. Integrase characterization.

To equip B. thetaiotaomicron with permanent genetic memory, serine integrases that function in B. thetaiotaomicron were first identified by cloning the integrases into a strong constitutive expression vectors ($P_{AM4}$-rpiL*, 1.2× $10^{-2}$ RLU/CFU). Using allelic exchange, the DNA memory array containing the integrase recognition sequences were incorporated into the B. thetaiotaomicron chromosome to provide a stable, single-copy record of DNA inversion (FIGS. 3B and 3C). Integrase expression vectors were conjugated into the B. thetaiotaomicron memory array strain. Genomic DNA was isolated from transconjugants and analyzed by PCR to detect flipping. Four integrases, Intl, Int8, Int9 and Int12, each catalyzed recombination at the respective recognition sequence in the memory array (FIG. 3D), and DNA inversion was not detected in the absence of an integrase (FIG. 8A).

Figure 8B:
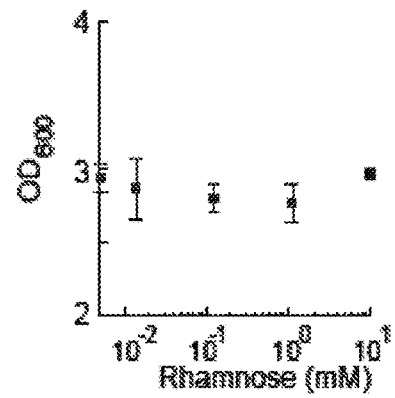

To create an inducible memory switch, Int12 was cloned under the control of the rhamnose-inducible promoter with the rpiL*RBS variant C51 (FIG. 3E) (see also FIG. 1C, Table 1). The Int12 recombinase switch responded to increasing concentrations of rhamnose (FIG. 3F) within 2 hours (FIG. 3G), with no background detected in the absence of inducer. Notably, expression of Int12 did not impact growth of B. thetaiotaomicron, even when maximally expressed (FIG. 8B).

Example 5. CRISPRi-Mediated Gene Knockdown

Figure 4A:
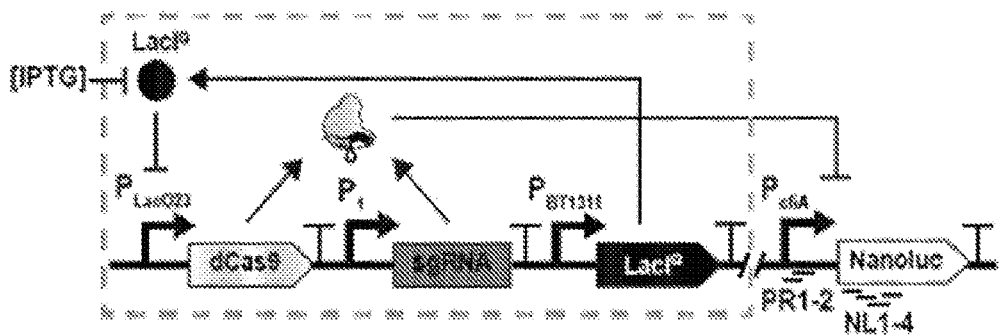
FIGS. 4A-4F. CRISPRi-mediated repression of recombinant and endogenous genes.
Figure 4B:
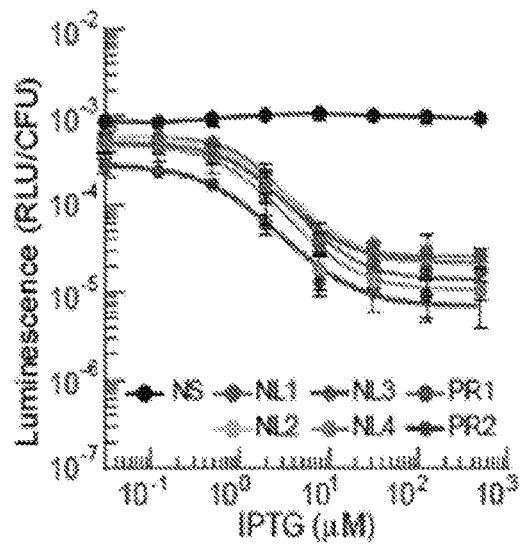
Figure 4C:
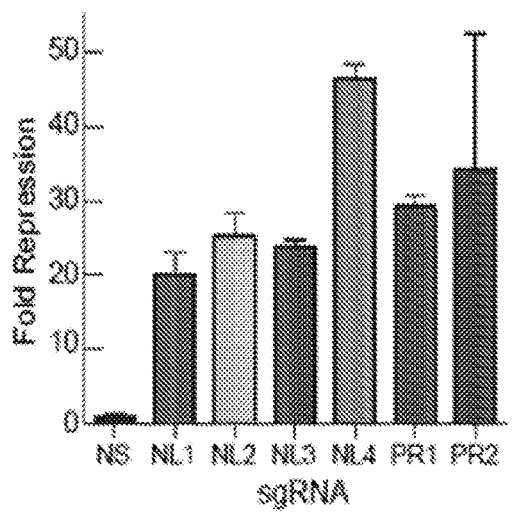
Figure 4D:
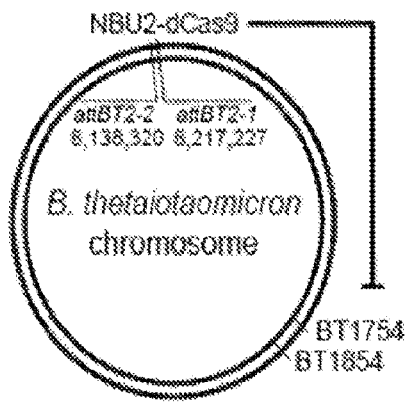

CRISPRi can provide a facile toolbox for constructing synthetic gene circuits and modulating endogenous genes in B. thetaiotaomicron. To demonstrate the use of CRISPRi-mediated gene knockdown for synthetic constructs, a set of guide RNAs (sgRNAs) that control expression of NanoLuc was first created (FIG. 4A). The production of dCas9 was regulated by the IPTG-inducible $P_{LacO23}$ system while sgRNAs were constitutively expressed from the $P_1$ promoter. Four gRNAs targeting the coding sequence of NanoLuc (NL1-4) and two targeting the $P_{cfiA}$ promoter driving NanoLuc expression (PR1-2) were designed (FIG. 4A). A nonsense sgRNA (NS) with no sequence identity to either $P_{cfiA}$ or NanoLuc was used as a negative control. All of the specifically targeted guide RNAs repressed the expression of NanoLuc (FIG. 4B) by 20-45 fold with IPTG induction of dCas9 expression (FIG. 4C), thus implementing genetic NOT gates in B. thetaiotaomicron. The IPTG-to-NanoLuc response function of sgRNAs targeting the coding sequence or promoter exhibited similar Hill coefficients and lower dissociation constants to the IPTG-to-NanoLuc transfer function of the $P_{LacO23}$ promoter on its own (n=1.1 to 1.4; K=0.6 to 1.4 µM IPTG).

Figure 4E:
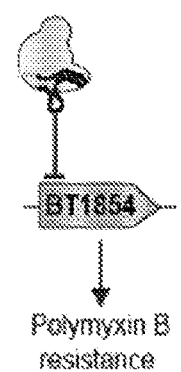

To demonstrate the programmable knockdown of endogenous genes in B. thetaiotaomicron, sgRNAs were designed to target mechanisms implicated in the resilience of Bacteroides in the human microbiota. Resistance to inflammation-associated cationic antimicrobial peptides, such as polymyxin B, is essential for the stability of commensal organisms in the dynamic gut environment. In B. thetaiotaomicron, LpxF, the gene product of BT1854, is required for the dephosphorylation of lipid A that leads to high levels of resistance to antimicrobial peptides. Using the minimum inhibitory concentration (MIC) of polymyxin B as a phenotypic readout, an sgRNA was designed to specifically suppress BT1854 expression. Similar to wild-type (WT) B. thetaiotaomicron, strains containing $dCas9_{NS}$ demonstrated high levels of polymyxin B resistance in the presence or absence of dCas9 induction with IPTG. However, in cells containing the sgRNA targeted against BT1854 ($dCas9_{BT1854}$), the induction of dCas9 with led to sensitization of the cells to polymyxin B treatment, with a 8 to 16-fold decrease in MIC compared to WT and the nonspecific $dCas9_{NS}$ control (FIG. 4E).

Figure 4F:
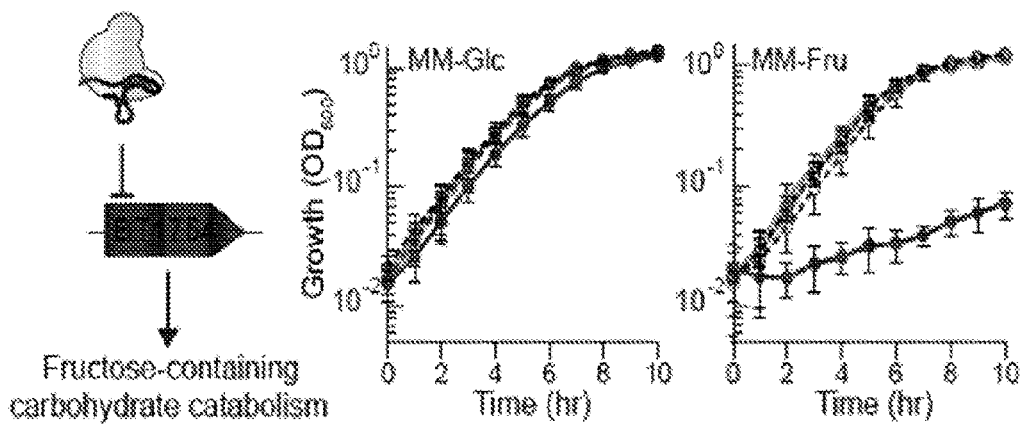

Next, whether dCas9-mediated repression of carbohydrate-utilization pathways could alter the metabolic capabilities of B. thetaiotaomicron was explored, which pathways are important for the bacterium's ability to successfully and persistently colonize the mammalian gut. Fructose-containing carbohydrates are catabolized by the gene products of the BT1757-1763/BT1765 polysaccharide utilization locus, which is subject to regulation by the HTCS sensor, BT1754 (Sonnenburg E D, et al. Cell 141:1241-52, 2010). BT1754 is essential for growth on fructose-containing carbohydrates and genetic inactivation of BT1754 leads to retarded growth in minimal media (MM) containing fructose as the sole carbon source. To modulate the ability of B. thetaiotaomicron to utilize fructose, a specific guide RNA was designed to repress BT1754 and integrated this system into the B. thetaiotaomicron genome along with an IPTG-inducible dCas9 cassette ($dCas9_{BT1754}$). Induction of $dCas9_{BT1754}$ did not affect the growth rate of cells on MM-glucose compared to WT cells and $dCas9_{NS}$. The generation time $G=(\log_{10}2 \cdot t)/\log_{10}(B/B_0) \approx 1$ hr (where t is the time interval, and $B_o$ and B are the initial and final concentrations of bacteria, respectively), indicating that neither dCas9 induction nor repression of BT1754 impacts growth on glucose media (FIG. 4F). However, induction of $dCas9_{BT1754}$ drastically decreased the growth rate of the cells in MM-fructose (G=4.7 hr) while the growth of WT and $dCas9_{NS}$ cells in MM-fructose remained similar (G=1 hr) to growth in MM-glucose (FIG. 4F). Thus, inducible dCas9-mediated repression of endogenous genes can alter both the resistance and metabolic profiles of *B. thetaiotaomicron*.

Figure 9A:
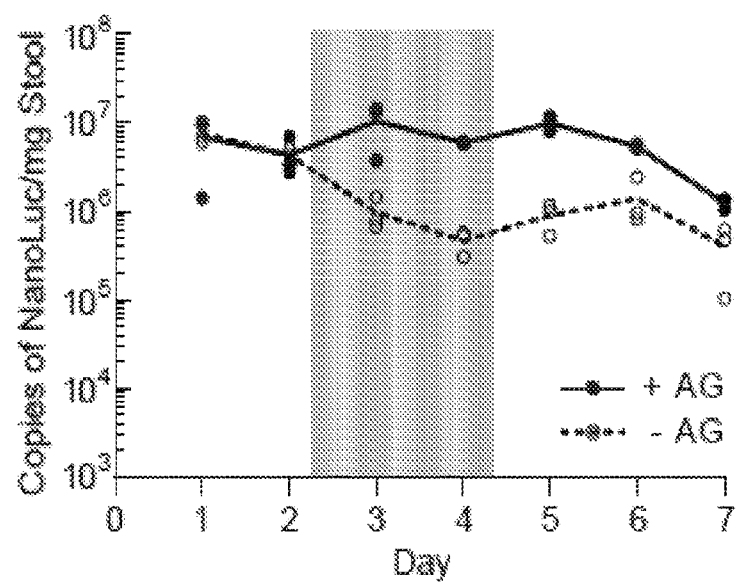
FIGS. 9A-9C. Colonization of the mouse gut with engineered *B. thetaiotaomicron* strains.
Figure 9B:
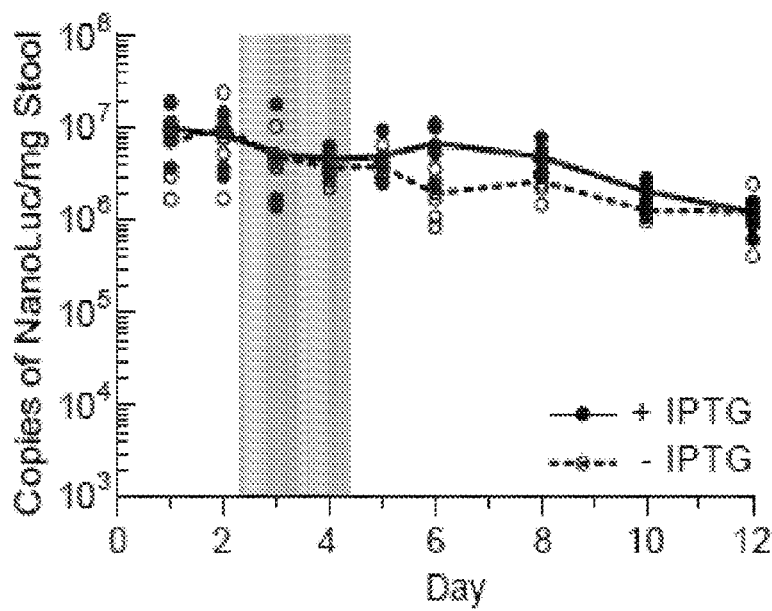
Figure 9C:
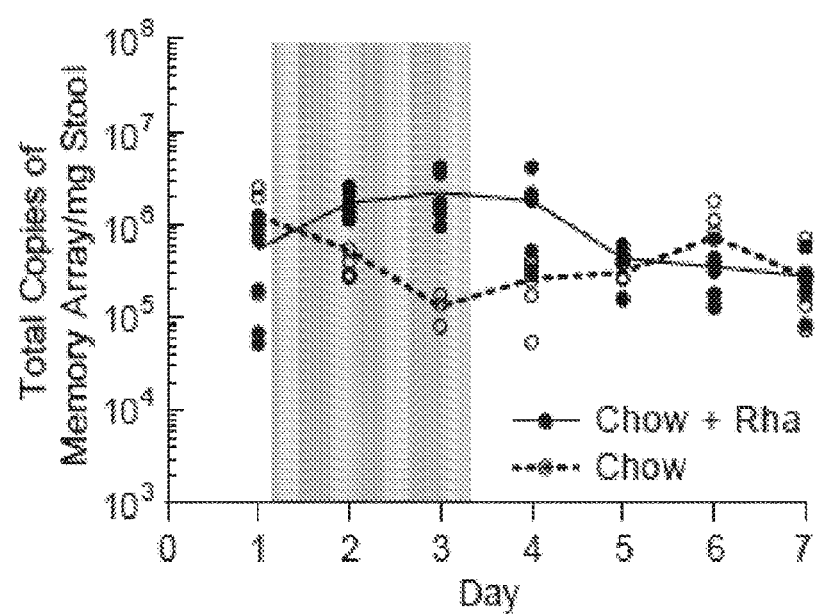

Example 6. Function of Genetic Parts in *B. thetaiotaomicron* Colonizing the Mouse Gut Next investigated was whether the function of the *B. thetaiotaomicron* genetic parts and modules can be maintained in the context of a complex microbiota. As wild-type strains of *Bacteroides* spp. are unable to stably colonize conventional specific-pathogen free (SPF) mice, an antibiotic regimen that promotes *B. thetaiotaomicron* colonization without sterilizing the gut microbiota was employed (FIG. 5A) (Lee S M, et al. *Nature* 501:426-9, 2013; Bloom S M, et al. *Cell Host Microbe* 9:390-403, 2011). A ten-day treatment of animals with ciprofloxacin and metronidazole prior to bacterial inoculation was sufficient to maintain stable and high levels of colonization for the duration of the experiments (up to 12 days tested) (FIGS. 9A-9C).

Using this model, the functionality of the inducible systems were tested, CRISPRi, and integrases in vivo. First, SPF mice were colonized with the strain containing the arabinogalactan-inducible $P_{0268}$ promoter driving expression of NanoLuc (FIG. 9A). Within a day of addition of arabinogalactan to the drinking water of the mice, luciferase activity in fecal pellets increased approximately 75-fold (FIG. 5B). Following removal of inducer from the drinking water, luciferase activity in the fecal pellets of mice fed inducer rapidly returned to baseline, demonstrating tight temporal control of gene expression dependent on arabinogalactan.

To investigate whether more complex genetic circuits perform in the context of the mouse microbiome, the dCas9$_{NL3}$ repressor cascade was evaluated, which is composed of the CRISPRi system as well as the $P_{LacO23}$ IPTG-inducible promoter, within stably colonized *B. thetaiotaomicron*. Within 24 hours of adding IPTG to drinking water, CRISPRi elicited approximately a 20-fold reduction in gene expression compared to the uninduced control (FIG. 5C). The fold repression observed in vivo is similar to that measured in vitro. Luciferase activity returned to baseline 6 days following the removal of IPTG from drinking water. Moreover, expression of dCas9 and NanoLuc did not significantly impact in vivo fitness compared to uninduced controls (FIGS. 9A and 9B). Thus, inducible promoters as well as exogenously regulated CRISPRi can be implemented for on-demand activation or repression of synthetic genetic circuits in members of a mammalian microbiome.

Figure 3E:
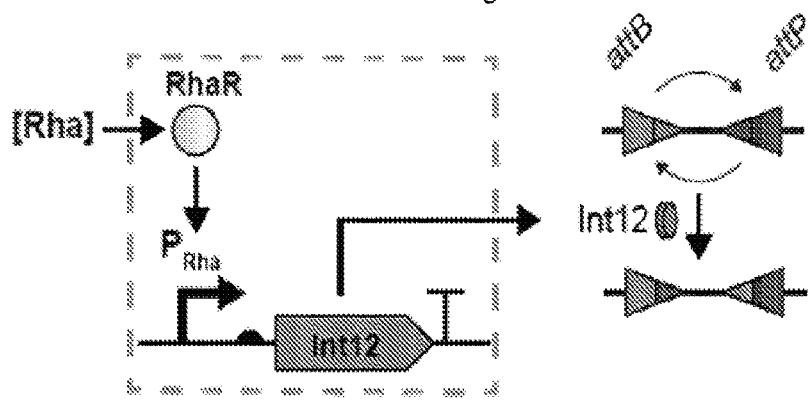
Figure 3F:
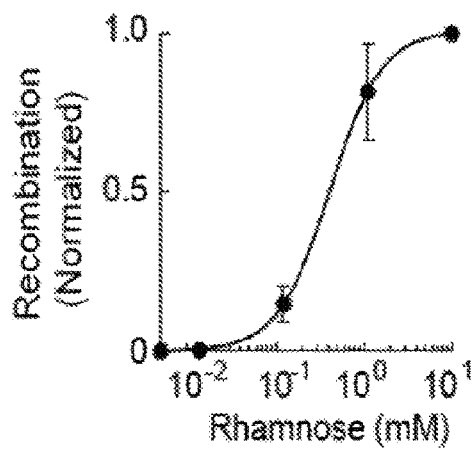
Figure 3G:
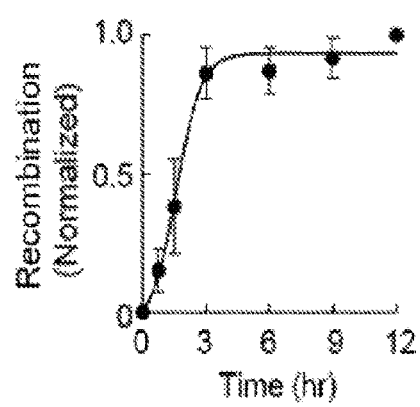
Figure 5D:
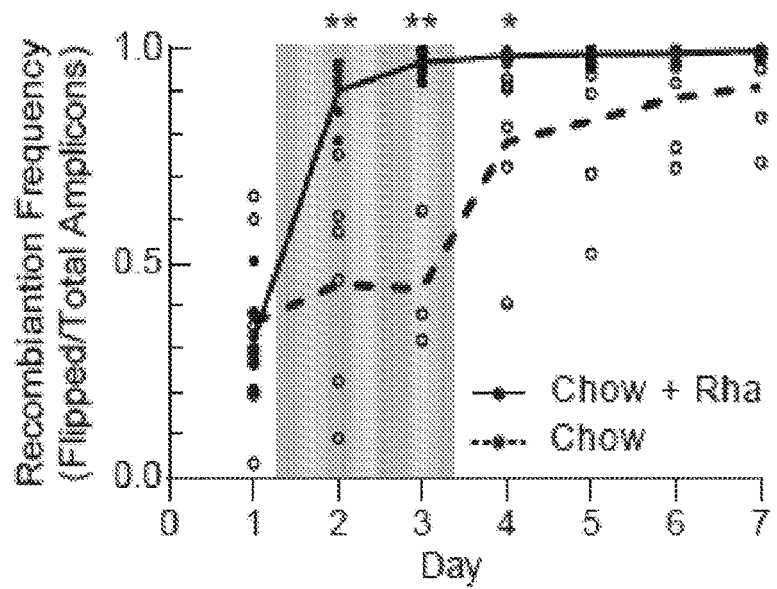

To test the function of recombinases in vivo, mice were colonized with a *B. thetaiotaomicron* strain containing the rhamnose-inducible Int12 integrase memory switch (FIG. 3E). Rhamnose biosynthetic pathways are absent in higher vertebrates, but rhamnose is a common component of the plant and bacterial cell wall. All mice were fed with plant-based chow that was determined to be composed of 0.3% rhamnose (w/w). In addition, after one day of colonization, the drinking water of half of the mice was supplemented with 0.5M rhamnose for two days to further induce the memory switch. Stool was collected over the course of the experiment, and the absolute number of unflipped (wild-type) and flipped Int12 recognition sequences was determined by qPCR using standard curves generated with purified, homogenous template DNA. Recombination frequency is reported as the ratio of flipped to total memory array sequences (FIG. 5D). A background recombination rate of ~11% per day was detected in mice fed on rhamnose-containing chow but not supplemented with rhamnose in their drinking water (FIG. 5D, "Chow"). In mice supplemented with exogenous rhamnose (FIG. 5D, "Chow+Rha"), the recombinase switch achieved >90% flipping in <1 day, a statistically significant increase over mice not supplemented with rhamnose in the water (p<0.01; FIG. 5D). Together, these results indicate that inducible recombinase systems can be implemented within *B. thetaiotaomicron* living in the mouse gut.

Example 7. Generation of pNBU1

Figure 10:
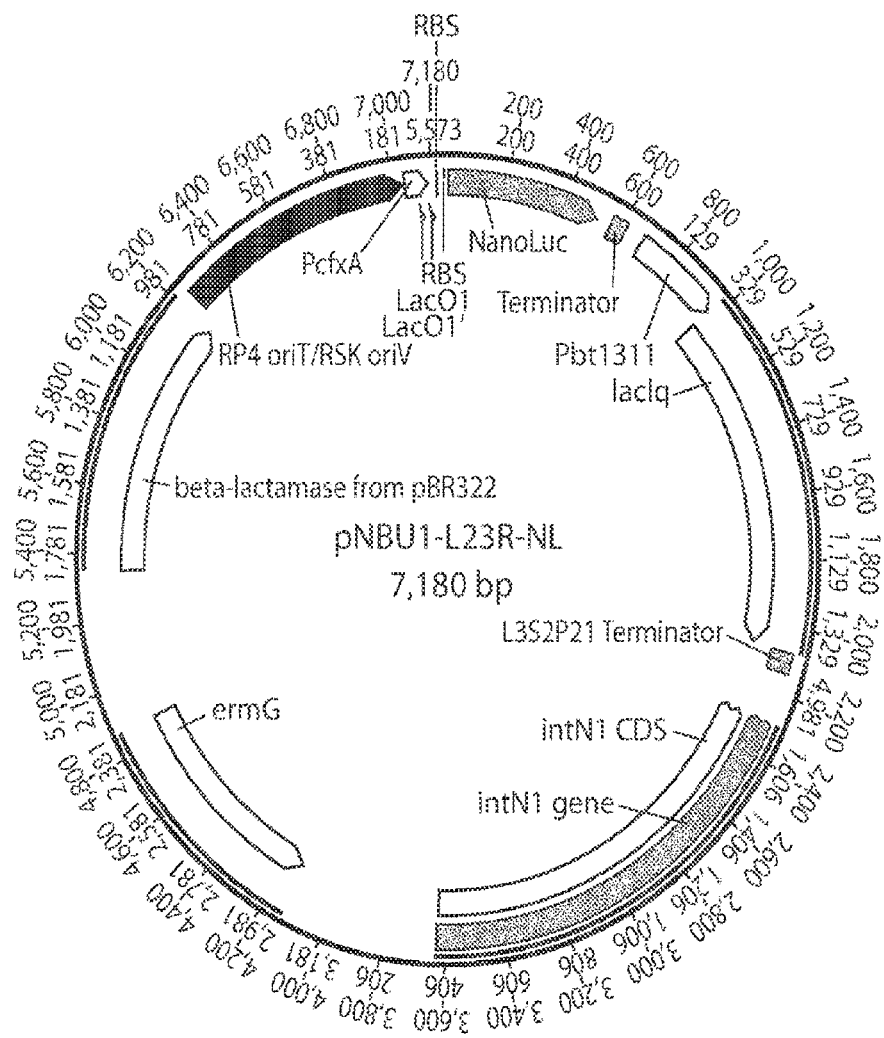
FIG. 10 shows a plasmid map of pNBU1, which includes a NBU1 integrase for insertion into a single site in a *Bacteroides* chromosome.
Figure 11:
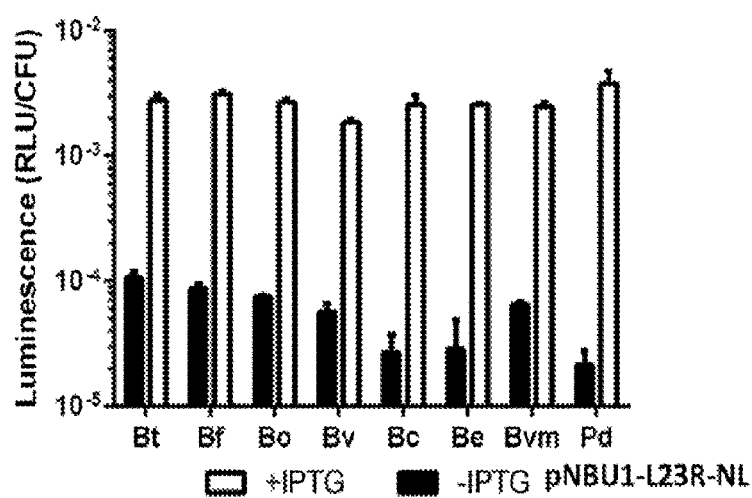
FIG. 11 is a graph showing that pNBU1 may be used to target, for example, *B. thetaiotaomicron, B. fragilis, B. ovatus, B. vulgatus, B. caccae, B. eggerthii, B. vulgatus* and *Parabacteroides distasonis*.

An integration vector, designated pNBU1, was created to introduce recombinant DNA into a wide range of *Bacteroides* species (FIG. 10). IntN1 integrase catalyzes site-specific genomic integration of the plasmid into recipient *Bacteroides* strains. Following transfer of pNBU1, the IntN1 integrase is expressed, binds to its cognate attP site on the plasmid and catalyzes integration of the plasmid backbone at attB sites located in the *Bacteroides* genome. pNBU1 shows a greater host range and efficiency relative to the pNBU2 plasmid, discussed above. pNBU1 is capable of facilitating gene expression in multiple *Bacteroides* spp, including, for example, *B. thetaiotaomicron, B. fragilis, B. ovatus, B. vulgatus, B. caccae, B. eggerthii* and *Parabacteroides distasonis*. Further, pNBU1 comprises a variant of the IntN1 attP site (SEQ ID NO: 207) that exhibits high specificity and low off-target integration events.

TABLE 1

| RBS | Average Luminescence (RLU/CFU) | Average Standard Deviation | RBS Sequence | SEQ ID NO. |
|---|---|---|---|---|
| B1 | 0.090249894 | 0.111388832 | TCCCGCATTTTAAAATAAAATAAATTATTCGTTTAGTTAAACGAAT | 1 |
| B2 | 0.063254655 | 0.081403266 | TCCCGCATTTTAAAATAAAATAAATGATATAATTAATTAAACGAAT | 2 |
| B3 | 0.060832252 | 0.063813202 | TCCCGCATTTTAAAATAAAATAAATAATATAATTAATTAAACGAAT | 3 |
| B4 | 0.051529534 | 0.034223973 | TCCCGCATTTTAAAATAAAATAAATAATTTAATTAATTAAACGAAT | 4 |
| B5 | 0.048254761 | 0.039921888 | TCCCGCATTTTAAAATAAAATAAATTATATAATTAATTAAACGAAT | 5 |

TABLE 1-continued

| RBS | Average Luminescence (RLU/CFU) | Average Standard Deviation | RBS Sequence | SEQ ID NO. |
|---|---|---|---|---|
| B6 | 0.047226545 | 0.049931689 | TCCCGCATTTTAAAATAAAATAAATAATATACTTAATTAAACGAAT | 6 |
| A11 | 0.04718849 | 0.006274175 | TCCCGCATTTTAAAATAAAATAAATTATTATTTTAATTAAACGAAT | 7 |
| B7 | 0.047043161 | 0.062527228 | TCCCGCATTTTAAAATAAAATAAATAATCTACTTAATTAAACGAAT | 8 |
| B8 | 0.046841158 | 0.044979939 | TCCCGCATTTTAAAATAAAATAAATTATTTAATTAATTAAACGAAT | 9 |
| B9 | 0.046340254 | 0.048117599 | TCCCGCATTTTAAAATAAAATAAATTATCTAATTAATTAAACGAAT | 10 |
| C1 | 0.044683993 | 0.028195136 | TCCCGCATTTTAAAATAAAATAAATTATTGATTTAGTTAAACGAAT | 11 |
| B10 | 0.044212731 | 0.052853672 | TCCCGCATTTTAAAATAAAATAAATTATATATTTAATTAAACGAAT | 12 |
| C2 | 0.043308875 | 0.027512352 | TCCCGCATTTTAAAATAAAATAAATTATTACTTTAGTTAAACGAAT | 13 |
| C3 | 0.036766445 | 0.021047641 | TCCCGCATTTTAAAATAAAATAAATTATTACTTTAATTAAACGAAT | 14 |
| A2 | 0.03616262 | 0.021784372 | TCCCGCATTTTAAAATAAAATAAATTATTTTTTTACTTAAACGAAT | 15 |
| C4 | 0.035162979 | 0.022626606 | TCCCGCATTTTAAAATAAAATAAATTATTTATTTAGTTAAACGAAT | 16 |
| C5 | 0.033268624 | 0.023697797 | TCCCGCATTTTAAAATAAAATAAATTATTCATTTAATTAAACGAAT | 17 |
| B11 | 0.033077187 | 0.02879404 | TCCCGCATTTTAAAATAAAATAAATAATGTAATTAATTAAACGAAT | 18 |
| C6 | 0.032629332 | 0.026587549 | TCCCGCATTTTAAAATAAAATAAATTATTAATTTAGTTAAACGAAT | 19 |
| C7 | 0.032494498 | 0.022027997 | TCCCGCATTTTAAAATAAAATAAATTATTAATTTACTTAAACGAAT | 20 |
| C8 | 0.031319702 | 0.02714175 | TCCCGCATTTTAAAATAAAATAAATTATTTATCGAATTAAACGAAT | 21 |
| B12 | 0.031075041 | 0.028444074 | TCCCGCATTTTAAAATAAAATAAATAATATATTTAATTAAACGAAT | 22 |
| C9 | 0.029881822 | 0.019563883 | TCCCGCATTTTAAAATAAAATAAATTATTGCTTTAATTAAACGAAT | 23 |
| A3 | 0.028665204 | 0.020363132 | TCCCGCATTTTAAAATAAAATAAATTATTAGTTTAGTTAAACGAAT | 24 |
| B13 | 0.02746246 | 0.023749498 | TCCCGCATTTTAAAATAAAATAAATGATTAATTAATTAAACGAAT | 25 |
| B14 | 0.027145346 | 0.021119454 | TCCCGCATTTTAAAATAAAATAAATTATCTATTTAATTAAACGAAT | 26 |
| B15 | 0.02694894 | 0.022086946 | TCCCGCATTTTAAAATAAAATAAATGATTTACTTAATTAAACGAAT | 27 |
| B16 | 0.026825139 | 0.018256635 | TCCCGCATTTTAAAATAAAATAAATTATATACTTAATTAAACGAAT | 28 |
| A4 | 0.026638231 | 0.018627764 | TCCCGCATTTTAAAATAAAATAAATTATTAATTTAATTAAACGAAT | 29 |
| B17 | 0.025898959 | 0.020103704 | TCCCGCATTTTAAAATAAAATAAATAATTTAGTTAATTAAACGAAT | 30 |

TABLE 1-continued

| RBS | Average Luminescence (RLU/CFU) | Average Standard Deviation | RBS Sequence | SEQ ID NO. |
|---|---|---|---|---|
| C10 | 0.0258335 | 0.015432121 | TCCCGCATTTTAAAATAAAATAAATTATTATT TTAATTAAACGAAT | 31 |
| A5 | 0.025788394 | 0.020568562 | TCCCGCATTTTAAAATAAAATAAATTATTTCT TTACTTAAACGAAT | 32 |
| A6 | 0.025601325 | 0.014561294 | TCCCGCATTTTAAAATAAAATAAATTATTTCT TTAATTAAACGAAT | 33 |
| A7 | 0.024667081 | 0.011296222 | TCCCGCATTTTAAAATAAAATAAATTATTAGT TTAATTAAACGAAT | 34 |
| B18 | 0.022907649 | 0.021136136 | TCCCGCATTTTAAAATAAAATAAATAATGTAG TTAATTAAACGAAT | 35 |
| C11 | 0.022226069 | 0.013752632 | TCCCGCATTTTAAAATAAAATAAATTATTTTT TTACTTAAACGAAT | 36 |
| C12 | 0.021513645 | 0.017158145 | TCCCGCATTTTAAAATAAAATAAATTATTAGT TTAGTTAAACGAAT | 37 |
| C13 | 0.021491844 | 0.005608953 | TCCCGCATTTTAAAATAAAATAAATTATTAAT TTAATTAAACGAAT | 38 |
| rpiL* | 0.021327937 | 0.015608673 | TCCCGCATTTTAAAATAAAATAAATTATTTAT TTAATTAAACGAAT | 39 |
| C14 | 0.021233545 | 0.010616929 | TCCCGCATTTTAAAATAAAATAAATTATTTCT TTACTTAAACGAAT | 40 |
| C15 | 0.020563998 | 0.012730254 | TCCCGCATTTTAAAATAAAATAAATTATTTCT TTAATTAAACGAAT | 41 |
| B19 | 0.020479274 | 0.02188604 | TCCCGCATTTTAAAATAAAATAAATTATGTAT TTAATTAAACGAAT | 42 |
| C16 | 0.020304739 | 0.010582719 | TCCCGCATTTTAAAATAAAATAAATTATTAGT TTAATTAAACGAAT | 43 |
| A8 | 0.020257089 | 0.020925227 | TCCCGCATTTTAAAATAAAATAAATTATTAGT TTATTTAAACGAAT | 44 |
| C17 | 0.018713639 | 0.013065662 | TCCCGCATTTTAAAATAAAATAAATTATTAGT TTATTTAAACGAAT | 45 |
| A9 | 0.018601123 | 0.01807838 | TCCCGCATTTTAAAATAAAATAAATTATTGTT TTACTTAAACGAAT | 46 |
| C18 | 0.018506456 | 0.013813196 | TCCCGCATTTTAAAATAAAATAAATTATTGTT TTACTTAAACGAAT | 47 |
| C19 | 0.018350882 | 0.009932947 | TCCCGCATTTTAAAATAAAATAAATTATTGCT TTAGTTAAACGAAT | 48 |
| A10 | 0.018348316 | 0.013941115 | TCCCGCATTTTAAAATAAAATAAATTATTGCT TTAGTTAAACGAAT | 49 |
| A11 | 0.01765961 | 0.012488254 | TCCCGCATTTTAAAATAAAATAAATTATTGGT TTAATTAAACGAAT | 50 |
| C20 | 0.017584407 | 0.011147042 | TCCCGCATTTTAAAATAAAATAAATTATTGTT TTAGTTAAACGAAT | 51 |
| B20 | 0.016761674 | 0.007857888 | TCCCGCATTTTAAAATAAAATAAATGATCTAA TTAATTAAACGAAT | 52 |
| B21 | 0.016125201 | 0.011865716 | TCCCGCATTTTAAAATAAAATAAATGATATAT TTAATTAAACGAAT | 53 |
| C21 | 0.016019105 | 0.014862292 | TCCCGCATTTTAAAATAAAATAAATTATTGGT TTAATTAAACGAAT | 54 |
| B22 | 0.015991848 | 0.012072532 | TCCCGCATTTTAAAATAAAATAAATCATGTAA TTAATTAAACGAAT | 55 |

TABLE 1-continued

| RBS | Average Luminescence (RLU/CFU) | Average Standard Deviation | RBS Sequence | SEQ ID NO. |
|---|---|---|---|---|
| A12 | 0.015516562 | 0.005838004 | TCCCGCATTTTAAAATAAAATAAATTATTGTTTTAATTAAACGAAT | 56 |
| C22 | 0.015077891 | 0.007655013 | TCCCGCATTTTAAAATAAAATAAATTATTGTTTTAATTAAACGAAT | 57 |
| A13 | 0.014842069 | 0.012042136 | TCCCGCATTTTAAAATAAAATAAATTATTGATTTACTTAAACGAAT | 58 |
| A14 | 0.014753329 | 0.010693781 | TCCCGCATTTTAAAATAAAATAAATTATTTCTTTATTTAAACGAAT | 59 |
| C23 | 0.014693678 | 0.008891123 | TCCCGCATTTTAAAATAAAATAAATTATTGATTTACTTAAACGAAT | 60 |
| B23 | 0.014640128 | 0.009237609 | TCCCGCATTTTAAAATAAAATAAATAATCTATTTAATTAAACGAAT | 61 |
| B24 | 0.014271145 | 0.013568595 | TCCCGCATTTTAAAATAAAATAAATCATTTATTTAATTAAACGAAT | 62 |
| B25 | 0.014149845 | 0.008879457 | TCCCGCATTTTAAAATAAAATAAATGATTTAGTTAATTAAACGAAT | 63 |
| A15 | 0.013345912 | 0.00619953 | TCCCGCATTTTAAAATAAAATAAATTATTATTTTACTTAAACGAAT | 64 |
| A16 | 0.01329107 | 0.011137157 | TCCCGCATTTTAAAATAAAATAAATTATTTATTTACTTAAACGAAT | 65 |
| A17 | 0.013001037 | 0.008676722 | TCCCGCATTTTAAAATAAAATAAATTATTTTTTTAGTTAAACGAAT | 66 |
| C24 | 0.012872717 | 0.011744627 | TCCCGCATTTTAAAATAAAATAAATTATTTCTTTATTTAAACGAAT | 67 |
| B26 | 0.01271498 | 0.006536795 | TCCCGCATTTTAAAATAAAATAAATTATTTAGTTAATTAAACGAAT | 68 |
| A18 | 0.012374041 | 0.007239521 | TCCCGCATTTTAAAATAAAATAAATTATTCATTTATTTAAACGAAT | 69 |
| A19 | 0.012057948 | 0.009325111 | TCCCGCATTTTAAAATAAAATAAATTATTTTTTTATTTAAACGAAT | 70 |
| A20 | 0.011791304 | 0.007321797 | TCCCGCATTTTAAAATAAAATAAATTATTTATTTATTTAAACGAAT | 71 |
| C25 | 0.011482762 | 0.009546761 | TCCCGCATTTTAAAATAAAATAAATTATTATTTTACTTAAACGAAT | 72 |
| A21 | 0.010177291 | 0.004661365 | TCCCGCATTTTAAAATAAAATAAATTATTTATTTACTTAAACGAAT | 73 |
| B27 | 0.00981525 | 0.00494519 | TCCCGCATTTTAAAATAAAATAAATGATATAGTTAATTAAACGAAT | 74 |
| C26 | 0.009774901 | 0.00361476 | TCCCGCATTTTAAAATAAAATAAATTATTTATTTACTTAAACGAAT | 75 |
| C27 | 0.009752437 | 0.004697982 | TCCCGCATTTTAAAATAAAATAAATTATTTTTTTAGTTAAACGAAT | 76 |
| B28 | 0.009593488 | 0.006063746 | TCCCGCATTTTAAAATAAAATAAATTATGTAGTTAATTAAACGAAT | 77 |
| A22 | 0.009586045 | 0.006222942 | TCCCGCATTTTAAAATAAAATAAATTATTGCTTTATTTAAACGAAT | 78 |
| A23 | 0.009507182 | 0.010092963 | TCCCGCATTTTAAAATAAAATAAATTATTAGTTTACTTAAACGAAT | 79 |
| B29 | 0.009477623 | 0.005634732 | TCCCGCATTTTAAAATAAAATAAATTATATAGTTAATTAAACGAAT | 80 |

TABLE 1-continued

| RBS | Average Luminescence (RLU/CFU) | Average Standard Deviation | RBS Sequence | SEQ ID NO. |
|---|---|---|---|---|
| C28 | 0.009277566 | 0.007911249 | TCCCGCATTTTAAAATAAAATAAATTATTCATTTATTTAAACGAAT | 81 |
| B30 | 0.009275948 | 0.005242916 | TCCCGCATTTTAAAATAAAATAAATGATGTATTTAATTAAACGAAT | 82 |
| A24 | 0.009157814 | 0.003922873 | TCCCGCATTTTAAAATAAAATAAATTATTCTTTTACTTAAACGAAT | 83 |
| A25 | 0.008671077 | 0.005619675 | TCCCGCATTTTAAAATAAAATAAATTATTCCTTTAATTAAACGAAT | 84 |
| B31 | 0.008534421 | 0.007975169 | TCCCGCATTTTAAAATAAAATAAATGATCTAGTTAATTAAACGAAT | 85 |
| C29 | 0.008233091 | 0.005622048 | TCCCGCATTTTAAAATAAAATAAATTATTTTTTTATTTAAACGAAT | 86 |
| A26 | 0.008112849 | 0.007948887 | TCCCGCATTTTAAAATAAAATAAATTATTACTTTATTTAAACGAAT | 87 |
| C30 | 0.008085315 | 0.005587078 | TCCCGCATTTTAAAATAAAATAAATTATTTATTTATTTAAACGAAT | 88 |
| A27 | 0.0079078 | 0.007776077 | TCCCGCATTTTAAAATAAAATAAATTATTGGTTTAGTTAAACGAAT | 89 |
| C31 | 0.007861132 | 0.001765576 | TCCCGCATTTTAAAATAAAATAAATTATTTATTTACTTAAACGAAT | 90 |
| C32 | 0.007716896 | 0.00535098 | TCCCGCATTTTAAAATAAAATAAATTATTGCTTTATTTAAACGAAT | 91 |
| B32 | 0.007096008 | 0.003859981 | TCCCGCATTTTAAAATAAAATAAATGATGTAGTTAATTAAACGAAT | 92 |
| C33 | 0.006912292 | 0.003687466 | TCCCGCATTTTAAAATAAAATAAATTATTAGTTTACTTAAACGAAT | 93 |
| A28 | 0.006883717 | 0.001883353 | TCCCGCATTTTAAAATAAAATAAATTATTCTTTTATTTAAACGAAT | 94 |
| A29 | 0.006832766 | 0.005401737 | TCCCGCATTTTAAAATAAAATAAATTATTCCTTTATTTAAACGAAT | 95 |
| C34 | 0.006727466 | 0.00501383 | TCCCGCATTTTAAAATAAAATAAATTATTCTTTTACTTAAACGAAT | 96 |
| B33 | 0.006272311 | 0.005282458 | TCCCGCATTTTAAAATAAAATAAATCATGTATTTAATTAAACGAAT | 97 |
| B34 | 0.005839641 | 0.002458402 | TCCCGCATTTTAAAATAAAATAAATCATCTATTTAATTAAACGAAT | 98 |
| C35 | 0.005814952 | 0.003885834 | TCCCGCATTTTAAAATAAAATAAATTATTCCTTTAATTAAACGAAT | 99 |
| C36 | 0.005692391 | 0.001097567 | TCCCGCATTTTAAAATAAAATAAATTATTACTTTATTTAAACGAAT | 100 |
| A30 | 0.00560399 | 0.004207987 | TCCCGCATTTTAAAATAAAATAAATTATTCCTTTACTTAAACGAAT | 101 |
| C37 | 0.005598478 | 0.004917959 | TCCCGCATTTTAAAATAAAATAAATTATTGGTTTAGTTAAACGAAT | 102 |
| A31 | 0.005461954 | 0.003952695 | TCCCGCATTTTAAAATAAAATAAATTATTGGTTTATTTAAACGAAT | 103 |
| A32 | 0.005311283 | 0.002312992 | TCCCGCATTTTAAAATAAAATAAATTATTCTTTTAGTTAAACGAAT | 104 |
| B35 | 0.005271921 | 0.003442425 | TCCCGCATTTTAAAATAAAATAAATCATGTACTTAATTAAACGAAT | 105 |

TABLE 1-continued

| RBS | Average Luminescence (RLU/CFU) | Average Standard Deviation | RBS Sequence | SEQ ID NO. |
|---|---|---|---|---|
| A33 | 0.005258284 | 0.002968903 | TCCCGCATTTTAAAATAAAATAAATTATTTCTTTAGTTAAACGAAT | 106 |
| A34 | 0.005181221 | 0.002987732 | TCCCGCATTTTAAAATAAAATAAATTATTTGTTTACTTAAACGAAT | 107 |
| C38 | 0.004774326 | 0.003706679 | TCCCGCATTTTAAAATAAAATAAATTATTCTTTTATTTAAACGAAT | 108 |
| C39 | 0.004533571 | 0.003979636 | TCCCGCATTTTAAAATAAAATAAATTATTCCTTTATTTAAACGAAT | 109 |
| A35 | 0.004513128 | 0.003344091 | TCCCGCATTTTAAAATAAAATAAATTATTCATTTAGTTAAACGAAT | 110 |
| A36 | 0.004309227 | 0.001530154 | TCCCGCATTTTAAAATAAAATAAATTATTTGTTTAGTTAAACGAAT | 111 |
| B36 | 0.004282398 | 0.002044988 | TCCCGCATTTTAAAATAAAATAAATCATATAATTAATTAAACGAAT | 112 |
| A37 | 0.003963532 | 0.001018507 | TCCCGCATTTTAAAATAAAATAAATTATTTGTTTAATTAAACGAAT | 113 |
| A38 | 0.003824437 | 0.004142532 | TCCCGCATTTTAAAATAAAATAAATTATTCCTTTAGTTAAACGAAT | 114 |
| C40 | 0.003758941 | 0.001206597 | TCCCGCATTTTAAAATAAAATAAATTATTCCTTTACTTAAACGAAT | 115 |
| A39 | 0.003302216 | 0.003764382 | TCCCGCATTTTAAAATAAAATAAATTATTGTTTTATTTAAACGAAT | 116 |
| C41 | 0.00310708 | 0.002071032 | TCCCGCATTTTAAAATAAAATAAATTATTGGTTTATTTAAACGAAT | 117 |
| A40 | 0.002991835 | 0.003048933 | TCCCGCATTTTAAAATAAAATAAATTATTTGTTTATTTAAACGAAT | 118 |
| C42 | 0.002800981 | 0.000953927 | TCCCGCATTTTAAAATAAAATAAATTATTCTTTTAGTTAAACGAAT | 119 |
| C43 | 0.002639972 | 0.002313253 | TCCCGCATTTTAAAATAAAATAAATTATTTCTTTAGTTAAACGAAT | 120 |
| B37 | 0.002567042 | 0.001928296 | TCCCGCATTTTAAAATAAAATAAATCATATATTTAATTAAACGAAT | 121 |
| C44 | 0.002490458 | 0.002150977 | TCCCGCATTTTAAAATAAAATAAATTATTTGTTTACTTAAACGAAT | 122 |
| A41 | 0.002416655 | 0.000697011 | TCCCGCATTTTAAAATAAAATAAATTATTATTTTATTTAAACGAAT | 123 |
| C45 | 0.002400024 | 0.002098708 | TCCCGCATTTTAAAATAAAATAAATTATTCATTTAGTTAAACGAAT | 124 |
| C46 | 0.001944909 | 0.001222338 | TCCCGCATTTTAAAATAAAATAAATTATTTGTTTAGTTAAACGAAT | 125 |
| C47 | 0.001889611 | 0.001405816 | TCCCGCATTTTAAAATAAAATAAATTATTTGTTTAATTAAACGAAT | 126 |
| B38 | 0.001793362 | 0.001382499 | TCCCGCATTTTAAAATAAAATAAATCATTTAGTTAATTAAACGAAT | 127 |
| C48 | 0.001758296 | 0.001575362 | TCCCGCATTTTAAAATAAAATAAATTATTCCTTTAGTTAAACGAAT | 128 |
| C49 | 0.001597841 | 0.001364537 | TCCCGCATTTTAAAATAAAATAAATTATTGTTTTATTTAAACGAAT | 129 |
| A42 | 0.00147826 | 0.001197072 | TCCCGCATTTTAAAATAAAATAAATTATTGGTTTACTTAAACGAAT | 130 |

TABLE 1-continued

| RBS | Average Luminescence (RLU/CFU) | Average Standard Deviation | RBS Sequence | SEQ ID NO. |
|---|---|---|---|---|
| A43 | 0.001461263 | 0.000922273 | TCCCGCATTTTAAAATAAAATAAATTATTCGT TTAATTAAACGAAT | 131 |
| C50 | 0.001260649 | 0.000923842 | TCCCGCATTTTAAAATAAAATAAATTATTTGT TTATTTAAACGAAT | 132 |
| B39 | 0.001255393 | 0.001519844 | TCCCGCATTTTAAAATAAAATAAATCATCTAG TTAATTAAACGAAT | 133 |
| B40 | 0.001107845 | 0.000617668 | TCCCGCATTTTAAAATAAAATAAATCATGTAG TTAATTAAACGAAT | 134 |
| A44 | 0.000647832 | 0.000637498 | TCCCGCATTTTAAAATAAAATAAATTATTCGT TTATTTAAACGAAT | 135 |
| C51 | 0.000627266 | 0.000393055 | TCCCGCATTTTAAAATAAAATAAATTATTATT TTATTTAAACGAAT | 136 |
| A45 | 0.000533056 | 0.00037425 | TCCCGCATTTTAAAATAAAATAAATTATTCGT TTACTTAAACGAAT | 137 |
| C52 | 0.000162958 | 0.000109494 | TCCCGCATTTTAAAATAAAATAAATTATTGGT TTACTTAAACGAAT | 138 |
| B41 | 0.000130733 | 7.80708E-05 | TCCCGCATTTTAAAATAAAATAAATCATATAG TTAATTAAACGAAT | 139 |
| C53 | 7.29928E-05 | 2.93717E-05 | TCCCGCATTTTAAAATAAAATAAATTATTCGT TTAATTAAACGAAT | 140 |
| C54 | 3.65058E-05 | 1.67879E-05 | TCCCGCATTTTAAAATAAAATAAATTATTCGT TTATTTAAACGAAT | 141 |
| C55 | 2.62835E-05 | 1.51139E-05 | TCCCGCATTTTAAAATAAAATAAATTATTCGT TTACTTAAACGAAT | 142 |
| C56 | 2.2125E-05 | 1.33933E-05 | TCCCGCATTTTAAAATAAAATAAATTATTCGT TTAGTTAAACGAAT | 143 |

TABLE 2

| Part Name | Type | DNA sequence | SEQ ID NO. |
|---|---|---|---|
| PBT3763 | Rhamnose inducible promoter + RBS | TATTTCGGAGAAAACATGCATAAATCATGCTTTTT TTGCATAAAAAGTAAAATTTATACTGATGTAAGG TTTGGCTATGCAGATTTGTGTCAAAATGCACATCC TTTCTATCAAAATGCGTAAGGAAAAGGAGGAAGG AACCGCCTATCTTTGCAATGTAGGTAAATGGATA CCTTAAATATATAGACAAAATACC | 144 |
| PBT3324 | Chondroitin-sulfate inducible promoter + RBS | TATTTATAAGAGATAGCACATAATTTGAACTATTT TGTACGATTTGAACCCCTCTTTCCAACAAAAGAG GGGTTTCTTTGCATTCGGGAGAAGAACAAGTGAT CTCTCTCTGTAAATACCGGCTAATGATAAACCGAT TTACCATCGGACCTAAAACGATATATTCTATGATA AAGCAATCTTTTACTCTGTCAGTGACA | 145 |
| PBT0268 | Arabinogalactan inducible promoter + RBS | TAAAATACACAAGTACGCGTCTTAATGGAAGATG CGTACTTTTCCATATATCAATGATCTATCCCATTT GAATGATTCCTGAACTTATATTGAACGATTTTTAG ACCTGTTATAGTTAATAGCGATTATGGTCCAATTT TGGAAGTTTTTGAATGATTAGAGAACTTCTTTCTA CTGGATAACTCGCACTTTTGTGACGCATTTGATGC ACAACTAATACTTATTTGGTCTAAATAACTTTATA AATCTAATAGT | 146 |
| PLacO12 | Synthetic IPTG-inducible promoter + RBS | TTACAAAGAAAATTCGACAAACTGTTATTTTTCTA TCTATTTAAATTGTGAGCGGATAACAATTTGAATT GTGAGCGGATAACAATTACCTTTGTCGGCAAATA AAGATATTCTCGTCAAACAAATATAAATAATATA AAC | 147 |

TABLE 2-continued

| Part Name | Type | DNA sequence | SEQ ID NO. |
|---|---|---|---|
| PLacO13 | Synthetic IPTG-inducible promoter + RBS | TTACAAAGAAAATTCGACAAACTGTTATTTTTCTA TCTATTTAAATTGTGAGCGGATAACAATTTGGGTG GGAAACTTTAGTTATGTACCTTTGTCGGCAATTGT GAGCGGATAACAATTAAATAAAGATATTCTCGTC AAACAAATATAAATAATATAAAC | 148 |
| PLacO23 | Synthetic IPTG-inducible promoter + RBS | TTACAAAGAAAATTCGACAAACTGTTATTTTTCTA TCTATTTATTTGAATTGTGAGCGGATAACAATTAC CTTTGTCGGCAATTGTGAGCGGATAACAATTAAA TAAAGATATTCTCGTCAAACAAATATAAATAATA TAAAC | 149 |
| LacIq | Transcriptional repressor | GTGGTGAATGTGAAACCAGTAACGTTATACGATG TCGCAGAGTATGCCGGTGTCTCTTATCAGACCGTT TCCCGCGTGGTGAACCAGGCCAGCCACGTTTCTG CGAAAACGCGGGAAAAAGTGGAAGCGGCGATGG CGGAGCTGAATTACATTCCCAACCGCGTGGCACA ACAACTGGCGGGCAAACAGTCGTTGCTGATTGGC GTTGCCACCTCCAGTCTGGCCCTGCACGCGCCGTC GCAAATTGTCGCGGCGATTAAATCTCGCGCCGAT CAACTGGGTGCCAGCGTGGTGGTGTCGATGGTAG AACGAAGCGGCGTCGAAGCCTGTAAAGCGGCGGT GCACAATCTTCTCGCGCAACGCGTCAGTGGGCTG ATCATTAACTATCCGCTGGATGACCAGGATGCCA TTGCTGTGGAAGCTGCCTGCACTAATGTTCCGGCG TTATTTCTTGATGTCTCTGACCAGACACCCATCAA CAGTATTATTTTCTCCCATGAGGACGGTACGCGAC TGGGCGTGGAGCATCTGGTCGCATTGGGTCACCA GCAAATCGCGCTGTTAGCGGGCCCATTAAGTTCT GTCTCGGCGCGTCTGCGTCTGGCTGGCTGGCATA AATATCTCACTCGCAATCAAATTCAGCCGATAGC GGAACGGGAAGGCGACTGGAGTGCCATGTCCGGT TTTCAACAAACCATGCAAATGCTGAATGAGGGCA TCGTTCCCACTGCGATGCTGGTTGCCAACGATCAG ATGGCGCTGGGCGCAATGCGCGCCATTACCGAGT CCGGGCTGCGCGTTGGTGCGGATATCTCGGTAGT GGGATACGACGATACCGAGGACAGCTCATGTTAT ATCCCGCCGTTAACCACCATCAAACAGGATTTTC GCCTGCTGGGGCAAACCAGCGTGGACCGCTTGCT GCAACTCTCTCAGGGCCAGGCGGTGAAGGGCAAT CAGCTGTTGCCCGTCTCACTGGTGAAAAGAAAAA CCACCCTGGCGCCCAATACGCAAACCGCCTCTCC CCGCGCGTTGGCCGATTCATTAATGCAGCTGGCA CGACAGGTTTCCCGACTGGAAAGCGGGCAGTGA | 150 |
| PcfxA | Constitutive promoter + RBS | TTACAAAGAAAATTCGACAAACTGTTATTTTTCTA TCTATTTATTTGGGTGGGAAACTTTAGTTATGTAC CTTTGTCGGCAAATAAAGATATTCTCGTCAAACA AATATAAATAATATAAAC | 151 |
| PBT1311 | Constitutive promoter + RBS | TGATCTGGAAGAAGCAATGAAAGCTGCTGTTAAG TCTCCGAATCAGGTATTGTTCCTGACAGGTGTATT CCCATCCGGTAAACGCGGATACTTTGCAGTTGAT CTGACTCAGGAATAAATTATAAATTAAGGTAAGA AGATTGTAGGATAAGCTAATGAAATAGAAAAAG GATGCCGTCACACAACTTGTCGGCATTCTTTTTTG TTTTATTAGTTGAAAATATAGTGAAAAAGTTGCCT AAATATGTATGTTAACAAATTATTTGTCGTAACTT TGCACTCCAAATCTGTTTTTAACATATGGCACTA | 152 |
| P1-RBS | Constitutive promoter + RBS | GATAAAGTTTGGAAGATAAAGCTAAAGTTCTTA TCTTTGCAGTCCGAAATAAAGACATATAAAGAA AAGACACC | 153 |
| PcfiA | Constitutive promoter + RBS | GGAGTGAGCTTCTCGGATTTTATTTGTATTTTTGC CATGCCTGATGAGGTTTTGTTTGATTATTTTTTGC AACACTAAGTTAAGTGAATCCTCTGACATGGCAA AATCCTGAGCAACTTTTTGTTGCTCAGGTACTTAA AAAAAATATTTTATAATAGTGTTGCGGAATTAAG GTAAAGAATAAA | 154 |
| Pcep A | Constitutive promoter + RBS | CAAATTTGCGCGCCACAATTATTATTCATACCTTT GTGGACCGTATTACAAAGAACCCAATCATAT | 155 |
| P1 | Constitutive promoter | GATAAAGTTTGGAAGATAAAGCTAAAGTTCTTA TCTTTGCAGT | 156 |

TABLE 2-continued

| Part Name | Type | DNA sequence | SEQ ID NO. |
| --- | --- | --- | --- |
| dCas9 | Catalytically-inactive nuclease for CRISPRi | ATGGATAAGAAATACTCAATAGGCTTAGCTATCG<br>GCACAAATAGCGTCGGATGGGCGGTGATCACTGA<br>TGAATATAAGGTTCCGTCTAAAAAGTTCAAGGTT<br>CTGGGAAATACAGACCGCCACAGTATCAAAAAAA<br>ATCTTATAGGGGCTCTTTTATTTGACAGTGGAGAG<br>ACAGCGGAAGCGACTCGTCTCAAACGGACAGCTC<br>GTAGAAGGTATACACGTCGGAAGAATCGTATTTG<br>TTATCTACAGGAGATTTTTTCAAATGAGATGGCG<br>AAAGTAGATGATAGTTTCTTTCATCGACTTGAAG<br>AGTCTTTTTTGGTGGAAGAAGACAAGAAGCATGA<br>ACGTCATCCTATTTTTGGAAATATAGTAGATGAA<br>GTTGCTTATCATGAGAAATATCCAACTATCTATCA<br>TCTGCGAAAAAAATTGGTAGATTCTACTGATAAA<br>GCGGATTTGCGCTTAATCTATTTGGCCTTAGCGCA<br>TATGATTAAGTTTCGTGGTCATTTTTTGATTGAGG<br>GAGATTTAAATCCTGATAATAGTGATGTGGACAA<br>ACTATTTATCCAGTTGGTACAAACCTACAATCAAT<br>TATTTGAAGAAACCCTATTAACGCAAGTGGAGT<br>AGATGCTAAAGCGATTCTTTCTGCACGATTGAGT<br>AAATCAAGACGATTAGAAAATCTCATTGCTCAGC<br>TCCCCGGTGAGAAGAAAAATGGCTTATTTGGGAA<br>TCTCATTGCTTTGTCATTGGGTTTGACCCCTAATTT<br>TAAATCAAATTTTGATTTGGCAGAAGATGCTAAA<br>TTACAGCTTTCAAAAGATACTTACGATGATGATTT<br>AGATAATTTATTGGCGCAAATTGGAGATCAATAT<br>GCTGATTTGTTTTTGGCAGCTAAGAATTTATCAGA<br>TGCTATTTTACTTTCAGATATCCTAAGAGTAAATA<br>CTGAAATAACTAAGGCTCCCCTATCAGCTTCAAT<br>GATTAAACGCTACGATGAACATCATCAAGACTTG<br>ACTCTTTTAAAAGCTTTAGTTCGACAACAACTTCC<br>AGAAAAGTATAAAGAAATCTTTTTTGATCAATCA<br>AAAAACGGATATGCAGGTTATATTGATGGGGGAG<br>CTAGCCAAGAAGAATTTTATAAATTTATCAAACC<br>AATTTTAGAAAAAATGGATGGTACTGAGGAATTA<br>TTGGTGAAACTAAATCGTGAAGATTTGCTGCGCA<br>AGCAACGGACCTTTGACAACGGCTCTATTCCCCA<br>TCAAATTCACTTGGGTGAGCTGCATGCTATTTTGA<br>GAAGACAAGAAGACTTTTATCCATTTTTAAAAGA<br>CAATCGTGAGAAGATTGAAAAAATCTTGACTTTT<br>CGAATTCCTTATTATGTTGGTCCATTGGCGCGTGG<br>CAATAGTCGTTTTGCATGGATGACTCGGAAGTCT<br>GAAGAAACAATTACCCCATGGAATTTTGAAGAAG<br>TTGTCGATAAAGGTGCTTCAGCTCAATCATTTATT<br>GAACGCATGACAAACTTTGATAAAAATCTTCCAA<br>ATGAAAAGTACTACCAAAACATAGTTTGCTTTA<br>TGAGTATTTTACGGTTTATAACGAATTGACAAAG<br>GTCAAATATGTTACTGAAGGAATGCGAAAACCAG<br>CATTTCTTTCAGGTGAACAGAAGAAAGCCATTGT<br>TGATTTACTCTTCAAAACAAATCGAAAAGTAACC<br>GTTAAGCAATTAAAAGAAGATTATTTCAAAAAAA<br>TAGAATGTTTTGATAGTGTTGAAATTTCAGGAGTT<br>GAAGATAGATTTAATGCTTCATTAGGTACCTACC<br>ATGATTTGCTAAAAATTATTAAAGATAAAGATTTT<br>TTGGATAATGAAGAAAATGAAGATATCTTAGAGG<br>ATATTGTTTTAACATTGACCTTATTTGAAGATAGG<br>GAGATGATTGAGGAAAGACTTAAAACATATGCTC<br>ACCTCTTTGATGATAAGGTGATGAAACAGCTTAA<br>ACGTCGCCGTTATACTGGTTGGGGACGTTTGTCTC<br>GAAAATTGATTAATGGTATTAGGGATAAGCAATC<br>TGGCAAAACAATATTAGATTTTTTGAAATCAGAT<br>GGTTTTGCCAATCGCAATTTTATGCAGCTGATCCA<br>TGATGATAGTTTGACATTTAAAGAAGACATTCAA<br>AAAGCACAAGTGTCTGGACAAGGCGATAGTTTAC<br>ATGAACATATTGCAAATTTAGCTGGTAGCCCTGCT<br>ATTAAAAAAGGTATTTTACAGACTGTAAAAGTTG<br>TTGATGAATTGGTCAAAGTAATGGGGCGGCATAA<br>GCCAGAAAATATCGTTATTGAAATGGCACGTGAA<br>AATCAGACAACTCAAAAGGGCCAGAAAAATTCGC<br>GAGAGCGTATGAAACGAATCGAAGAAGGTATCA<br>AAGAATTAGGAAGTCAGATTCTTAAAGAGCATCC<br>TGTTGAAAATACTCAATTGCAAAATGAAAAGCTC<br>TATCTCTATTATCTCCAAAATGGAAGAGACATGT<br>ATGTGGACCAAGAATTAGATATTAATCGTTTAAG<br>TGATTATGATGTCGATGCCATTGTTCCACAAAGTT<br>TCCTTAAAGACGATTCAATAGACAATAAGGTCTT<br>AACGCGTTCTGATAAAAATCGTGGTAAATCGGAT<br>AACGTTCCAAGTGAAGAAGTAGTCAAAAAGATGA<br>AAAACTATTGGAGACAACTTCTAAACGCCAAGTT | 157 |

| Part Name | Type | DNA sequence | SEQ ID NO. |
|---|---|---|---|
| | | AATCACTCAACGTAAGTTTGATAATTTAACGAAA<br>GCTGAACGTGGAGGTTTGAGTGAACTTGATAAAG<br>CTGGTTTTATCAAACGCCAATTGGTTGAAACTCGC<br>CAAATCACTAAGCATGTGGCACAAATTTTGGATA<br>GTCGCATGAATACTAAATACGATGAAATGATAA<br>ACTTATTCGAGAGGTTAAAGTGATTACCTTAAAA<br>TCTAAATTAGTTTCTGACTTCCGAAAAGATTTCCA<br>ATTCTATAAAGTACGTGAGATTAACAATTACCAT<br>CATGCCCATGATGCGTATCTAAATGCCGTCGTTGG<br>AACTGCTTTGATTAAGAAATATCCAAAACTTGAA<br>TCGGAGTTTGTCTATGGTGATTATAAAGTTTATGA<br>TGTTCGTAAAATGATTGCTAAGTCTGAGCAAGAA<br>ATAGGCAAAGCAACCGCAAAATATTTCTTTTACT<br>CTAATATCATGAACTTCTTCAAAACAGAAATTAC<br>ACTTGCAAATGGAGAGATTCGCAAACGCCCTCTA<br>ATCGAAACTAATGGGAAACTGGAGAAATTGTCT<br>GGGATAAAGGGCGAGATTTTGCCACAGTGCGCAA<br>AGTATTGTCCATGCCCCAAGTCAATATTGTCAAG<br>AAAACAGAAGTACAGACAGGCGGATTCTCCAAG<br>GAGTCAATTTTACCAAAAAGAAATTCGGACAAGC<br>TTATTGCTCGTAAAAAAGACTGGGATCCAAAAAA<br>ATATGGTGGTTTTGATAGTCCAACGGTAGCTTATT<br>CAGTCCTAGTGGTTGCTAAGGTGGAAAAAGGGAA<br>ATCGAAGAAGTTAAAATCCGTTAAAGAGTTACTA<br>GGGATCACAATTATGGAAAGAAGTTCCTTTGAAA<br>AAAATCCGATTGACTTTTTAGAAGCTAAAGGATA<br>TAAGGAAGTTAAAAAAGACTTAATCATTAAACTA<br>CCTAAATATAGTCTTTTTGAGTTAGAAAACGGTCG<br>TAAACGGATGCTGGCTAGTGCCGGAGAATTACAA<br>AAAGGAAATGAGCTGGCTCTGCCAAGCAAATATG<br>TGAATTTTTATATTTAGCTAGTCATTATGAAAAG<br>TTGAAGGGTAGTCCAGAAGATAACGAACAAAAA<br>CAATTGTTTGTGGAGCAGCATAAGCATTATTTAG<br>ATGAGATTATTGAGCAAATCAGTGAATTTTCTAA<br>GCGTGTTATTTTAGCAGATGCCAATTTAGATAAA<br>GTTCTTAGTGCATATAACAAACATAGAGACAAAC<br>CAATACGTGAACAAGCAGAAAATATTATTCATTT<br>ATTTACGTTGACGAATCTTGGAGCTCCCGCTGCTT<br>TTAAATATTTTGATACAACAATTGATCGTAAACG<br>ATATACGTCTACAAAAGAAGTTTTAGATGCCACT<br>CTTATCCATCAATCCATCACTGGTCTTTATGAAAC<br>ACGCATTGATTTGAGTCAGCTAGGAGGTGACTGA | |
| sgRNA | Guide RNA for CRISPRi | NNNNNNNNNNNNNNNNNNNNGTTTTAGAGCTAG<br>AAATAGCAAGTTAAAATAAGGCTAGTCCGTTATC<br>AACTTGAAAAAGTGGCACCGAGTCGGTGCTTTTT<br>T | 158 |
| NanoLuc | Luciferase reporter | ATGGTTTTTACTCTGGAAGATTTTGTTGGCGATTG<br>GCGTCAGACCGCGGGTTATAATTTGGATCAAGTC<br>CTGGAACAGGGTGGCGTAAGCTCTCTGTTCCAGA<br>ACCTGGGTGTGAGCGTGACGCCGATTCAGCGCAT<br>CGTTCTGTCCGGCGAGAACGGTCTGAAAATTGAT<br>ATTCATGTGATCATCCCGTACGAAGGCCTGAGCG<br>GTGACCAAATGGGTCAAATCGAGAAAATCTTTAA<br>AGTCGTCTACCCAGTTGACGATCACCACTTCAAG<br>GTTATCTTGCATTACGGTACGCTGGTGATTGATGG<br>TGTGACCCCGAATATGATTGACTATTTCGGCCGTC<br>CGTATGAAGGCATTGCCGTTTTTGACGGTAAAAA<br>GATCACCGTCACCGGTACCCTGTGGAATGGCAAT<br>AAGATTATTGACGAGCGTCTGATTAACCCGGACG<br>GCAGCCTGCTGTTCCGCGTGACCATCAACGGTGT<br>CACGGGTTGGCGTCTGTGCAGCGCATCCTGGCA<br>TAA | 159 |
| PAM1 | Synthetic constitutive promoter + PBT1311 RBS | TGATCTGGAAGAAGCAATGAAAGCTGCTGTTAAG<br>TCTCCGAATCAGGTATTGTTCCTGACAGGTGTATT<br>CCCATCCGGTAAACGCGGATCTTTGCAGTTGAT<br>CTGACTCAGGAATAAAATTATAAATTAAGGTAAGA<br>AGATTGTAGGATAAGCTAATGAAATAGAAAAAG<br>GATGCCGTCACACAACTTGTCGGCATTCTTTTTTG<br>ctttgcaacagcatagctcagcacagAAGTTGCCTAAATATGTA<br>TGTTAACAAATTATTTGTCGTAACTTTGCACTCCA<br>AATCTGTTTTTAACATATGGCACTA | 160 |

TABLE 2-continued

| Part Name | Type | DNA sequence | SEQ ID NO. |
|---|---|---|---|
| PAM2 | Synthetic constitutive promoter + PBT1311 RBS | TGATCTGGAAGAAGCAATGAAAGCTGCTGTTAAG TCTCCGAATCAGGTATTGTTCCTGACAGGTGTATT CCCATCCGGTAAACGCGGATACTTTGCAGTTGAT CTGACTCAGGAATAAATTATAAATTAAGGTAAGA AGATTGTAGGATAAGCTAATGAAATAGAAAAAG GATGCCGTCACACAACTTGTCGGCATTCTTTTTTG TTTTATTAGTTGAAAATATAGTGAAAAAGTTGCCT AAATATGTATGTTAACAAATTctttgcaacagcatagctcagc acagGCACTCCAAATCTGTTTTTAACATATGGCACT A | 161 |
| PAM3 | Synthetic constitutive promoter + PBT1311 RBS | TGATCTGGAAGAAGCAATGAAAGCTGCTGTTAAG TCTCCGAATCAGGTATTGTTCCTGACAGGTGTATT CCCATCCGGTAAACGCGGATACTTTGCAGTTGAT CTGACTCAGGAATAAATTATAAATTAAGGTAAGA AGATTGTAGGATAAGCTAATGAAATAGAAAAAG GATGCCGTCACACAACTTGTCGGCATTCTTTTTTG TTTTATTAGTTGAAAATATAGTGAAAActttgcaacagca tagctcagcacagATTATTTGTCGTAACTTTGCACTCCAA ATCTGTTTTTAACATATGGCACTA | 162 |
| PAM4 | Synthetic constitutive promoter + PBT1311 RBS | TGATCTGGAAGAAGCAATGAAAGCTGCTGTTAAG TCTCCGAATCAGGTATTGTTCCTGACAGGTGTATT CCCATCCGGTAAACGCGGATACTTTGCAGTTGAT CTGACTCAGGAATAAATTATAAATTAAGGTAAGA AGATTGTAGGATAAGCTAATGAAATAGAAAAAG GATGCCGTCACACAACTTGTCGGCATTCTTTTTTG TTTTATTAGTTGAAAATATAGTGAAAAAGTTGCCT AAATATGTATGTTAACAAATTATTTGTCGTAACTT TGCACTCCctttgcaacagcatagctcagcacagAAATCTGTTTT TAACAT | 163 |
| Int7 | Serine integrase | ATGAAAGTGGCCATTTATGTTCGTGTTAGCACCG ATGAACAGGCCAAAGAAGGTTTTAGCATTCCGGC ACAGCGTGAACGTCTGCGTGCATTTTGTGCAAGC CAGGGTTGGGAAATTGTGCAAGAATATATTGAAG AAGGTTGGAGCGCAAAAGATCTGGATCGTCCGCA GATGCAGCGTCTGCTGAAAGATATCAAAAAAGGC AACATTGATATTGTGCTGGTGTATCGTCTGGATCG CCTGACCCGTAGCGTTCTGGATCTGTATCTGCTGC TGCAGACCTTTGAAAAATACAATGTGGCATTTCG TAGCGCCACCGAAGTTTATGATACCAGCACCGCA ATGGGTCGTCTGTTTATTACCCTGGTTGCAGCACT GGCACAGTGGGAACGTGAAAATCTGGCAGAACGT GTTAAATTTGGTATCGAGCAGATGATCGATGAAG GTAAAAAACCGGGTGGTCATAGCCCGTATGGTTA CAAATTTGATAAAGACTTCAATTGCACCATTATTG AGGAAGAAGCAGACGTTGTTCGTATGATCTATCG CATGTATTGTGATGGTTATGGCTATCGTAGCATTG CAGATCGTCTGAATGAACTGATGGTTAAACCGCG TATTGCCAAAGAATGGAATCATAATAGCGTGCGT GATATCCTGACCAACGATATCTATATTGGCACCTA TCGTTGGGGTGATAAAGTTGTTCCGAATAATCATC CGCCTATTATTAGCGAAACCCTGTTCAAAAAAGC CCAGAAAGAAAAAGAAAAACGTGGCGTTGATCG TAAACGCGTTGGTAAATTTCTGTTTTACCGGTCTGC TGCAGTGTGGTAATTGTGGTGGCCATAAAATGCA GGGCCATTTTGATAAACGTGAGCAGAAAACCTAT TACCGTTGTACCAAATGTCACCGCATTACCAACG AAAAAAACATTCTGGAACCGCTGCTGGATGAAAT TCAGCTGCTGATTACCAGCAAAGAATACTTTATG AGCAAATTCAGCGACCGCTATGATCAGCAAGAGG TTGTTGATGTTAGCGCACTGACAAAAGAACTGGA AAAAATCAAACGCCAGAAAGAGAAATGGTACGA TCTGTATATGGATGATCGTAACCCGATTCCGAAA GAAGAACTGTTTGCCAAAATTAACGAACTGAACA AAAAAGAAGAAAATCTATAGCAAGCTGAGCG AAGTGGAAGAAGATAAAGAACCGGTTGAAGAGA AATATAACCGCCTGAGCAAATGATCGATTTTAA ACAGCAGTTTGAGCAGGCCAACGACTTTACCAAA AAAGAGCTGCTGTTCAGCATCTTCGAAAAGATTG TGATTTATCGCGAGAAAGGCAAGCTGAAAAAAT CACCCTGGATTACACCCTGAAATAA | 164 |
| Int8 | Serine integrase | ATGAAAGTTGCCGTTTATTGTCGTGTTAGCACCCT GGAACAGAAAGAACATGGTCATAGCATTGAAGA ACAAGAGCGTAAACTGAAAAGCTTCTGCGATATT AATGATTGGACCGTGTATGATACCTATATCGATG | 165 |

TABLE 2-continued

| Part Name | Type | DNA sequence | SEQ ID NO. |
|---|---|---|---|
| | | CAGGTTATAGCGGTGCAAAACGTGATCGTCCGGA<br>ACTGCAGCGTCTGATGAATGATATTAACAAATTT<br>GATCTGGTGCTGGTGTATAAACTGGATCGTCTGA<br>CCCGTAATGTTCGTGATCTGCTGGACCTGCTGGAA<br>ATCTTTGAAAAAAATGATGTGAGCTTTCGTAGCG<br>CCACCGAAGTTTATGATACCACCACCGCAATGGG<br>TCGTCTGTTTGTTACCCTGGTTGGTGCAATGGCAG<br>AATGGGAACGTGAAACCATTCGTGAACGTACCCA<br>GATGGGTAAACTGGCAGCACTGCGTAAAGGTATT<br>ATGCTGACCACCCCTCCGTTTTATTATGACCGTGT<br>GGATAATAAGTTTGTGCCGAACAAATACAAAGAC<br>GTTATTCTGTGGGCATATGACGAAGCAATGAAAG<br>GTCAGAGCGCAAAAGCAATTGCACGCAAACTGAA<br>TAATAGCGATATTCCGCCTCCGAATAATACCCAG<br>TGGCAGGGTCGTACCATTACCCATGCCCTGCGTA<br>ATCCGTTTACCCGTGGTCATTTTGATTGGGGTGGT<br>GTGCATATTGAAAATAACCATGAACCGATCATCA<br>CCGATGAGATGTATGAGAAAGTTAAAGATCGCCT<br>GAATGAACGCGTGAACACCAAAAAAGTTCGTCAT<br>ACCAGCATTTTTCGTGGCAAACTGGTTTGTCCGGT<br>TTGTAATGCACGCCTGACCCTGAATAGCCATAAA<br>AAGAAAAGCAATAGCGGCTATATCTTTGTGAAAC<br>AGTACTACTGCAACAACTGTAAAGTTACCCCGAA<br>TCTGAAACCGGTGTACATCAAAGAAAAAGAAGTG<br>ATTAAAGTTTTTTACAATTATCTGAAACGCTTCGA<br>TCTGGAAAAATATGAGGTTACCCAGAAACAGAAC<br>GAACCGGAAATCACCATCGATATCAATAAAGTTA<br>TGGAACAGCGCAAACGCTACCATAAACTGTATGC<br>AAGCGGTCTGATGCAAGAAGATGAACTGTTTGAC<br>CTGATTAAAGAAACCGATCAGACCATTGCCGAAT<br>ATGAAAAACAGAATGAAAACCGCGAAGTGAAGC<br>AGTATGATATCGAAGATATCAAACAGTATAAAGA<br>TCTGCTGTTAGAAATGTGGGATATCAGCTCCGAT<br>GAAGATAAAGAGGACTTTATCAAAATGGCGATTA<br>AAAACATCTATTTTGAATATATCATTGGCACCGGT<br>AACACCAGCCGTAAACGTAATAGCCTGAAAATTA<br>CGAGCATTGAATTCTATTAA | |
| Int9 | Serine integrase | ATGAAAGTGGCCATTTATACCCGTGTTAGCACCCT<br>GGAACAGAAAGAAAAAGGTCATAGCATCGAAGA<br>ACAAGAACGTAAACTGCGTGCATATAGCGATATC<br>AACGATTGGAAAATCCACAAAGTTTATACCGATG<br>CAGGTTATAGCGGTGCCAAAAAAGATCGTCCGGC<br>ACTGCAAGAAATGCTGAATGAAATTGATAACTTC<br>GATCTGGTGCTGGTGTATAAACTGGATCGTCTGA<br>CCCGTAGCGTTAAAGATCTGCTGGAAATTCTGGA<br>ACTGTTTGAAAACAAAAACGTGCTGTTTCGTAGC<br>GCCACCGAAGTTTATGATACCACCAGTGCAATGG<br>GTCGTCTGTTTGTTACCCTGGTTGGTGCAATGGCA<br>GAATGGGAACGTACCACCATTCAAGAACGCACCG<br>CCATGGGTCGCCGTGCAAGCGCACGTAAAGGTCT<br>GGCAAAAACCGTTCCGCCTTTCTATTATGATCGCG<br>TGAATGATAAATTTGTGCCGAACGAGTACAAAAA<br>GGTTCTGCGTTTTGCAGTTGAAGAAGCAAAAAAA<br>GGCACCAGCCTGCGTGAAATTACCATTAAACTGA<br>ACAACAGCAAATACAAAGCACCGCTGGGTAAAA<br>ATTGGCATCGTAGCGTGATTGGTAATGCACTGAC<br>CAGTCCGGTTGCACGTGGTCATCTGGTTTTTGGTG<br>ATATTTTTGTGGAAAACACCCACGAAGCCATTATT<br>AGCGAAGAGGAATATGAAGAAATCAAGCTGCGC<br>ATTAGCGAAAAAACCAATAGCACCATTGTGAAAC<br>ACAACGCCATTTTTCGTAGCAAACTGCTGTGTCCG<br>AATTGCAATCAGAAACTGACCCTGAATACCGTTA<br>AACATACCCCGAAAAACAAAGAGGTGTGGTACA<br>GCAAACTGTATTTTTGCAGCAATTGCAAAAACAC<br>CAAAAATAAGAACGCCTGCAACATCGATGAAGGT<br>GAAGTTCTGAAACAGTTCTACAACTATCTGAAGC<br>AGTTTGATCTGACCAGCTACAAAATTGAAAACCA<br>GCCGAAAGAAATTGAGGATGTGGGCATTGATATT<br>GAAAAACTGCGTAAAGAACGTGCCCGTTGTCAGA<br>CCCTGTTTATTGAAGGTATGATGGATAAAGATGA<br>AGCCTTTCCGATTATTAGCCGCATCGATAAAGAA<br>ATCCACGAGTATGAAAAACGCAAAGACAACGAT<br>AAAGGCAAAACCTTTAACTATGAAAAGATTAAAA<br>ACTTCAAATATAGCCTGCTGAACGGCTGGGAACT<br>GATGGAAGATGAACTGAAAACCGAGTTTATCAAG<br>ATGGCGATCAAAAACATCCACTTTGAGTATGTGA | 166 |

TABLE 2-continued

| Part Name | Type | DNA sequence | SEQ ID NO. |
|---|---|---|---|
| | | AAGGCATCAAAGGTAAACGTCAGAACAGCCTGA<br>AAATTACCGGCATCGAATTCTATTAA | |
| Int12 | Serine integrase | ATGAAAGTGGCCATTTATACCCGTGTTAGCAGCG<br>CAGAACAGGCAAATGAAGGTTATAGCATTCACGA<br>GCAGAAGAAGAAACTGATCAGCTATTGCGAAATC<br>CACGATTGGAACGAGTATAAAGTTTTTACCGATG<br>CAGGTATTAGCGGTGGTAGCATGAAACGTCCGGC<br>ACTGCAAAAACTGATGAAACATCTGAGTTCATTT<br>GATCTGGTGCTGGTGTATAAACTGGATCGTCTGA<br>CCCGTAATGTTCGTGATCTGCTGGATATGCTGGAA<br>GAATTTGAACAGTATAACGTGAGCTTTAAAAGCG<br>CCACCGAAGTTTTTGATACCACCAGTGCAATTGG<br>CAAACTGTTTATTACCATGGTTGGTGCAATGGCA<br>GAATGGGAACGTGAAACCATTCGTGAACGTAGCC<br>TGTTTGGTAGCCGTGCAGCAGTTCGTGAAGGTAA<br>CTATATTCGTGAAGCACCGTTTTGCTATGATAACA<br>TTGAAGGTAAACTGCACCCGAACGAATATGCCAA<br>AGTTATTGATCTGATTGTGAGCATGTTCAAAAAA<br>GGCATTAGCGCCAATGAAATTGCACGTCGTCTGA<br>ATAGCAGCAAAGTTCATGTTCCGAACAAAAAAG<br>CTGGAATCGTAATAGCCTGATTCGTCTGATGCGTA<br>GTCCGGTTCTGCGTGGTCATACCAAATATGGTGAT<br>ATGCTGATTGAAAACACCCATGAACCGGTGCTGA<br>GCGAACATGATTATAATGCAATTAACAACGCCAT<br>CAGCAGCAAAACCCATAAAAGCAAAGTTAAACA<br>CCATGCCATTTTTCGTGGTGCACTGGTTTGTCCGC<br>AGTGTAATCGTCGTCTGCATCTGTATGCAGGCACC<br>GTTAAAGATCGTAAAGGCTATAAATACGATGTGC<br>GTCGCTATAAATGTGAAACCTGCAGCAAAAACAA<br>AGATGTGAAGAATGTGAGCTTCAACGAAAGCGAA<br>GTGGAAAACAAATTCGTCAATCTGCTGAAAAGCT<br>ACGAGCTGAACAAATTTCATATCCGTAAAGTGGA<br>ACCGGTGAAAAAAATCGAGTATGACATCGATAAG<br>ATTAACAAACAGAAAATTAACTATACCCGCAGTT<br>GGAGCCTGGGCTATATTGAAGATGATGAATATTT<br>CGAGCTGATGGAAGAAATCAACGCCACCAAAAA<br>AATGATCGAAGAACAGACCACCGAGAATAAACA<br>GAGCGTTAGCAAAGAGCAGATTCAGAGCATTAAC<br>AACTTTATCCTGAAAGGCTGGGAAGAACTGACCA<br>TCAAAGATAAAGAGGAACTGATTCTGAGCACCGT<br>GGATAAAATCGAATTTAACTTCATCCCGAAAGAT<br>AAAAAACATAAAACCAATACCCTGGATATTAACA<br>ATATTCACTTTAAATTCTAA | 167 |
| GH022 | RBS | CATATAAAAGAAAAGACACC | 168 |
| GH023 | RBS | GAAATAAAGACATATAAAAGAAAAGACACC | 169 |
| GH078 | RBS | AAAAGGATCTATTATAAGGAGGCACTCACC | 170 |
| RC500 | RBS | AATAGGCCTTTCGGTCCACACTCTCTATAGGCAA<br>A | 171 |
| rpiL* | RBS | CGCATTTTAAAATAAAATAAATTATTTATTTAATT<br>AAACGAAT | 172 |

TABLE 3

| Name | Expression Level (RLU/CFU) | Sequence |
|---|---|---|
| rpiL*-B1 | 9.02E-02 | TCCCGCATTTTAAAATAAAATAAATTATTCGTTTAGTTAAACGAAT<br>ATG (SEQ ID NO: 173) |
| rpiL* | 2.13E-02 | TCCCGCATTTTAAAATAAAATAAATTATTTATTTAATTAAACGAAT<br>ATG<br>(SEQ ID NO: 174) |
| rpiL*-C33 | 6.91E-03 | TCCCGCATTTTAAAATAAAATAAATTATTAGTTTACTTAAACGAAT<br>ATG<br>(SEQ ID NO: 175) |

TABLE 3-continued

| Name | Expression Level (RLU/CFU) | Sequence |
|---|---|---|
| rpiL*-C39 | 1.26E-03 | TCCCGCATTTTAAAATAAAATAAATCATCTAGTTAATTAAACGAATATG (SEQ ID NO: 176) |
| rpiL*-C51 | 6.27E-04 | TCCCGCATTTTAAAATAAAATAAATTATTATTTTATTTAAACGAATATG (SEQ ID NO: 177) |
| rpiL*-C52 | 1.63E-04 | TCCCGCATTTTAAAATAAAATAAATTATTGGTTTACTTAAACGAATATG (SEQ ID NO: 178) |
| rpiL*-C53 | 7.30E-05 | TCCCGCATTTTAAAATAAAATAAATTATTCGTTTAATTAAACGAATATG (SEQ ID NO: 179) |
| rpiL*-C56 | 2.21E-05 | TCCCGCATTTTAAAATAAAATAAATTATTCGTTTAGTTAAACGAATATG (SEQ ID NO: 180) |

It should be understood that the pNBU2 vector described herein may be substituted with pNBU1 (SEQ ID NO: 209), provided herein. Thus, any of any of the components provided in Tables 1-3 and 5, for example, may be used in an pNBU1 or pNBU2 vector backbone. In some embodiments, a pNBU1 backbone is used instead of the pNBU2 backbone for any one or more of the constructs described in Table 4.

TABLE 4

| Identifier | Plasmid | Relevant Features |
|---|---|---|
| pMM553 | pNBU2-BT1311-NanoLuc | NanoLuc expressed constitutively from PBT1311, pNBU2 backbone, AmpR |
| pMM555 | pNBU2-PcfxA-NanoLuc | NanoLuc expressed constitutively from PcfxA, pNBU2 backbone, AmpR |
| pMM575 | pNBU2-PcfiA-NanoLuc | NanoLuc expressed constitutively from PcfiA, pNBU2 backbone, AmpR |
| pMM579 | pNBU2-P1-NanoLuc | NanoLuc expressed constitutively from P1, pNBU2 backbone, AmpR |
| pMM580 | pNBU2-PcepA-NanoLuc | NanoLuc expressed constitutively from PcepA, pNBU2 backbone, AmpR |
| pMM585 | pNBU2-LacIq-PcfxA-LacO12-NanoLuc | IPTG-inducible NanoLuc expression, pNBU2 backbone, AmpR |
| pMM596 | pNBU2-LacIq-PcfxA-LacO13-NanoLuc | IPTG-inducible NanoLuc expression, pNBU2 backbone, AmpR |
| pMM597 | pNBU2-LacIq-PcfxA-LacO23-NanoLuc | IPTG-inducible NanoLuc expression, pNBU2 backbone, AmpR |
| pMM656 | pNBU2-Prha-NL | Rhamnose-inducible NanoLuc expression, pNBU2 backbone, AmpR |
| pMM659 | pNBU2-Pbt3324-NL | Chondroitin sulfate-inducible NanoLuc expression, pNBU2 backbone, AmpR |
| pMM660 | pNBU2-Pbt0268-NL | Arabinogalactan-inducible NanoLuc expression, pNBU2 backbone, AmpR |
| pMM668 | pExchange(tdk) | B. thetaiotaomicron suicide vector expressing thymidine kinase |
| pMM704 | pNBU2-BtdCas9-BT1854 | IPTG-inducible CRISPRi vector targeting BT1854, pNBU2 backbone, AmpR |
| pMM705 | pNBU2-BtdCas9-BT1754 | IPTG-inducible CRISPRi vector targeting BT1754, pNBU2 backbone, AmpR |
| pMM710 | pNBU2-BtdCas9-NS | IPTG-inducible CRISPRi vector targeting nonsense sequence (NS), pNBU2 backbone, AmpR |
| pMM723 | pNBU2 | NBU2 integration vector backbone, R6K origin, RP4 oriT, AmpR |
| pMM725 | pNBU2-BtdCas9-NL3 | IPTG-inducible CRISPRi vector targeting NanoLuc (NL3), constitutive NanoLuc, pNBU2 backbone, AmpR |
| pMM731 | pNBU2-BtdCas9-NL1 | IPTG-inducible CRISPRi vector targeting NanoLuc (NL1), constitutive NanoLuc, pNBU2 backbone, AmpR |
| pMM732 | pNBU2-BtdCas9-NL2 | IPTG-inducible CRISPRi vector targeting NanoLuc (NL2), constitutive NanoLuc, pNBU2 backbone, AmpR |
| pMM733 | pNBU2-BtdCas9-NL4 | IPTG-inducible CRISPRi vector targeting NanoLuc (NL4), constitutive NanoLuc, pNBU2 backbone, AmpR |

TABLE 4-continued

| Identifier | Plasmid | Relevant Features |
|---|---|---|
| pMM750 | pNBU2-BtdCas9-PR2 | IPTG-inducible CRISPRi vector targeting PcfiA (PR2), constitutive NanoLuc, pNBU2 backbone, AmpR |
| pMM763 | pNBU2-BtdCas9-PR1 | IPTG-inducible CRISPRi vector targeting PcfiA (PR1), constitutive NanoLuc, pNBU2 backbone, AmpR |
| pMM764 | pNBU2-BtdCas9-NS-NL | IPTG-inducible CRISPRi vector targeting nonsense sequence (NS), constitutive NanoLuc, pNBU2 backbone, AmpR |
| pAT751 | pNBU2-PAM1-NanoLuc | NanoLuc expressed constitutively from PAM1, pNBU2 backbone, AmpR |
| pAT752 | pNBU2-PAM2-NanoLuc | NanoLuc expressed constitutively from PAM2, pNBU2 backbone, AmpR |
| pAT753 | pNBU2-PAM3-NanoLuc | NanoLuc expressed constitutively from PAM3, pNBU2 backbone, AmpR |
| pAT754 | pNBU2-PAM4-NanoLuc | NanoLuc expressed constitutively from PAM4, pNBU2 backbone, AmpR |
| pAT587 | pNBU2-PBT1311-GH022-NanoLuc | NanoLuc expressed constitutively from PBT1311 and GH022 RBS, pNBU2 backbone, AmpR |
| pAT588 | pNBU2-PBT1311-GH023-NanoLuc | NanoLuc expressed constitutively from PBT1311 and GH023 RBS, pNBU2 backbone, AmpR |
| pAT590 | pNBU2-PBT1311-GH049-NanoLuc | NanoLuc expressed constitutively from PBT1311 and GH049 RBS, pNBU2 backbone, AmpR |
| pAT593 | pNBU2-PBT1311-rpiL*-NanoLuc | NanoLuc expressed constitutively from PBT1311 and rpiL* RBS, pNBU2 backbone, AmpR |
| pAT695 | pNBU2-PBT1311-RC500-NanoLuc | NanoLuc expressed constitutively from PBT1311 and RC500 RBS, pNBU2 backbone, AmpR |
| pAT772 | pNBU2-PAM1-GH078-NanoLuc | NanoLuc expressed constitutively from PAM1 and GH078 RBS, pNBU2 backbone, AmpR |
| pAT773 | pNBU2-PAM1-GH022-NanoLuc | NanoLuc expressed constitutively from PAM1 and GH022 RBS, pNBU2 backbone, AmpR |
| pAT774 | pNBU2-PAM1-GH023-NanoLuc | NanoLuc expressed constitutively from PAM1 and GH023 RBS, pNBU2 backbone, AmpR |
| pAT775 | pNBU2-PAM1-rpiL*-NanoLuc | NanoLuc expressed constitutively from PAM1 and rpiL* RBS, pNBU2 backbone, AmpR |
| pAT776 | pNBU2-PAM1-RC500-NanoLuc | NanoLuc expressed constitutively from PAM1 and RC500 RBS, pNBU2 backbone, AmpR |
| pAT779 | pNBU2-PAM2-GH078-NanoLuc | NanoLuc expressed constitutively from PAM2 and GH078 RBS, pNBU2 backbone, AmpR |
| pAT780 | pNBU2-PAM2-GH022-NanoLuc | NanoLuc expressed constitutively from PAM2 and GH022 RBS, pNBU2 backbone, AmpR |
| pAT781 | pNBU2-PAM2-GH023-NanoLuc | NanoLuc expressed constitutively from PAM2 and GH023 RBS, pNBU2 backbone, AmpR |
| pAT782 | pNBU2-PAM2-rpiL*-NanoLuc | NanoLuc expressed constitutively from PAM2 and rpiL* RBS, pNBU2 backbone, AmpR |
| pAT783 | pNBU2-PAM2-RC500-NanoLuc | NanoLuc expressed constitutively from PAM2 and RC500 RBS, pNBU2 backbone, AmpR |
| pAT786 | pNBU2-PAM3-GH078-NanoLuc | NanoLuc expressed constitutively from PAM3 and GH078 RBS, pNBU2 backbone, AmpR |
| pAT787 | pNBU2-PAM3-GH022-NanoLuc | NanoLuc expressed constitutively from PAM3 and GH022 RBS, pNBU2 backbone, AmpR |
| pAT788 | pNBU2-PAM3-GH023-NanoLuc | NanoLuc expressed constitutively from PAM3 and GH023 RBS, pNBU2 backbone, AmpR |
| pAT789 | pNBU2-PAM3-rpiL*-NanoLuc | NanoLuc expressed constitutively from PAM3 and rpiL* RBS, pNBU2 backbone, AmpR |
| pAT790 | pNBU2-PAM3-RC500-NanoLuc | NanoLuc expressed constitutively from PAM3 and RC500 RBS, pNBU2 backbone, AmpR |
| pAT793 | pNBU2-PAM4-GH078-NanoLuc | NanoLuc expressed constitutively from PAM4 and GH078 RBS, pNBU2 backbone, AmpR |
| pAT794 | pNBU2-PAM4-GH022-NanoLuc | NanoLuc expressed constitutively from PAM4 and GH022 RBS, pNBU2 backbone, AmpR |
| pAT795 | pNBU2-PAM4-GH023-NanoLuc | NanoLuc expressed constitutively from PAM4 and GH023 RBS, pNBU2 backbone, AmpR |
| pAT796 | pNBU2-PAM4-rpiL*-NanoLuc | NanoLuc expressed constitutively from PAM4 and rpiL* RBS, pNBU2 backbone, AmpR |
| pAT797 | pNBU2-PAM4-RC500-NanoLuc | NanoLuc expressed constitutively from PAM4 and RC500 RBS, pNBU2 backbone, AmpR |
| pAT890 | pNBU2-PAM4-rpiL*-int7 | Int7 expressed constitutively from PAM4 and the rpiL* RBS, pNBU2 backbone, AmpR |
| pAT891 | pNBU2-PAM4-rpiL*-int8 | Int8 expressed constitutively from PAM4 and the rpiL* RBS, pNBU2 backbone, AmpR |
| pAT892 | pNBU2-PAM4-rpiL*-int9 | Int9 expressed constitutively from PAM4 and the rpiL* RBS, pNBU2 backbone, AmpR |
| pAT895 | pNBU2-PAM4-rpiL*-int12 | Int12 expressed constitutively from PAM4 and the rpiL* RBS, pNBU2 backbone, AmpR |
| pAT847 | pExchange-tdk-BT2107-MA | Memory arrary integration vector for insertion between BT2113 and BT2114 in the B. thetaiotaomicron chromosome, AmpR |

TABLE 4-continued

| Identifier | Plasmid | Relevant Features |
|---|---|---|
| pAT937 | pNBU2-Prha-rpiL*C51-Int12 | Rhamnose-inducible Int12 expression vector with rpiL*C51 RBS, pNBU2 backbone, AmpR |

TABLE 5

| Name | Target Sequence | Sequence | SEQ ID NO. |
|---|---|---|---|
| NL1 | NanoLuc | TTGATCCAAATTATAACCCG | 181 |
| NL2 | NanoLuc | AGCTTACGCCACCCTGTTCC | 182 |
| NL3 | NanoLuc | TCACGCTCACACCCAGGTTC | 183 |
| NL4 | NanoLuc | GACAGAACGATGCGCTGAAT | 184 |
| PR1 | $P_{cfiA}$ | AAACAAAACCTCATCAGGCA | 185 |
| PR2 | $P_{cfiA}$ | GAAGCTCACTCCTTAGCACG | 186 |
| NS | Nonsense control | CTGGAATGAATTGGCCTATG | 187 |
| BT1754 | BT1754 | GAAAATGGGGTGTATCCTGC | 188 |
| BT1854 | BT1854 | ATTGAAGAACAAAAGCAGTT | 189 |

TABLE 6

| Primer | Target | Sequence | SEQ ID NO. |
|---|---|---|---|
| oAT614 | rpiL* RBS library A | GCATGAAGACTCCTCCCGCATTTTAAAATAAA ATAAATTATTTATNNNATTAAACGAATATGGT TTTTACTCTGGAAGATTTTGTTG | 190 |
| oAT615 | rpiL* RBS library B | GCATGAAGACTCCTCCCGCATTTTAAAATAAA ATAAATNATNTANTTAATTAAACGAATATGG TTTTTACTCTGGAAGATTTTGTTG | 191 |
| oAT616 | rpiL* RBS library C | GCATGAAGACTCCTCCCGCATTTTAAAATAAA ATAAATTATTNNTTTANTTAAACGAATATGGT TTTTACTCTGGAAGATTTTGTTG | 192 |
| oAT617 | rpiL* RBS library | GCATGAAGACTCGGAGTGCAAAGTTACGACA AATAATTTG | 193 |
| oAT836 | MA12F | ATAAACGTTCGTGGTAACTATGGG | 194 |
| oAT837 | MA12R | GACCTTCGGAATTCTTCCTAGTG | 195 |
| oAT838 | Flip12R | GGAACACTCCGTCGGTCG | 196 |
| oAT870 | Int12F | CCGTAATGTTCGTGATCTGC | 197 |
| oAT871 | Int12R | TTTCACGTTCCCATTCTGC | 198 |
| oAT826 | MA7F | CCCAGGAGAGTTATCGACTTGC | 199 |
| oAT827 | MA7R | TGTCCAAAATCGACCTACACCG | 200 |
| oAT830 | MA8F | TCACACAGGTTTATAACACCCAATC | 201 |
| oAT831 | MA8R | CCGGTGCATTGGTTAAGACTG | 202 |
| oAT833 | MA9F | TGCAAGACTGTACATACTTCCATAG | 203 |
| oAT834 | MA9R | TCTAGAGGATCTCAGGCAGC | 204 |
| mmD662 | qNL-178-F | GTGATCATCCCGTACGAAGG | 205 |
| mmD663 | qNL-302-R | ATCACCAGCGTACCGTAATG | 206 |

IntN1 attP Site
(SEQ ID NO: 207)
CTACGTTCAACCAAAAGAAATAATGACTTACTGCTATATTTTTTGCACGT
GTGGGGAAAATGTGGGAAAATTCAAGCAAAAGAAAAAGCTAAGTATTGA
ACTATCAAATACTTAGCTTTCTTTCTTGTACCCAGACCCCGCATTTGAAA
TAATTAAAGTGGGGAAAATGTGGGTAAAAAGAAAAATGCGGAAAAACGCC
ACAATTACACTGTATTTCAATATGTTATAATCCTATTAAATTTTAATCCA
AGTTTAATCGAATTGCAAAATATTTAGCAGATGTGGGGAAAATGCTGGGG
AAAATATTTATATTTGCAGCAGAGTAAAAT IntN1 coding sequence
(SEQ ID NO: 208)
ATGAAAGTAACCTTTATCATTAAAAAAGCAGCCAAACGATATGATACAGA
ATCCATGGCTACAATCTATGTCCGTTTTAGAAACGGAAGGCAGTTAGACT
CCGTTGCTCCTACTCAGTTAGCCATCAATCCCAATCTATGGGATGATAAA
GACGAATGTGTAAAAACGAAAGCTGTCTGCAATGAAGAAATGCGTACCCA
TATAAATGAAGAGATACGCCAGTTGAAAACCTATATCGAGAAGGTATATC
AACAAGAAAGGAAGCAATAGACAAAGAATGGCTAAAAACAACACTTGAT
AAATTTTACCATCCTGAAAAATATTTTTTGCCGGAGGAAGTGGTTATCAA
GCCTACCATTGGAGAACTATTCGATGAATTTCTAAACAAGCACCCTTTGT
CGGAAGTACGAAAGAAAAATTTCCGGGTTGTCAAAAGAGCCTTACTGCGT
TATGAACTATATGTAAGGGCTACAAAGAGAGGACAAAAGGGCTTTATCCT
TGATGTGGATTTGGTAACACCTGACACGCTTCGGGATATGTGGGATTTCT
TTCAGAACGAATACCAGTATTATGAACTTTACCCGAGCATTTATGAAGCC
ATTCCCGAAAAGAGGACACCACAGCCCAGAAGCAAAAACACGCTGATAGA
CTGTTTTTCAAGAATACGCACATTCTTCCTGTGGTGCTTCGATAACAAAC
GCACCACAAACAGACCTTTCGACAAGTTTCCGATAGAGGAGTGTACATAT
GGTACACCTTATTATATAACACTCGAAGAAAGGGACAGGATTTTTAATGC
AGACCTTTCTGCCACCCCACAACTGGCAATACAGAGGGATATATTCATAT
TTCAGACACTGATAGGATGCAGGGTGAGCGACCTGTACCGAATGACCAAA
CTAAATGTGGTCAATGAAGCCATAGAATATATTCCCAAGAAAACCAAAGA
GGGGAATCCGGTTACGGTACGTGTTCCACTTAACGACAAAGCGAAAGAAA
TCCTTGAACGCTACAAAGAATATGAGGGAAAACTGTTGCCGTTCATATCC
GAGCAAAAGTACAATGATGCCATAAAAAAGATATTCAAATTAGCTGGAGT
TGACCGCATCGTAACAATCTTAGACCCGTTGACGCACAACGAAATCAAAC
GACCTATTTATGAAGTGGCAAGCAGCCATCTGGCAAGACGTACGTTTATC
GGCAATATCTATAAAAAAGTGAAAGACCCGAACCTTGTTTCCGCACTGTC
GGGACACAAGGAGGGAAGCAAAGCTTTCAGACGATACAGGGATATTGACG
AAGAAATGAAGAAGACCTTGTAAAACTACTGGACTGA pNBU1-L23R-NL
(SEQ ID NO: 209)
ATGGTTTTTACTCTGGAAGATTTTGTTGGCGATTGGCGTCAGACCGCGGG
TTATAATTTGGATCAAGTCCTGGAACAGGGTGGCGTAAGCTCTCTGTTCC
AGAACCTGGGTGTGAGCGTGACGCCGATTCAGCGCATCGTTCTGTCCGGC
GAGAACGGTCTGAAAATTGATATTCATGTGATCATCCCGTACGAAGGCCT
GAGCGGTGACCAAATGGGTCAAATCGAGAAAATCTTTAAAGTCGTCTACC
CAGTTGACGATCACCACTTCAAGGTTATCTTGCATTACGGTACGCTGGTG
ATTGATGGTGTGACCCCGAATATGATTGACTATTTCGGCCGTCCGTATGA
AGGCATTGCCGTTTTTGACGGTAAAAAGATCACCGTCACCGGTACCCTGT
GGAATGGCAATAAGATTATTGACGAGCGTCTGATTAACCCGGACGGCAGC
CTGCTGTTCCGCGTGACCATCAACGGTGTCACGGGTTGGCGTCTGTGCGA
GCGCATCCTGGCATAATGAACTGCACTTGCTTTGATAATTAATGATAAAC
AATCTAAAAGCACTCTAATCGTTATCGGAGTGCTTTTAGATTACTAATCA
AATTGCTTCTACTAATTGCCTATCTTCCAGTGATGGAACAGCATTTGTGC
ATTGGCTGCAACAATCAGCCTTGATCTGGAAGAAGCAATGAAAGCTGCTG
TTAAGTCTCCGAATCAGGTATTGTTCCTGACAGGTGTATTCCCATCCGGT
AAACGCGGATACTTTGCAGTTGATCTGACTCAGGAATAAATTATAAATTA
AGGTAAGAAGATTGTAGGATAAGCTAATGAAATAGAAAAAGGATGCCGTC
ACACAACTTGTCGGCATTCTTTTTTGTTTTATTAGTTGAAAATATAGTGA
AAAAGTTGCCTAAATATGTATGTTAACAAATTATTTGTCGTAACTTTGCA
CTCCAAATCTGTTTTTAACATATGGCACTAGTGGTGAATGTGAAACCAGT
AACGTTATACGATGTCGCAGAGTATGCCGGTGTCTCTTATCAGACCGTTT
CCCGCGTGGTGAACCAGGCCAGCCACGTTTCTGCGAAAACGCGGGAAAAA
GTGGAAGCGGCGATGGCGGAGCTGAATTACATTCCCAACCGCGTGGCACA
ACAACTGGCGGGCAAACAGTCGTTGCTGATTGGCGTTGCCACCTCCAGTC
TGGCCCTGCACGCGCCGTCGCAAATTGTCGCGGCGATTAAATCTCGCGCC
GATCAACTGGGTGCCAGCGTGGTGGTGTCGATGGTAGAACGAAGCGGCGT
CGAAGCCTGTAAAGCGGCGGTGCACAATCTTCTCGCGCAACGCGTCAGTG
GGCTGATCATTAACTATCCGCTGGATGACCAGGATGCCATTCTGTGGAA
GCTGCCTGCACTAATGTTCCGGCGTTATTTCTTGATGTCTCTGACCAGAC
ACCCATCAACAGTATTATTTTCTCCCATGAGGACGGTACGCGACTGGGCG
TGGAGCATCTGGTCGCATTGGGTCACCAGCAAATCGCGCTGTTAGCGGGC
CCATTAAGTTCTGTCTCGGCGCGTCTGCGTCTGGCTGGCTGGCATAAATA
TCTCACTCGCAATCAAATTCAGCCGATAGCGGAACGGGAAGGCGACTGGA
GTGCCATGTCCGGTTTTCAACAAACCATGCAAATGCTGAATGAGGGCATC
GTTCCCACTGCGATGCTGGTTGCCAACGATCAGATGGCGCTGGGCGCAAT
GCGCGCCATTACCGAGTCCGGGCTGCGCGTTGGTGCGGATATCTCGGTAG
TGGGATACGACGATACCGAGGACAGCTCATGTTATATCCCGCCGTTAACC
ACCATCAAACAGGATTTTCGCCTGCTGGGGCAAACCAGCGTGGACCGCTT
GCTGCAACTCTCTCAGGGCCAGGCGGTGAAGGGCAATCAGCTGTTGCCCG
TCTCACTGGTGAAAGAAAAACCACCCTGGCGCCCAATACGCAAACCGCC
TCTCCCCGCGCGTTGGCCGATTCATTAATGCAGCTGGCACGACAGGTTTC
CCGACTGGAAAGCGGGCAGTGAGCTTTCCTCGGTACCAAATTCCAGAAAA
GAGGCCTCCCGAAAGGGGGGCCTTTTTTCGTTTTGGTCCTACTTGTGCCT
GTTCTATTTCCGAACCGACCGCTTGTATGAATCCATCAAAATTCGTTTTC
TCTATGTTGGATTCCTTGTTGCTCATATTGTGATGATAATTTCTACAAAT -continued

```
ATAGTCATTGGTAACTATCTATGAAACTGTTTGATACTTTTATCAGTCCA
GTAGTTTTACAAGGTCTTTCTTCATTTCTTCGTCAATATCCCTGTATCGT
CTGAAAGCTTTGCTTCCCTCCTTGTGTCCCGACAGTGCGGAAACAAGGTT
CGGGTCTTTCACTTTTTTATAGATATTGCCGATAAACGTACGTCTTGCCA
GATGGCTGCTTGCCACTTCATAAATAGGTCGTTTGATTTCGTTGTGCGTC
AACGGGTCTAAGATTGTTACGATGCGGTCAACTCCAGCTAATTTGAATAT
CTTTTTTATGGCATCATTGTACTTTTGCTCGGATATGAACGGCAACAGTT
TTCCCTCATATTCTTTGTAGCGTTCAAGGATTTCTTTCGCTTTGTCGTTA
AGTGGAACACGTACCGTAACCGGATTCCCCTCTTTGGTTTTCTTGGGAAT
ATATTCTATGGCTTCATTGACCACATTTAGTTTGGTCATTCGGTACAGGT
CGCTCACCCTGCATCCTATCAGTGTCTGAAATATGAATATATCCCTCTGT
ATTGCCAGTTGTGGGGTGGCAGAAAGGTCTGCATTAAAAATCCTGTCCCT
TTCTTCGAGTGTTATATAATAAGGTGTACCATATGTACACTCCTCTATCG
GAAACTTGTCGAAAGGTCTGTTTGTGGTGCGTTTGTTATCGAAGCACCAC
AGGAAGAATGTGCGTATTCTTGAAAAACAGTCTATCAGCGTGTTTTGCT
TCTGGGCTGTGGTGTCCTCTTTTCGGGAATGGCTTCATAAATGCTCGGGT
AAAGTTCATAATACTGGTATTCGTTCTGAAAGAAATCCCACATATCCCGA
AGCGTGTCAGGTGTTACCAAATCCACATCAAGGATAAAGCCCTTTTGTCC
TCTCTTTGTAGCCCTTACATATAGTTCATAACGCAGTAAGGCTCTTTTGA
CAACCCGGAAATTTTTCTTTCGTACTTCCGACAAAGGGTGCTTGTTTAGA
AATTCATCGAATAGTTCTCCAATGGTAGGCTTGATAACCACTTCCTCCGG
CAAAAAATATTTTTCAGGATGGTAAAATTTATCAAGTGTTGTTTTTAGCC
ATTCTTTGTCTATTGCTTCCTTTTCTTGTTGATATACCTTCTCGATATAG
GTTTTCAACTGGCGTATCTCTTCATTTATATGGGTACGCATTTCTTCATT
GCAGACAGCTTTCGTTTTTACACATTCGTCTTTATCATCCCATAGATTGG
GATTGATGGCTAACTGAGTAGGAGCAACGGAGTCTAACTGCCTTCCGTTT
CTAAAACGGACATAGATTGTAGCCATGGATTCTGTATCATATCGTTTGGC
TGCTTTTTTAATGATAAAGGTTACTTTCATAGACTTTCAGGTTGAATTTT
ACTCTGCTGCAAATATAAATATTTTCCCCAGCATTTTCCCCACATCTGCT
AAATATTTTGCAATTCGATTAAACTTGGATTAAAATTTAATAGGATTATA
ACATATTGAAATACAGTGTAATTGTGGCGTTTTTCCGCATTTTTCTTTTT
ACCCACATTTTCCCCACTTTAATTATTTCAAATGCCGGGTCTGGGTACAA
GAAAGAAAGCTAAGTATTTGATAGTTCAATACTTAGCTTTTTCTTTTGCT
TGAATTTTCCCCACATTTTCCCCACACGTGCAAAAAATATAGCAGTAAGT
CATTATTTCTTTTGGTTGAACGTAGAGAGTAGCGATATTAAAAGAATCCG
ATGAGAAAGACTAATATTTATCTATCCATTCAGTTTGATTTTTCAGGAC
TTTACATCGTCCTGAAAGTATTTGTTGGTACCGGTACCGAGGACGCGTAA
ACATTTACAGTTGCATGTGGCCTATTGTTTTTAGCCGTTAAATATTTAT
AACTATTAAATAGCGATACAAATTGTTCGAAACTAATATTGTTTATATCA
TATATTCTCGCATGTTTTAAAGCTTTATTAAATTGATTTTTTGTAAACAG
TTTTTCGTACTCTTTGTTAACCCATTTCATTACAAAAGTTTCATATTTTT
```

-continued

```
TTCTCTCTTTAAATGCCATTTTTGCTGGCTTTCTTTTTAATACAATTAAT
GTGCTATCCACTTTAGGTTTTGGATGGAAATAATACCTAGGAATTTTTGC
TAATATAGAAATATCTACCTCTGCCATTAACAGCAATGCTAGTGATCTGT
TTGTATCTAATAACATTTTAGCAAAACCATATTCCACTATTAAATAACTT
ATTGTGGCTGAACTTTCAAAAACAATTTTTCGAATTATATTTGTGCTTAT
GTTGTAAGGTATGCTGCCAAATATTTTATATGGATTGTGGCTAGGAAATG
TAAATTTCAGTATATCATCATTTACTATTTGATAGTTAGGATAATTTAAG
AGCTTATTACGAGTTACCTCACATAATTTAGAATCAATTTCTATCGCCGT
TACAAAATTACATCTCTTTACCAATCCAGCAGTAAAATGACCTTTCCCTG
CACCTATTTCAAAGATGTTATCTTTTTCATCTAAACTTATGCAATTCATT
ATTTTTTCTATGTGATATTTTGAAGTAATAAAATTTTGACTATCTTTTAT
ATTTACTTTGTTCATTATAACCTCTCCTTAATTTATTGCATCTCTTTTCG
AATATTTATGTTTTTTGAGAAAAGAACGTACTCATGGTTCATCCCGATAT
GCGTATCGGTCTGTATATCAGCAACTTTCTATGTGTTTCAACTACAATAG
TCATCTATTCTCATCTTTCTGAGTCCACCCCCTGCAAAGCCCCTCTTTAC
GACATAAAAATTCGGTCGGAAAAGGTATGCAAAAGATGTTTCTCTCTTTA
AGAGAAACTCTTCGGGATGCAAAAATATGAAAATAACTCCAATTCACCAA
ATTATATAGCGACTTTTTTACAAAATGCTAAAATTTGTTGATTTCCGTCA
AGCAATTGTTGAGCAAAAATGTCTTTTACGATAAAATGATACCTCAATAT
CAACTGTTTAGCAAAACGATATTTCTCTTAAAGAGAGAAACACCTTTTTG
TTCACCAATCCCCGACTTTTAATCCCGCGGCCATGATTGAAAAAGGAAGA
GTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGA
CGCCGGGCAAGAGCAACTCGGTCGCCGCATACACTATTCTCAGAATGACT
TGGTTGAGTACTCACCAGTCACAGAAAAGCATCTTACGGATGGCATGACA
GTAAGAGAATTATGCAGTGCTGCCATAACCATGAGTGATAACACTGCGGC
CAACTTACTTCTGACAACGATCGGAGGACCGAAGGAGCTAACCGCTTTTT
TGCACAACATGGGGGATCATGTAACTCGCCTTGATCGTTGGGAACCGGAG
CTGAATGAAGCCATACCAAACGACGAGCGTGACACCACGATGCCTGTAGC
AATGGCAACAACGTTGCGCAAACTATTAACTGGCGAACTACTTACTCTAG
CTTCCCGGCAACAATTAATAGACTGGATGGAGGCGGATAAAGTTGCAGGA
CCACTTCTGCGCTCGGCCCTTCCGGCTGGCTGGTTTATTGCTGATAAATC
TGGAGCCGGTGAGCGTGGGTCTCGCGGTATCATTGCAGCACTGGGGCCAG
ATGGTAAGCCCTCCCGTATCGTAGTTATCTACACGACGGGGAGTCAGGCA
ACTATGGATGAACGAAATAGACAGATCGCTGAGATAGGTGCCTCACTGAT
TAAGCATTGGTAACTGTCAGACCAAGTTTACTCATAACGCGTCAATTCGA
GGGGGATCAATTCCGTGATAGGTGGGCTGCCCTTCCTGGTTGGCTTGGTT
TCATCAGCCATCCGCTTGCCCTCATCTGTTACGCCGGCGGTAGCCGGCCA
```

```
-continued
GCCTCGCAGAGCAGGATTCCCGTTGAGCACCGCCAGGTGCGAATAAGGGA

CAGTGAAGAAGGAACACCCGCTCGCGGGTGGCCTACTTCACCTATCCTGC

CCGGCTGACGCCGTTGGATACACCAAGGAAAGTCTACACGAACCCTTTGG

CAAAATCCTGTATATCGTGCGAAAAAGGATGGATATACCGAAAAAATCGC

TATAATGACCCCGAAGCAGGGTTATGCAGCGGAAAACGGAATTGATCCGG

CCACGATGCGTCCGGCGTAGAGGATCTGAAGATCAGCAGTTCAACCTGTT

GATAGTACGTACTAAGCTCTCATGTTTCACGTACTAAGCTCTCATGTTTA

ACGTACTAAGCTCTCATGTTTAACGAACTAAACCCTCATGGCTAACGTAC

TAAGCTCTCATGGCTAACGTACTAAGCTCTCATGTTTCACGTACTAAGCT

CTCATGTTTGAACAATAAAATTAATATAAATCAGCAACTTAAATAGCCTC

TAAGGTTTTAAGTTTTATAAGAAAAAAAAGAATATATAAGGCTTTTAAAG

CTTTTAAGGTTTAACGGTTGTGGACAACAAGCCAGGGATGTAACGCACTG

AGAAGCCCTTAGAGCCTCTCAAAGCAATTTTGAGTGACACAGGAACACTT

AACGGCTGACATGGGAATTCCCCTCCACCGCGGTGGTTACAAAGAAAATT

CGACAAACTGTTATTTTTCTATCTATTTATTTGAATTGTGAGCGGATAAC

AATTACCTTTGTCGGCAATTGTGAGCGGATAACAATTAAATAAAGATATT

CTCGTCAAACAAATATAAATAATATAAAC
```

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A *Bacteroides* bacterium comprising:
   (a) an engineered nucleic acid comprising a region containing a *Bacteroides* promoter comprising the −33/−7 consensus sequence of TTTG/TAnnTTTG and a nucleotide sequence encoding a ribosomal binding site (RBS) operably linked to a nucleotide sequence encoding a recombinase, wherein the nucleotide sequence encoding the RBS comprises a sequence selected from the group consisting of: SEQ ID NO: 1-SEQ ID NO: 30, SEQ ID NO: 32-SEQ ID NO: 35, SEQ ID NO: 39, SEQ ID NO: 42, SEQ ID NO: 44, SEQ ID NO: 46, SEQ ID NO: 48, SEQ ID NO: 50-SEQ ID NO: 53, SEQ ID NO: 55, SEQ ID NO: 56, SEQ ID NO: 58, SEQ ID NO: 59, SEQ ID NO: 61-SEQ ID NO: 66, SEQ ID NO: 68-SEQ ID NO: 71, SEQ ID NO: 74, SEQ ID NO: 77-SEQ ID NO: 80, SEQ ID NO: 82-SEQ ID NO: 85, SEQ ID NO: 87, SEQ ID NO: 89, SEQ ID NO: 92, SEQ ID NO: 94, SEQ ID NO: 95, SEQ ID NO: 97, SEQ ID NO: 98, SEQ ID NO: 101, SEQ ID NO: 103-107, SEQ ID NO: 110-SEQ ID NO: 114, SEQ ID NO: 116, SEQ ID NO: 118, SEQ ID NO: 121, SEQ ID NO: 123, SQ ID NO: 127, SEQ ID NO: 130, SEQ ID NO: 131, SEQ ID NO: 133-SEQ ID NO: 135, SEQ ID NO: 137, SEQ ID NO: 139, and SEQ ID NO: 168-SEQ ID NO: 172; and
   (b) an engineered nucleic acid comprising a *Bacteroides* promoter comprising the −33/−7 consensus sequence of TTTG/TAnnTTTG and a nucleotide sequence encoding a RBS operably linked to a nucleotide sequence encoding a molecule of interest, wherein the nucleotide sequence encoding the molecule of interest is flanked by a pair of cognate recombinase recognition sequences, wherein the nucleotide sequence encoding the RBS comprises a sequence selected from the group consisting of: SEQ ID NO: 1-SEQ ID NO: 30, SEQ ID NO: 32-SEQ ID NO: 35, SEQ ID NO: 39, SEQ ID NO: 42, SEQ ID NO: 44, SEQ ID NO: 46, SEQ ID NO: 48, SEQ ID NO: 50-SEQ ID NO: 53, SEQ ID NO: 55, SEQ ID NO: 56, SEQ ID NO: 58, SEQ ID NO: 59, SEQ ID NO: 61-SEQ ID NO: 66, SEQ ID NO: 68-SEQ ID NO: 71, SEQ ID NO: 74, SEQ ID NO: 77-SEQ ID NO: 80, SEQ ID NO: 82-SEQ ID NO: 85, SEQ ID NO: 87, SEQ ID NO: 89, SEQ ID NO: 92, SEQ ID NO: 94, SEQ ID NO: 95, SEQ ID NO: 97, SEQ ID NO: 98, SEQ ID NO: 101, SEQ ID NO: 103-107, SEQ ID NO: 110-SEQ ID NO: 114, SEQ ID NO: 116, SEQ ID NO: 118, SEQ ID NO: 121, SEQ ID NO: 123, SQ ID NO: 127, SEQ ID NO: 130, SEQ ID NO: 131, SEQ ID NO: 133-SEQ ID NO: 135, SEQ ID NO: 137, SEQ ID NO: 139, and SEQ ID NO: 168-SEQ ID NO: 172.

2. The *Bacteroides* bacterium of claim 1, wherein the *Bacteroides* promoter of (a) and/or (b) is constitutive.

3. The *Bacteroides* bacterium of claim 1, wherein the *Bacteroides* promoter of (a) and/or (b) is inducible.

4. The *Bacteroides* bacterium of claim 1, wherein the recombinase is a serine recombinase or a tyrosine recombinase.

5. The *Bacteroides* bacterium of claim 4, wherein the recombinase is a serine recombinase.

6. The *Bacteroides* bacterium of claim 5, wherein the serine recombinase is selected from the group consisting of Int7, Int8, Int9, Int12, Bxb1, φC31, TP901, TG1, φBT1, R4, φRV1, φFC1, MR11, A118, U153 and gp29.

7. The *Bacteroides* bacterium of claim 1, wherein the engineered nucleic acid of (a) is on the same vector as the engineered nucleic acid of (b).

8. The *Bacteroides* bacterium of claim 7, wherein the vector further comprises a promoter operably linked to a nucleic acid encoding a recombinase from a conjugated transposon.

9. The *Bacteroides* bacterium of claim 8, wherein the recombinase is IntN1 or IntN2.

10. The *Bacteroides* bacterium of claim 1, wherein the engineered nucleic acid of (a) and the engineered nucleic acid of (b) are integrated into the chromosome of the *Bacteroides* bacterium.

11. The *Bacteroides* bacterium of claim 7, wherein the vector is a plasmid.

12. A *Bacteroides* bacterium comprising an engineered nucleic acid comprising:
    a *Bacteroides* promoter comprising the −33/−7 consensus sequence of TTTG/TAnnTTTG and a nucleotide sequence encoding a ribosomal binding site (RBS) operably linked to a nucleotide sequence encoding a molecule of interest, wherein the RBS comprises a sequence selected from the group consisting of: SEQ ID NO: 1-SEQ ID NO: 30, SEQ ID NO: 32-SEQ ID NO: 35, SEQ ID NO: 39, SEQ ID NO: 42, SEQ ID NO: 44, SEQ ID NO: 46, SEQ ID NO: 48, SEQ ID NO: 50-SEQ ID NO: 53, SEQ ID NO: 55, SEQ ID NO: 56, SEQ ID NO: 58, SEQ ID NO: 59, SEQ ID NO: 61-SEQ ID NO: 66, SEQ ID NO: 68-SEQ ID NO: 71, SEQ ID NO: 74, SEQ ID NO: 77-SEQ ID NO: 80, SEQ ID NO: 82-SEQ ID NO: 85, SEQ ID NO: 87, SEQ ID NO: 89, SEQ ID NO: 92, SEQ ID NO: 94, SEQ ID NO: 95, SEQ ID NO: 97, SEQ ID NO: 98, SEQ ID NO: 101, SEQ ID NO: 103-107, SEQ ID NO: 110-SEQ ID NO: 114, SEQ ID NO: 116, SEQ ID NO: 118, SEQ ID NO: 121, SEQ ID NO: 123, SQ ID NO: 127, SEQ ID NO: 130, SEQ ID NO: 131, SEQ ID NO: 133-SEQ ID NO: 135, SEQ ID NO: 137, SEQ ID NO: 139, and SEQ ID NO: 168-SEQ ID NO: 172.

13. The *Bacteroides* bacterium of claim 1, wherein the molecule of interest is a therapeutic molecule, a prophylactic molecule, or a diagnostic molecule.

14. A method of expressing a molecule of interest in a *Bacteroides* bacterium, the method comprising culturing the *Bacteroides* bacterium of claim 1, wherein the molecule of interest is a therapeutic molecule.

15. The *Bacteroides* bacterium of claim 1, wherein the *Bacteroides* bacterium is *B. thetaiotaomicron*.

16. The *Bacteroides* bacterium of claim 12, wherein the *Bacteroides* bacterium is *B. thetaiotaomicron*.

* * * * *

UNITED STATES PATENT AND TRADEMARK OFFICE
CERTIFICATE OF CORRECTION

| | |
|---|---|
| PATENT NO. | : 11,591,604 B2 |
| APPLICATION NO. | : 15/580859 |
| DATED | : February 28, 2023 |
| INVENTOR(S) | : Timothy Kuan-Ta Lu et al. |

It is certified that error appears in the above-identified patent and that said Letters Patent is hereby corrected as shown below:

In the Specification

At Column 1, Lines 16-18, in the paragraph under the heading "FEDERALLY SPONSORED RESEARCH":
"This invention was made with government support under Grant No. FA8721-05-C-0002 awarded by the U.S. Air Force. The government has certain rights in the invention."

Should read:
--This invention was made with government support under FA8721-05-C-0002 awarded by the Air Force Office of Scientific Research. The government has certain rights in the invention.--

Signed and Sealed this
Sixteenth Day of May, 2023

Katherine Kelly Vidal
*Director of the United States Patent and Trademark Office*